(12) United States Patent
Lashinski et al.

(10) Patent No.: US 10,939,997 B2
(45) Date of Patent: *Mar. 9, 2021

(54) VALVE REPLACEMENT USING MOVEABLE RESTRAINTS AND ANGLED STRUTS

(71) Applicant: Millipede, Inc, Santa Rosa, CA (US)

(72) Inventors: Randall Lashinski, Windsor, CA (US);
Matthew Rust, Windsor, CA (US);
Patrick Macaulay, Windsor, CA (US);
Richard Glenn, Santa Rosa, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/285,566

(22) Filed: Feb. 26, 2019

(65) Prior Publication Data

US 2019/0262133 A1 Aug. 29, 2019

Related U.S. Application Data

(63) Continuation of application No. 15/829,760, filed on Dec. 1, 2017, now Pat. No. 10,258,466, which is a continuation of application No. 15/043,301, filed on Feb. 12, 2016, now Pat. No. 9,848,983.

(60) Provisional application No. 62/116,248, filed on Feb. 13, 2015.

(51) Int. Cl.
*A61F 2/24* (2006.01)

(52) U.S. Cl.
CPC .......... *A61F 2/2418* (2013.01); *A61F 2/2409* (2013.01); *A61F 2/2445* (2013.01); *A61F 2/2412* (2013.01); *A61F 2/2433* (2013.01); *A61F 2220/0008* (2013.01); *A61F 2220/0016* (2013.01); *A61F 2230/0069* (2013.01); *A61F 2230/0091* (2013.01); *A61F 2250/001* (2013.01); *A61F 2250/0007* (2013.01)

(58) Field of Classification Search
CPC .......... A61F 2/24; A61F 2/2418; A61F 2/2412
USPC .................................... 623/2.1–2.19
See application file for complete search history.

(56) References Cited

U.S. PATENT DOCUMENTS

| 8,998,979 | B2 * | 4/2015 | Seguin | A61F 2/2409 623/2.1 |
| 9,848,983 | B2 * | 12/2017 | Lashinski | A61F 2/2418 |
| 10,258,466 | B2 * | 4/2019 | Lashinski | A61F 2/2409 |

(Continued)

FOREIGN PATENT DOCUMENTS

| JP | 2007044516 A | 2/2007 |
| JP | 2012508033 A | 4/2012 |
| WO | 2009132187 A1 | 10/2009 |

*Primary Examiner* — Suzette J Gherbi
(74) *Attorney, Agent, or Firm* — Kacvinsky Daisak Bluni PLLC

(57) ABSTRACT

Features for a heart valve device are described. The device may include a frame with anchors configured to secure the device to tissue. The frame may include a flared end or skirt for additional securement of the implanted device. The device may include a seal such as a barrier and/or cuff for preventing leakage. The device may contract for endovascular delivery of the device to the heart and expand for securement within the heart, such as the within the native mitral valve annulus. The device may include a replacement valve. The valve may have leaflets configured to re-direct blood flow along a primary flow axis.

20 Claims, 47 Drawing Sheets

(56) References Cited

U.S. PATENT DOCUMENTS

| | | | |
|---|---|---|---|
| 2013/0138207 A1* | 5/2013 | Quadri | A61F 2/2436 623/2.18 |
| 2014/0222136 A1* | 8/2014 | Geist | A61F 2/2418 623/2.11 |
| 2014/0309731 A1* | 10/2014 | Quadri | A61F 2/2418 623/2.18 |
| 2016/0095704 A1* | 4/2016 | Whitman | A61F 2/2409 623/2.11 |
| 2016/0128829 A1* | 5/2016 | Oba | A61F 2/2418 623/2.11 |
| 2017/0035562 A1* | 2/2017 | Quadri | A61F 2/2439 |
| 2017/0035564 A1* | 2/2017 | Ryan | A61F 2/2418 |
| 2017/0231759 A1* | 8/2017 | Geist | A61F 2/2466 623/2.18 |

* cited by examiner

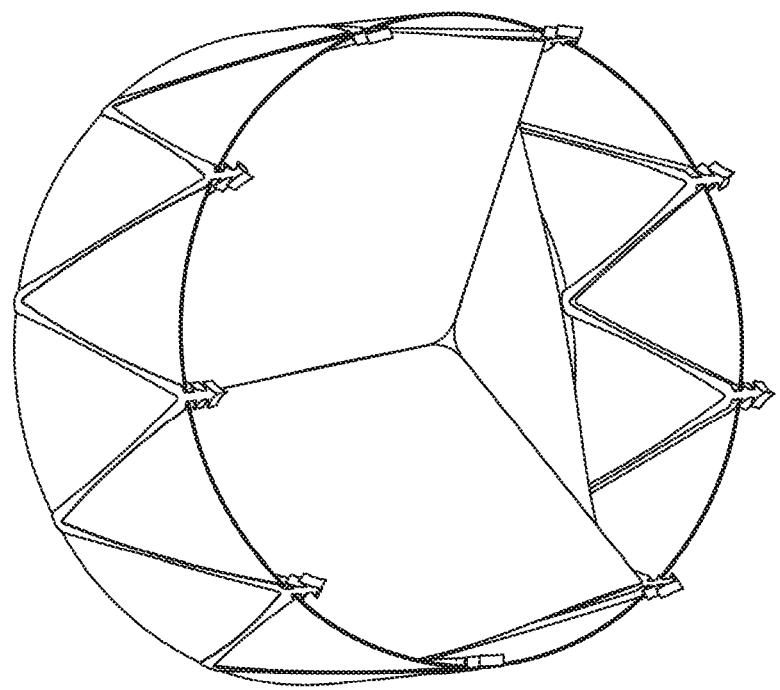
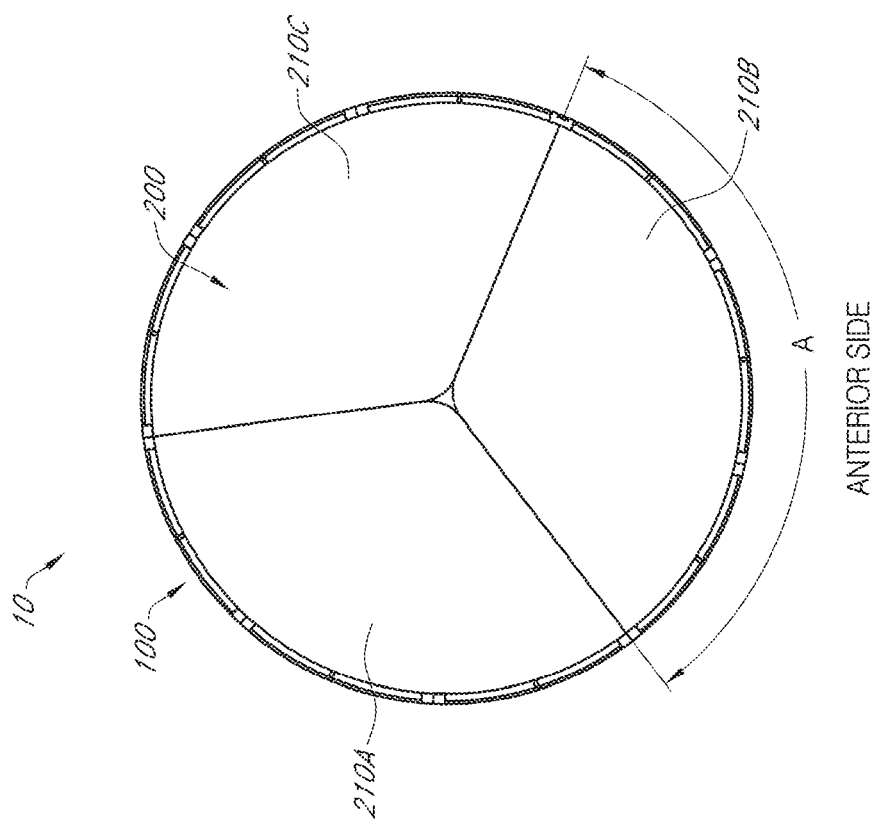
FIG. 8B

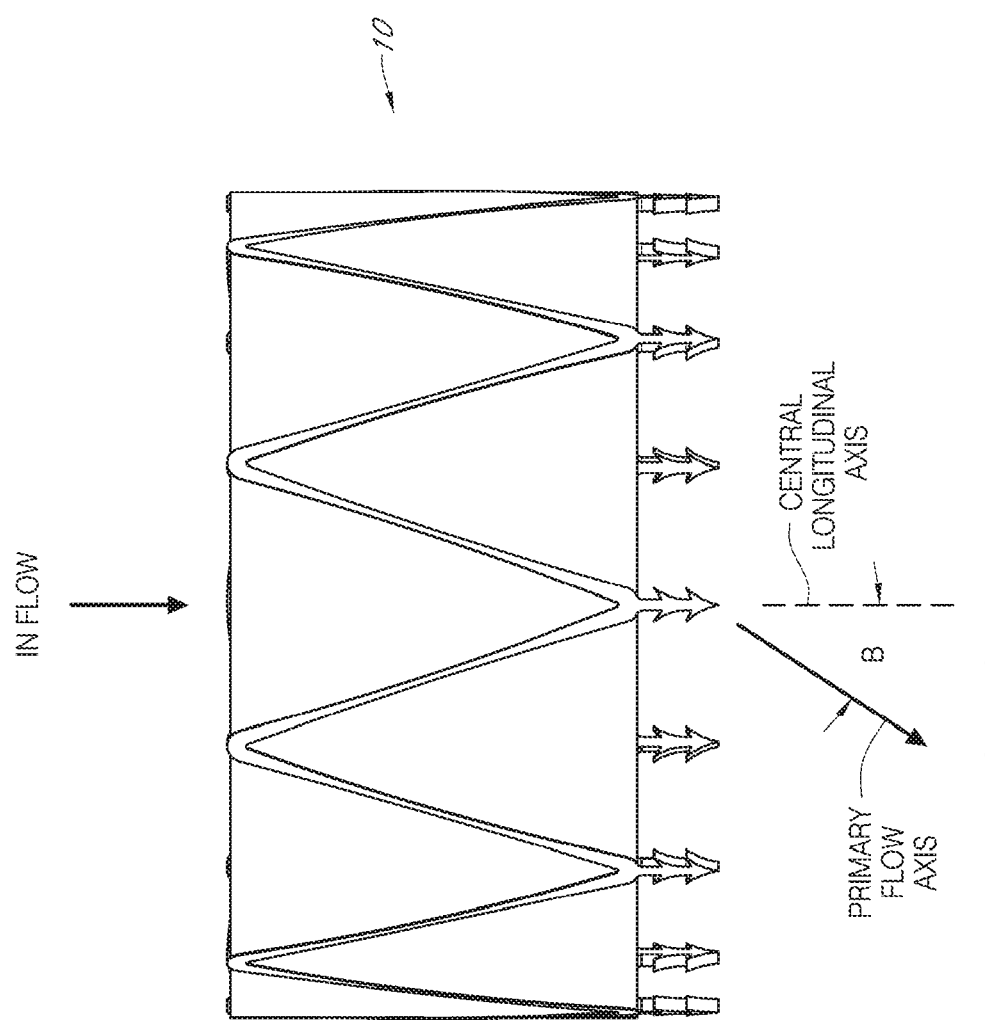

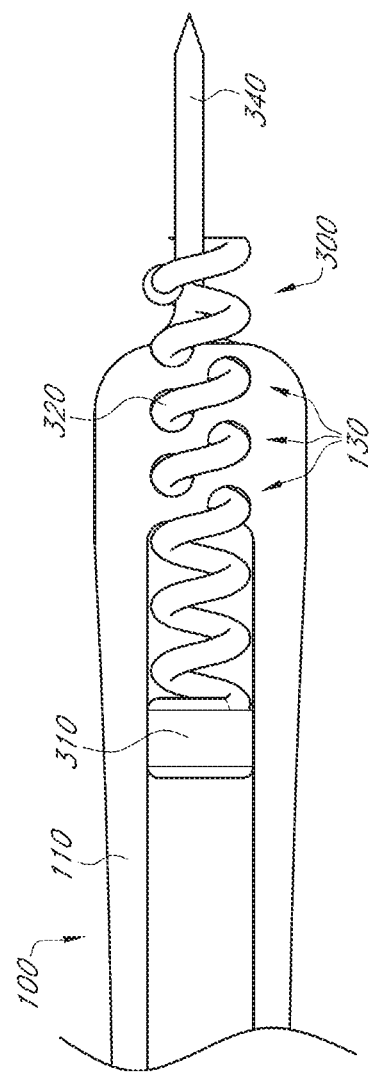

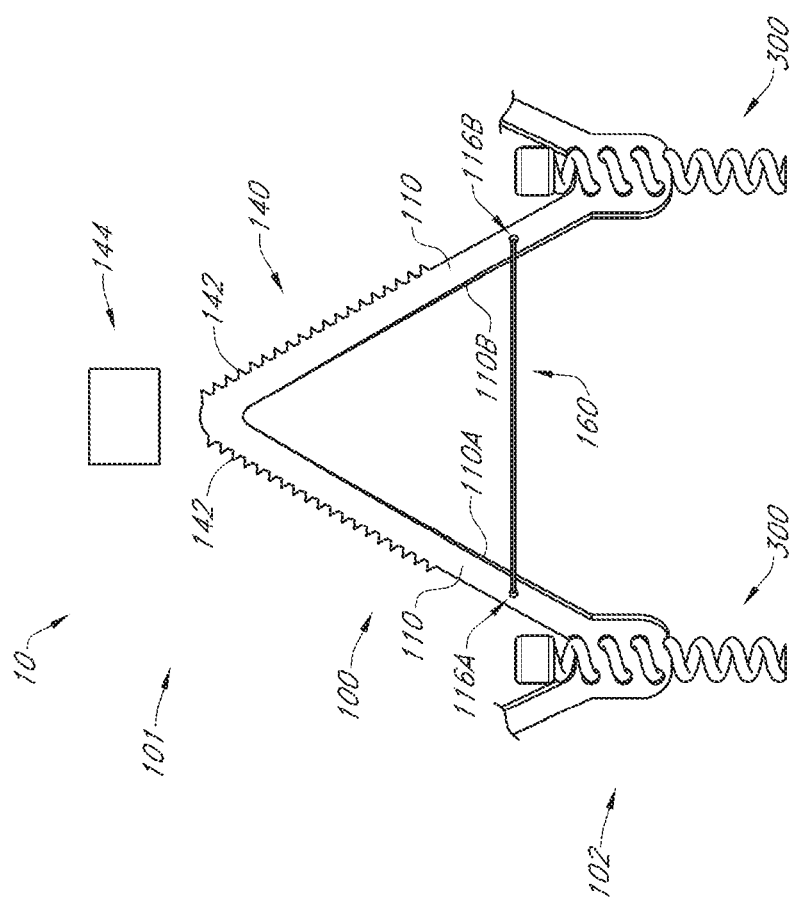

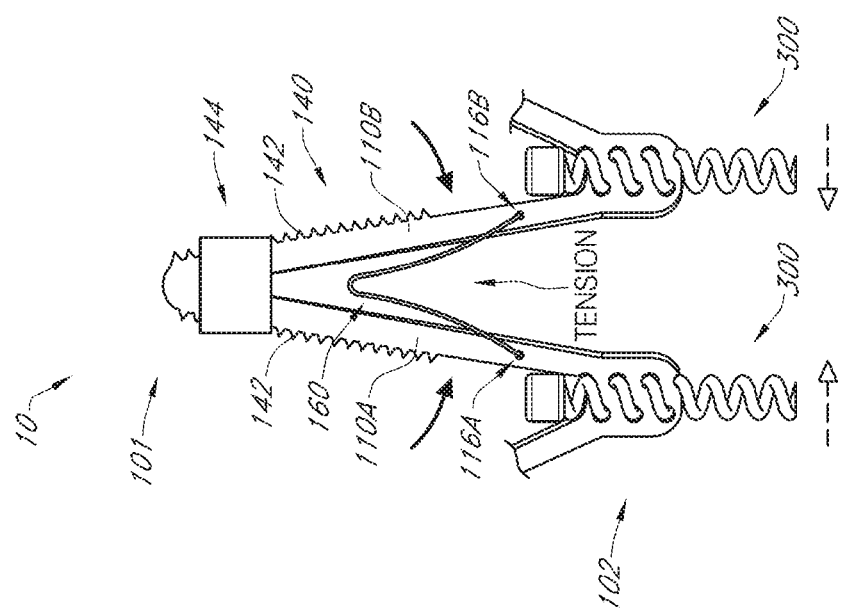

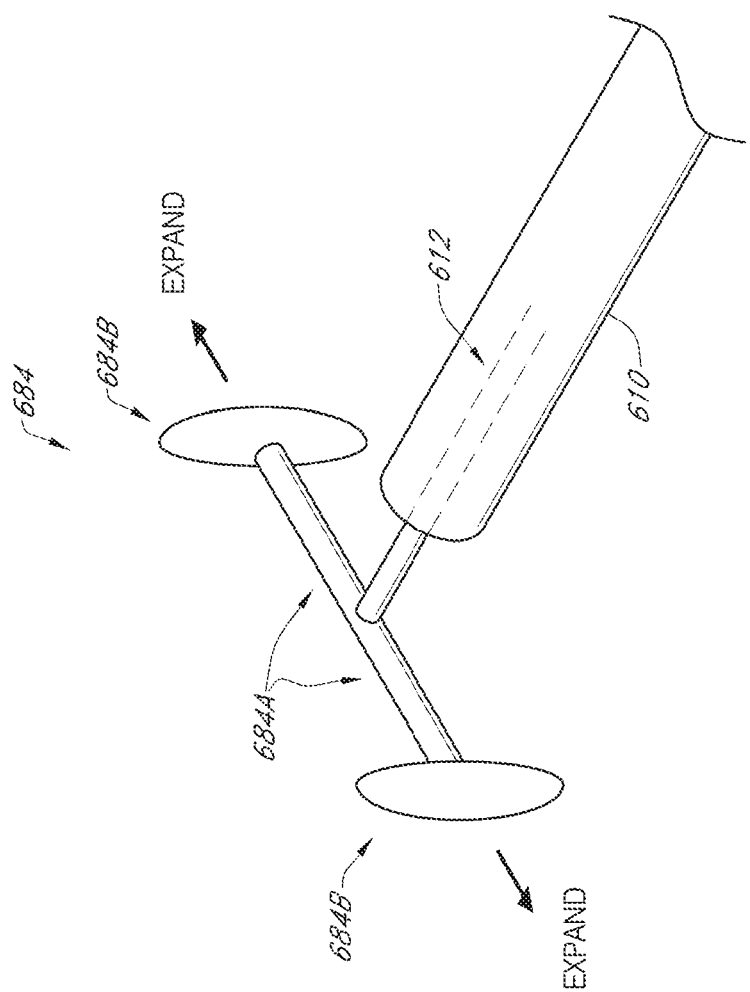

VALVE REPLACEMENT USING MOVEABLE RESTRAINTS AND ANGLED STRUTS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is a continuation application of U.S. patent application Ser. No. 15/829,760, filed Dec. 1, 2017, which is a continuation application of U.S. patent application Ser. No. 15/043,301, filed Feb. 12, 2016, and issued as U.S. Pat. No. 9,848,983, which claims the priority benefit under 35 U.S.C. § 119(e) of U.S. Provisional Application No. 62/116,248, filed Feb. 13, 2015, the entirety of each of which is hereby incorporated by reference herein for all purposes and forms a part of this specification.

BACKGROUND

Field

This development relates generally to heart valves, in particular to devices, systems and methods for heart valve replacement.

Description of the Related Art

Mitral valve disease is typically repaired via invasive surgical intervention or by complicated pinching of the leaflets together creating dual, smaller openings or a mitral valve replacement excluding the native valve. The surgical approach involves risky by-pass surgery, including an opening into the patient's chest and heart chambers to expose the mitral valve for direct viewing and repair. Resection and partial removal of the patient's leaflets along with the implantation of a surgical ring like a Carpentier-Edwards Physio, produced by Edwards Life Science, are conventional but complex techniques used by surgeons to reduce the diameter of the patient's mitral annulus, thus allowing the leaflets to properly coapt and reducing the mitral regurgitate flow. The E-valve catheterization device described in U.S. Pat. No. 7,736,388 B2 and recently approved in the U.S. attempts to duplicate a surgical technique developed by Dr. Ottavio Alfieri where a connection is made across the mitral valve creating dual openings totaling a smaller cross sectional area for blood to flow. This technique often slightly reduces the regurgitate flow but does not provide as durable a solution as the surgical ring implantation. Thus, solutions to mitral valve disease without these drawbacks are needed.

SUMMARY

The current device may be used as a heart valve replacement. The device includes an implantable frame coupled with a valve comprising one or more valve leaflets. The device may replace a native mitral valve. The device may be delivered via catheterization, for example through a venous access in the groin and trans-septal puncture in the heart accessing the left atrium. The device may be delivered in a collapsed configuration and exposed in the left atrium for expansion.

The device may include a closed-shape frame defining an axis therethorugh, with a first side and a second side opposite the first side generally in the axial direction, with a skirt, such as a flared edge, coupled with an end of the frame. The skirt may be a flared edge or edge portions of the frame. The frame may expand. The implantable frame may be coupled with, for example attached to, one or more valve leaflets. The leaflets may be tissue, polymer or other suitable materials. In some embodiments, the leaflets may be coupled with the frame utilizing suturing techniques.

The device may include one or more anchors coupled with the frame. The anchors may be elongated rods with piercing features on an end of one or more of the anchors. The anchors may be located circumferentially about the periphery of the frame, for example from the distal or proximal end of the frame. Positive securement of the frame within the mitral valve may be achieved with the anchors engaging native tissue, such as the native valve annulus. The anchors may follow a straight path, a curved path, or combinations thereof, when engaging or engaged with the tissue. The anchors may follow the path of the skirt, such as a flared edge, when engaging or engaged with tissue.

The device may include one or more seals. The seal, such as a barrier, ring, cuff or toroid, may be included, for example to prevent leakage around the valve and/or to aid in securement of the implanted frame.

In one aspect, an implantable heart valve device is disclosed. The device comprises a tubular frame having a proximal end, a distal end and a central lumen extending therethrough, with the frame comprising at least a first pair of adjacent struts joined at a proximally facing apex, and at least a second pair of adjacent struts joined at a distally facing apex. The device further comprises a plurality of distally facing anchors coupled with the frame and configured to embed into tissue surrounding a native mitral valve, a valve coupled with the frame to regulate blood flow through the central lumen, a moveable restraint coupled with the frame and configured to restrain the frame at a desired width and an annular seal carried by the frame, for inhibiting perivalvular leaks.

In some embodiments, the annular seal comprises a barrier. The barrier may be located on the interior of the frame. The barrier may be located on the exterior of the frame.

In some embodiments, the annular seal comprises a cuff. The cuff may be inflatable.

In some embodiments, the annular seal comprises an axially extending barrier and an outwardly radially extending ring.

In some embodiments, the leaflets comprise pericardial tissue.

In some embodiments, the device further comprises a plurality of connectors, for connecting the valve to the tubular body.

In some embodiments, the restraint comprises an aperture for receiving the first pair of adjacent struts. The restraint may comprise a collar. The collar may comprise a threaded surface. The first pair of adjacent struts may comprise a threaded surface.

In some embodiments, the restraint comprises a loop carried by the tubular body and surrounding the central lumen. The restraint may be configured to reversibly adjust the implant body radially within a working range.

In some embodiments, advancing the collar in an axial direction reduces the angle between the first pair of struts thereby reshaping the implant body.

In some embodiments, the anchors are each rotatably carried by the body.

In some embodiments, the anchors are configured to be retractable.

In some embodiments, the implant body is configured to be reshaped such that a diameter at the proximal end is different from a diameter at the distal end.

In some embodiments, the restraint is slidable axially along the first pair of struts.

In some embodiments, at least one of the plurality of anchors has a helical shape and rotating the anchor causes the anchor to extend into the tissue.

In some embodiments, the device comprises at least four pairs of adjacent struts and at least four apexes. The device may comprise at least four restraints. The device may comprise at least four anchors.

In some embodiments, rotation of the anchors axially displaces the anchors with respect to the body.

In some embodiments, each strut in an adjacent pair of struts comprises a threaded surface.

In some embodiments, the valve comprises at least a first leaflet and a second leaflet. The first and second leaflets may be different sizes to selectively direct the direction of blood flow exiting the valve. The valve may further comprise a third leaflet, wherein the first leaflet is larger than both the second and third leaflets. The first leaflet may be located on the anterior side of the valve.

In some embodiments, the distal end of the body comprises a skirt that flares outward away from the lumen. The skirt may flare outward and distally.

In some embodiments, the distal end of the body comprises a skirt that flares outward and proximally.

BRIEF DESCRIPTION OF THE DRAWINGS

Elements in the figures have not necessarily been drawn to scale in order to enhance their clarity and improve understanding of these various elements and embodiments described herein. Furthermore, elements that are known to be common and well understood to those in the industry are not depicted in order to provide a clear view of the various embodiments described herein, thus the drawings are generalized in form in the interest of clarity and conciseness.

FIGS. 8A-B are various views of embodiments of a heart valve device with a valve having different sized and shaped leaflets configured for re-direction of blood flow exiting the device.

FIGS. 8C-8D are side views of the devices of FIGS. 8A and 8B showing embodiments of re-directed flow exiting the devices.

FIG. 9 is a partial side view of an embodiment of a heart valve device showing an interface between a frame and anchor, including a coil surrounding a central spike.

FIGS. 14A-14B are partial side views of an embodiment of a heart valve device showing a frame with a closure system including a threaded portion and corresponding moveable restraint embodied as a collar.

FIGS. 24A-24B are partial perspective views of an embodiment of a balloon-based delivery and shaping system for delivering and shaping, for example ovalizing, the various heart valve devices described herein.

DETAILED DESCRIPTION

In the following discussion that addresses a number of embodiments and applications, reference is made to the accompanying drawings that form a part hereof, and in which is shown by way of illustration specific embodiments in which the embodiments described herein may be practiced. It is to be understood that other embodiments may be utilized and changes may be made without departing from the scope of the disclosure.

Various inventive features are described below that can each be used independently of one another or in combination with another feature or features. However, any single inventive feature may not address all of the problems discussed above or only address one of the problems discussed above. Further, one or more of the problems discussed above may not be fully addressed by the features of each embodiment described below.

Various embodiments of a heart valve device are described. Related delivery and/or deployment systems are also described. The device may include an expandable frame with anchors to secure the device to native heart tissue. The anchors may be aligned with an axis defined by the frame and/or angled with respect to such axis. The frame may expand and/or be shaped to securely position within a native heart valve annulus, such as the native mitral valve annulus. For instance, the frame when expanded may have a flared end or skirt that facilitates with secure positioning of the device in the heart. The device may also include a barrier for directing blood flow. The device may include a seal to prevent leakage of blood around the device. These are some of the features of the device and systems described herein.

Figure 1A:
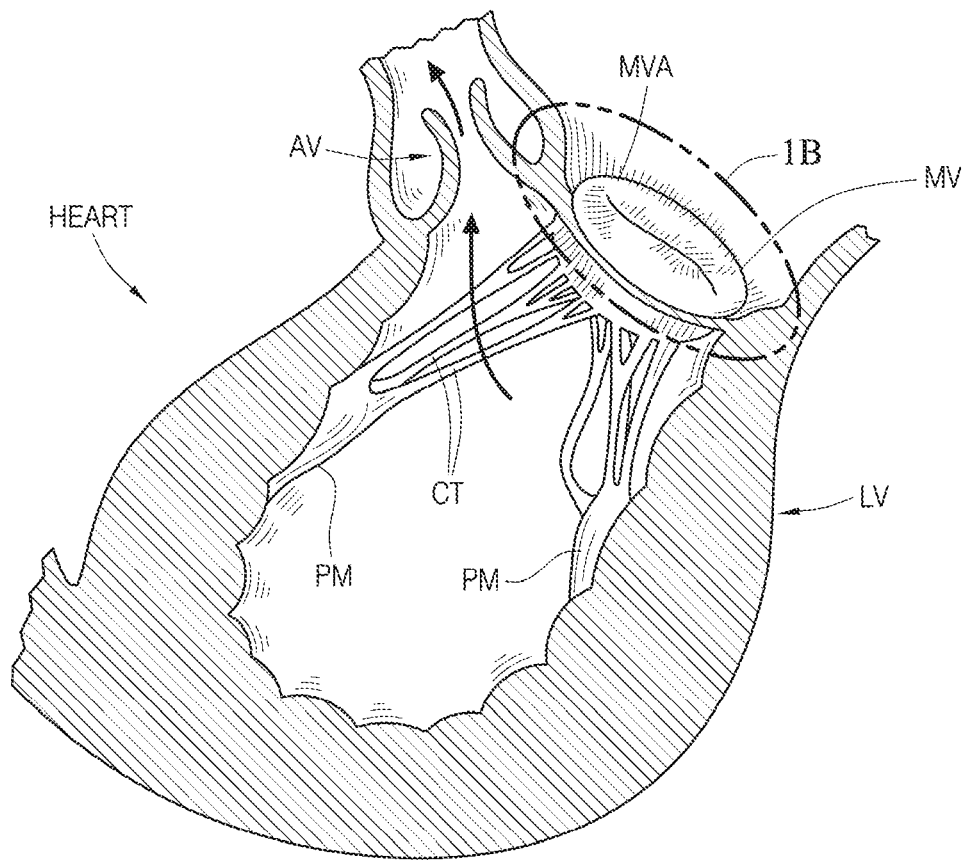
FIG. 1A is a partial cross-section view of the native mitral valve anatomy of a human heart and surrounding features.
Figure 1B:
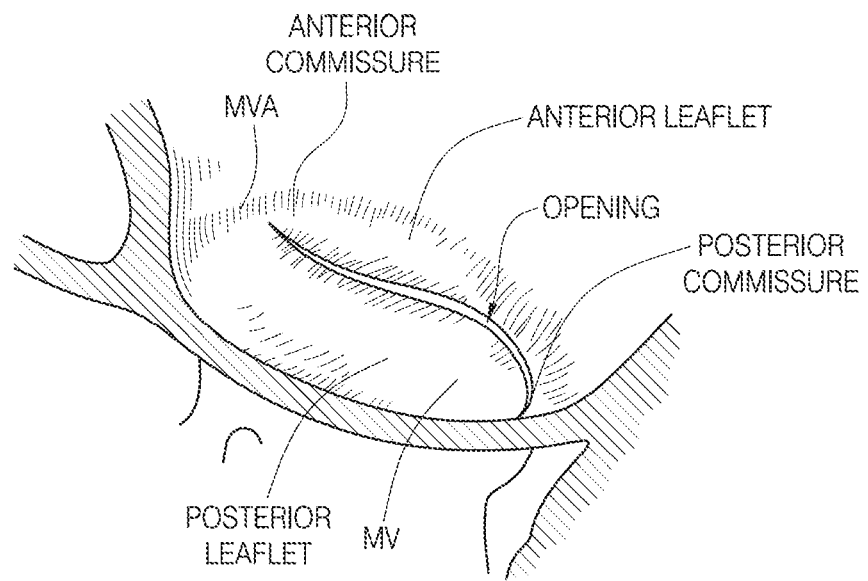
FIG. 1B is a detail view of the native mitral valve of FIG. 1A.

FIG. 1A is a partial cross-section view of the native mitral valve MV and left ventricle LV of a human heart. FIG. 1B is a detail view of the native mitral valve MV of FIG. 1A. The mitral valve MV connects the left ventricle LV and the left atrium (above the mitral valve MV). The mitral valve annulus MVA surrounds the mitral valve MV. The chordae tendineae CT extend from papillary muscle PM of the wall of the left ventricle LV to the leaflets of the mitral valve MV. The aortic valve AV is downstream of the mitral valve MV. During diastole of the left ventricle LV, the mitral valve MV opens to allow blood flow from the left atrium (above the mitral valve MV), through the mitral valve MV, and into the left ventricle. The aortic valve AV closes to prevent blood flow from exiting the left ventricle during ventricular diastole. During ventricular systole, the mitral valve MV closes and the aortic valve AV opens to allow blood flow from the left ventricle, through the aortic valve AV and into the aorta (above the aortic valve AV).

As shown in FIG. 1B, the mitral valve MV includes an anterior leaflet and posterior leaflet surrounding the opening. The opening is surrounded by the mitral valve annulus MVA, a fibrous ring. The two leaflets are joined at an anterior commissure at one end of the opening and a posterior commissure at the opposite end of the opening.

Figure 1C:
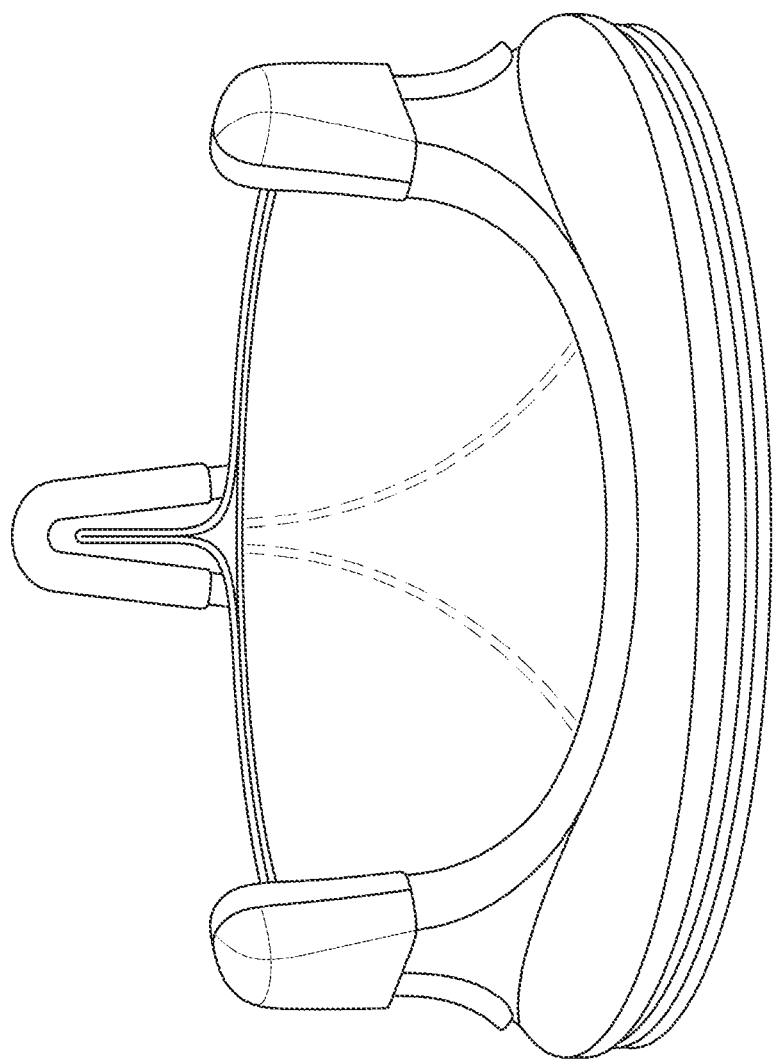
FIG. 1C is a perspective view of a prior art tri-leaflet valve.

FIG. 1C is a perspective view of a prior art tri-leaflet valve. The tri-leaflet valve is similar to one that would be inserted into a collapsible frame.

Figure 2:
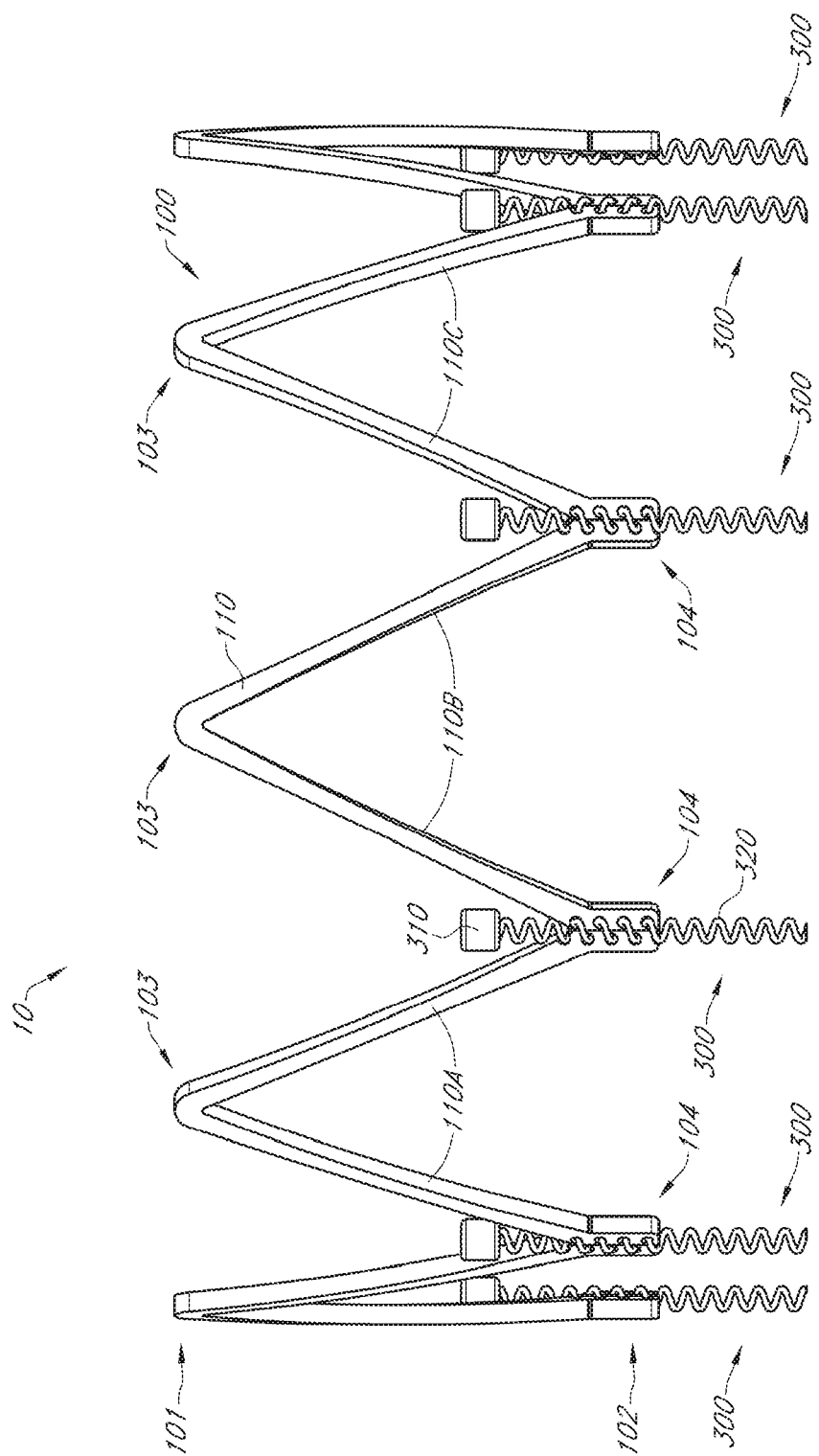
FIG. 2 is a partial side view of an embodiment of a heart valve device including embodiments of a frame and distally extending anchors.

FIG. 2 is a partial side view of an embodiment of a heart valve replacement device 10 having distally extending anchors 300. The device 10 may include an expandable frame 100. In some embodiment, the device 10 may include a valve 200 (see, for example FIG. 5). The valve 200 may be comprised of tissue leaflets coupled with the frame 100. The device 10 may have one or more distally extending anchors 300 coupled with a distal end 102 of the frame 100 for securing the frame 100 and/or valve 200 within the native annulus. The device 10 may include anti-backout features to secure the device in place, such as a skirt 150 formed from a flared frame 100 end. Alternatively or in addition, the device 10 may have a variety of other securement features, such as anti-counter rotation anchors 300, curved-path anchors 300, or outwardly extending/angled anchors 300, as described herein.

The frame 100 may include a proximal end 101 and a distal end 102 that is opposite the proximal end 101. When implanted, the device 10 may be oriented such that the proximal end 101 may be closer to the left atrium, and the distal end 102 may be closer to the left ventricle.

In some embodiments, the frame 100 may be tubular between the proximal end 101 and the distal end 102. Tubular includes any generally rounded, closed shape. For example, the frame 100 may be circular or non-circular, as described herein. The frame 100 may have a variety of shapes, for example "D"-shaped, oblong, oval, etc., as described herein. The shapes may be chosen in order to match a patient's anatomy.

The frame 100 may include a body 110. The body 110 may be a tubular structure. The body 110 may define a central lumen extending therethrough between the proximal and distal ends 101, 102. In some embodiments, the body 110 may be formed primarily from one or more wires or segments. The wires or segments may have a variety of cross-sectional configurations, for example round, flat, polygonal, segmented, smooth, sharp, increased area, reduced area, other suitable configurations, or combinations thereof. The wire or segments may form a series of struts of the frame 100.

The body 110 may include the struts 110A, 110B, 110C, as shown in FIG. 2. For clarity, other struts in FIG. 2 are not labelled. The frame 100 may include one or more apexes, which may be formed by adjacent pairs of struts. Each strut in an adjacent pair of struts may comprise a threaded surface, as described herein. As shown, there may be one or more proximal apexes 103 located on the proximal end 101 of the frame 100 and formed, for example, by proximal vertices of the struts 110A, 110B, 110C. There may be one or more distal apexes 104 located on the distal end 102 of the frame 100 and formed, for example, by the struts 110A and 110B, 110B and 110C, etc. For clarity, not all apexes 103, 104 are labelled. There may be at least four pairs of adjacent struts and at least four apexes.

The body 110 may be separate portions coupled together. For instance, the frame 100 may be constructed from a plurality of portions of the body 110, such as one or more struts 110A, 110B, 110C, coupled together. As shown in FIG. 2, adjacent struts may be coupled together by one of the anchors 300. For instance, the strut 110A may be coupled with the strut 110B via an anchor 300. Similarly, the strut 110B may be coupled with the strut 110C via another anchor 300. The remaining struts of the frame 100 may be similarly coupled together.

In some embodiments, the frame 100 may include openings for coupling the frame portions together. As shown, the strut 110A and strut 110B include openings for a shared anchor 300 to extend through the openings in a rotational path. Other struts may be similarly coupled. The body 110 may also be formed by coupling together separate portions through welding, fusing, pins or screws to construct the frame 100.

In some embodiments, the body 110 may be integral. For example, the body 110 may be formed from the same, monolithic piece of material. In some embodiments, the body 110 may be partially integral. For example, the body 110 may be formed from several strut collections coupled together, with each strut collection including several integral struts. The anchors 300 may be coupled with an integral or partially integral body 110 as described above with respect to a frame 100 composed of separate portions coupled together.

The anchors 300 may include a body 320 and head 310. The body 320 may extend along the length of the anchor 300. The body 320 may include a piercing end, such as a sharp tip, to pierce and engage tissue. The body 320 may be a coiled configuration as shown. The head 310 may be located on the opposite end of the anchor 300 as the piercing tip. The head 310 may include features for engaging the anchor 300 with a tool, for example for movement of the anchor 300 into tissue to secure the device 10 in place, as further described herein. The anchors 300 may be coupled with the distal end 102 of the frame 102 and extend distally from the distal end 102, as shown in FIG. 2.

As shown in FIG. 2, the frame 100 may be generally cylindrical in the expanded and/or contracted configuration. The proximal and distal ends 101, 102 may generally align with the struts and/or generally along an axis defined by the frame 100. The anchors 300 may thus extend generally axially and/or in a similar plane as the frame 100. The anchors 300 may thus extend through the frame 100, as described, and extend generally parallel to the axis. Thus, the frame 100 and anchors 300 may generally define a cylinder or other extended, tubular three-dimensional volume.

In some embodiments, features of a percutaneous aortic valve frame may be included, for example as described in U.S. patent application Ser. No. 12/986,780 to Rowe, filed Jan. 7, 2011, the entire content of which is incorporated herein by reference. In some embodiments, features for an adjustable endolumenal mitral valve 200 ring may be included, for example as described in U.S. patent application Ser. No. 14/562,554 to Lashinski, filed Dec. 5, 2014, the entire content of which is incorporated herein by reference.

The frame 100 may be formed from a variety of materials, including but not limited to stainless steel, cobalt chromium, Nitinol, Nitinol alloy, other suitable implantable or implant grade materials, or combinations thereof. The frame 100 may be constructed from a malleable material. The device may be radiolucent, such that the device expansion can be monitored via X-ray or fluoroscopy. Additional markers may be added for better visualization throughout the frame 100.

The frame 100 may have uniform thickness. In some embodiments, the struts 110A, 110B, 110C may have varying thicknesses and/or widths, for example to increase stillness or suppleness in areas of stress. An approximate wall thickness for a tubular frame 100 may be from about 0.20 to about 1.00 millimeters in thickness. The strut 110A, 110B, 110C width may be from about 0.20 millimeters to about 1.00 millimeters. In some embodiments, the strut 110A, 110B, 110C may be about 0.50 millimeters thick. In some embodiments, the strut 110A, 110B, 110C may be about 0.75 millimeters in width. In some embodiments, a variable thickness radially and/or longitudinally may be implemented, for example to allow for a differential stiffness throughout the frame 100. The thickness or thicknesses of the frame 100 may be achieved by machining, such as grinding, select areas of the frame 100 material, such as the body 110 or struts 110A, 110B, 110C.

The frame 100 may have a variable surface topography, including but not limited to surface contours, surface finishes, surface coatings, etc. The desired topography may be accomplished by surface grinding selective areas of the frame 100. The frame 100 may be electropolished, for example after construction of the frame 100, for a smooth, passivated surface reducing adverse tissue interactions or reactions to elements of the alloy. These and other methods may also be used to implement the desired thicknesses, as discussed above.

In some embodiments, construction of the frame 100 may include laser cutting a pattern in a small tube to define a predictable expansion geometry. Elements of the tubular frame 100 may be removed via cutting laser, such as a Nd:YAG or CO2 laser. For instance, a diamond or sinusoidal pattern may be implemented, for example to allow for expansion and contraction for implantation and delivery. Holes may be drilled into the frame 100 for attaching of attachment features, for example for passing suture therethrough to attach tissue and/or anchors 300, as further described herein.

The frame 100 may be configured to expand. In some embodiments, the frame 100 may be configured to expand via shape memory. For example, the frame 100 may be constructed from a Nitinol alloy and heat-set to a preferred diameter or shape, thus reducing or eliminating the need for a mechanical means for expansion within the deployment site.

In some embodiments, the frame 100 may be configured to mechanically expand. For example, the frame 100 expansion may involve actuation. In some embodiments, the frame 100 may be configured to fluidly expand. For example, the frame 100 expansion may involve hydraulic means. In some embodiments, the frame 100 may expand via a combination of mechanical, fluid, and/or other means. For instance, the frame 100 expansion may be via a balloon or linkage to provide an internal, radial force moving the frame 100 from a collapsed configuration to an expanded configuration. Further detail of frame expansion features are provided herein, for example with respect to FIGS. 22A-25B.

The frame 100 may have a non-uniform expansion. Non-uniform expansion of the frame 100 may be designed into the cut pattern. In some embodiments, a non-uniform frame 100 geometry may result, for example for a better fit for each patient. For instance, an elliptical pattern may better fit the mitral valve anatomy, such as the annulus shape, of a particular patient. The eliptical resulting shape may allow, for example, for a preferential final shape, which may be more similar to a GeoForm annuloplasty ring where the Anterior-Posterior dimension is narrower than the Septal-Lateral dimension. In some embodiments, a vertical, geometrical undulation in the device, for example the valve 200 leaflets, may be included, for example to help moving the leaflets to a normal coaptation by raising the posterior leaflet up and in from its fallen and dilated diseased position.

The frame 100 may include various drug eluting features, such as coating applied to the frame 100. The drugs may prohibit or inhibit healing responses of tissue. Such features may include Heparin, thin-film polymer, drug eluting, hydrophilic type, or other suitable coatings or combinations thereof. The coatings may be loaded with a host of drugs and anti-inflammatory agents for proper healing. Pockets, holes or wells may be included in for example cut into, the frame 100, to form space for loading drugs or coatings for elusion into the surrounding area in the body.

The device 10 may include one or more of the anchors 300. There may be at least four anchors, 300. There may be fewer or more than four anchors 300. The anchors 300 may rotate. The anchors 300 may each be rotatably carried by the frame 100. Rotation of the anchors 300 may axially displace the anchors 300 with respect to the frame body 110. The anchors 300 may be configured to penetrate tissue, resist bending and/or axial movement, and perform other necessary functions. The anchors 300 may be configured to be retractable. The device 10 may be located within the mitral valve 200 annulus and attached to native tissue via a plurality of anchors 300. The anchors 300 may be located around the frame 100, as described herein. The anchors 300 may secure the device 10 from movement relative to adjacent tissue and/or prevent leakage around the device 10. A variety of anchors 300 may be used to secure the device including for example a plurality of barbed spikes, as described herein.

In some embodiments, the anchors 300 may include a rotational screw, either clockwise or counterclockwise. The anchors 300 may be constructed of a wire body 320, such as round, elliptical, rectangular, other suitable wire, or combinations thereof. The anchors 300 may be polished smooth, may have surface irregularities for example to limit rotation in one direction or both, other suitable features, or combinations thereof. The rotational anchors 300 may be constructed of stainless steel, cobalt chromium, polymers, other suitable implantable or implant grade material, or combinations thereof.

The anchors 300 may be coil-shaped, helical, and the like. The helical anchors 300 may be constructed from a wire body 320 having a cross-sectional diameter from about 0.2 millimeters to about 1.0 millimeters. In the coiled configuration, the anchor may have a "coiled diameter" from about 1.0 millimeters to about 3.0 millimeters. The coiled diameter refers to a length approximately equal to the distance across the resulting coil shape formed by the coiled wire as measured perpendicular to an axis defined by the coil. The pitch of the coil may be from about ten threads per inch to about thirty-six threads per inch. The pitch may be constant along the length of the anchor. In some embodiments, the pitch may not be constant along the length of the anchor. The axial length of the anchor, i.e. as measured along the axis, may be various suitable amounts. In some embodiments, the axial length may be from about 2 millimeters to about 10 millimeters. An alternative construction would be to cut a helical pattern into a coiled anchor 300 with similar construction as outlined above.

Figure 5:
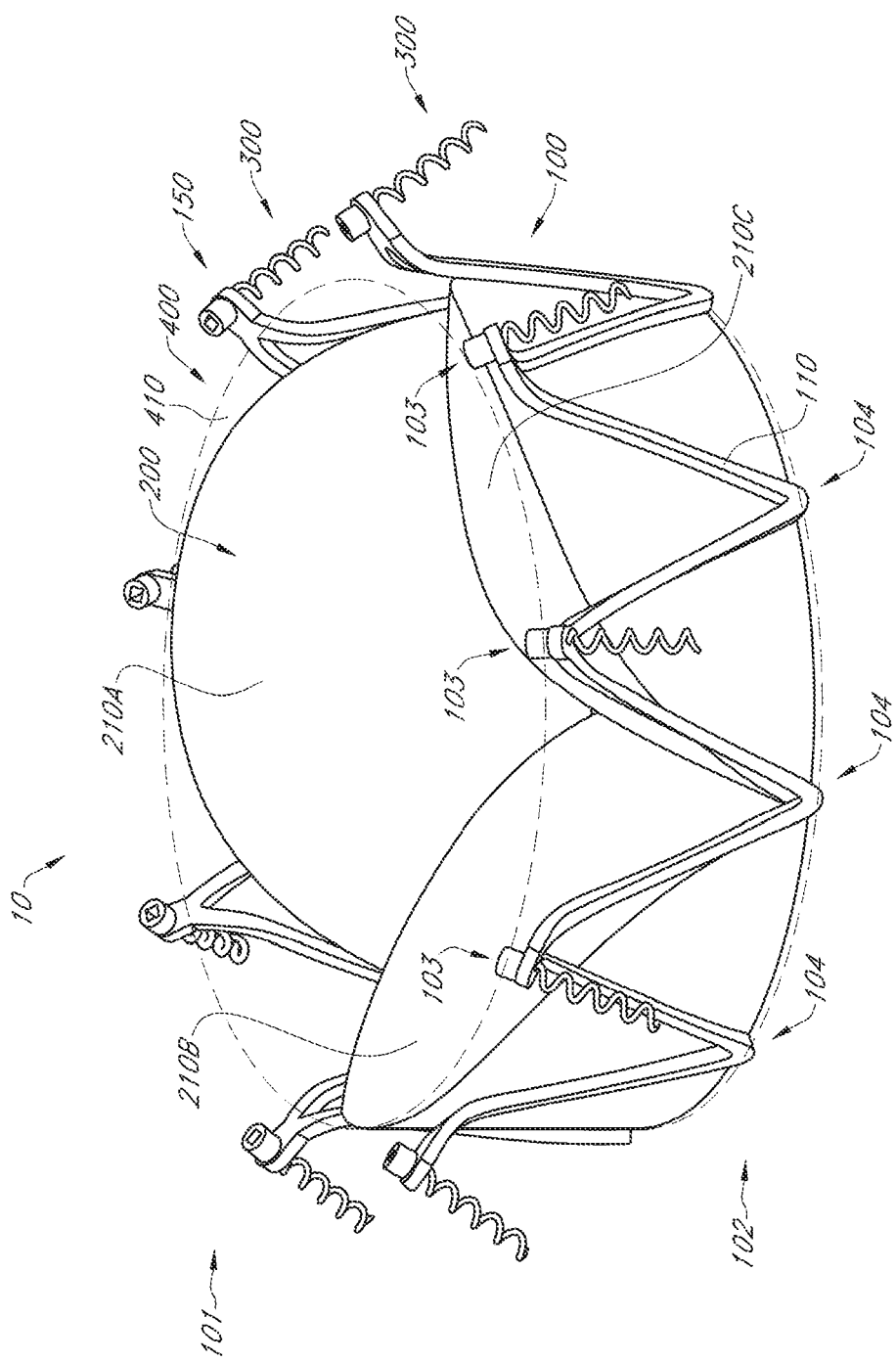
FIG. 5 is a perspective view of an embodiment of a heart valve device having a frame with a skirt, angled anchors, a mitral valve and an interior annular seal embodied as a barrier.
Figure 7A:
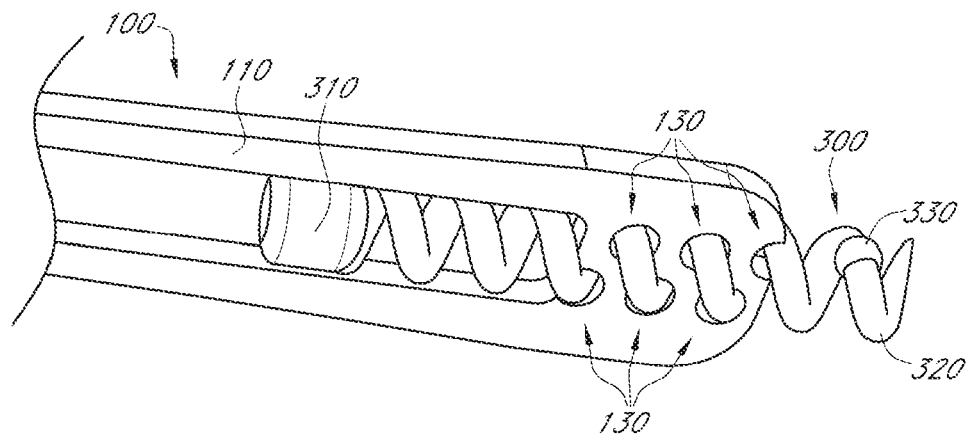
FIGS. 7A and 7B are partial perspective views of an embodiment of a heart valve device showing an embodiment of an interface between a frame and anchor.
Figure 7B:
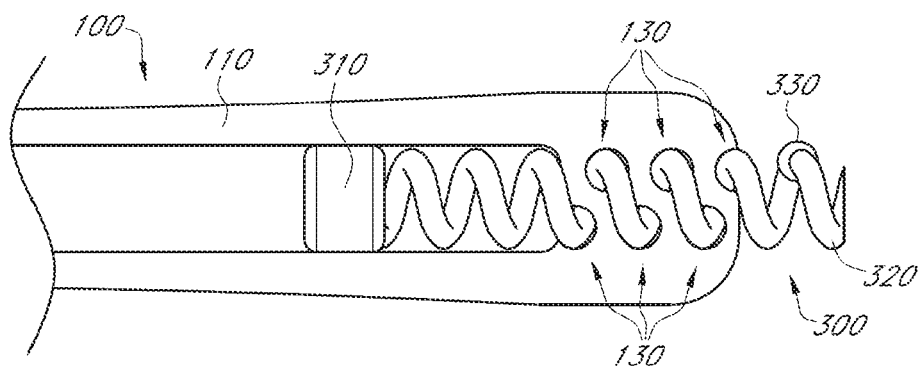

The anchors 300 can be threaded into the frame 100 via openings 130, such as holes, to pass the anchor through, as discussed in further detail herein, for example with respect to FIGS. 7A-7B. In some embodiments, the frame 100 may have a single through-hole connection allowing the anchor 300 to rotate freely and move laterally within the hole. In embodiments having the anchor 300 and frame 100 with through-holes, for example as shown in FIGS. 3B and 5, the device 10 may draw the frame 100 closer to the tissue when engaged into the tissue and rotated.

Connecting and driving the anchors 300 can be accomplished via slotted element, hex driver or similar means. The connection and disconnection means could be pure slot and receiver, fracture-able joint or magnetic connection to hold the anchor 300 to a drive means such as a rotational shaft located outside the patient's body. The connections could be pre-attached and loaded for delivery or attached in the body reducing the cross sectional diameter by staggering the larger components longitudinally along a delivery catheter. See, for example, FIGS. 4A-4B.

In some embodiments, the anchor 300 may be a threaded rod with raised or cut threads into the periphery. The anchor 300 may function as a more stable element in the tissue resisting bending moments about the connection axis. The additional stiffness and material within the central axis may require additional rotational force to drive the anchor 300 into the tissue but would be a stronger point securement. Constructed from similar material as the coiled anchor 300, this shape and form could be tapered to ease penetration forces during insertion.

A surface modification to the anchor 300 may increase the holding force by resisting its counter rotational direction. Small barbs or surface nicks on the anchor 300 would resist a counter rotation and loosening of the anchor 300 after implantation. These surface modifications could be employed via chemical treatment or a mechanical force to cut or swage into the anchor 300.

The anchors 300 attaching the frame 100 to the surrounding tissue could be parallel to the frame's 100 central axis or angled outward to direct the anchor 300 into more substantial tissue. An angle from about five degrees to ninety degrees from the central axis may direct the anchors 300 into fibrous, myocardial tissue for additional strength and securement. The angles could change circumferentially depending upon the annulus tissue surrounding the anchor 300. Specifically, between the trigonal area near the aortic valve AV, the tissue is fibrous but thinner, and therefore a more acute angle could perform better and not penetrate the sinus of the aortic valve AV causing an unwanted leak. Conversely, opposite the trigonal area, a more obtuse angle would be beneficial due to the thicker, more vascularized tissue in this area. Also, a deeper anchor 300 would allow additional penetration into the softer tissue. These angular changes can be incorporated in a proximally located anchor 300 or distally located anchor 300 on the frame 100.

The anchor 300 positions may be variable along the height of the frame 100 to direct the angle of the device 10 and/or anticipate and accommodate the saddle shape of the native mitral valve's three dimensional shape.

The delivery of the device 10 may be via the femoral vein in the groin for a trans-septal entry into the left atrium and down into the mitral valve annulus MVA. The anchors 300 may be inserted into the annulus MVA from the left atrium (above the mitral valve). In some embodiments, delivery may be from a trans-apical entry, for example, where the anchors 300 may not be positioned in the left ventricle LV.

Figure 3A:
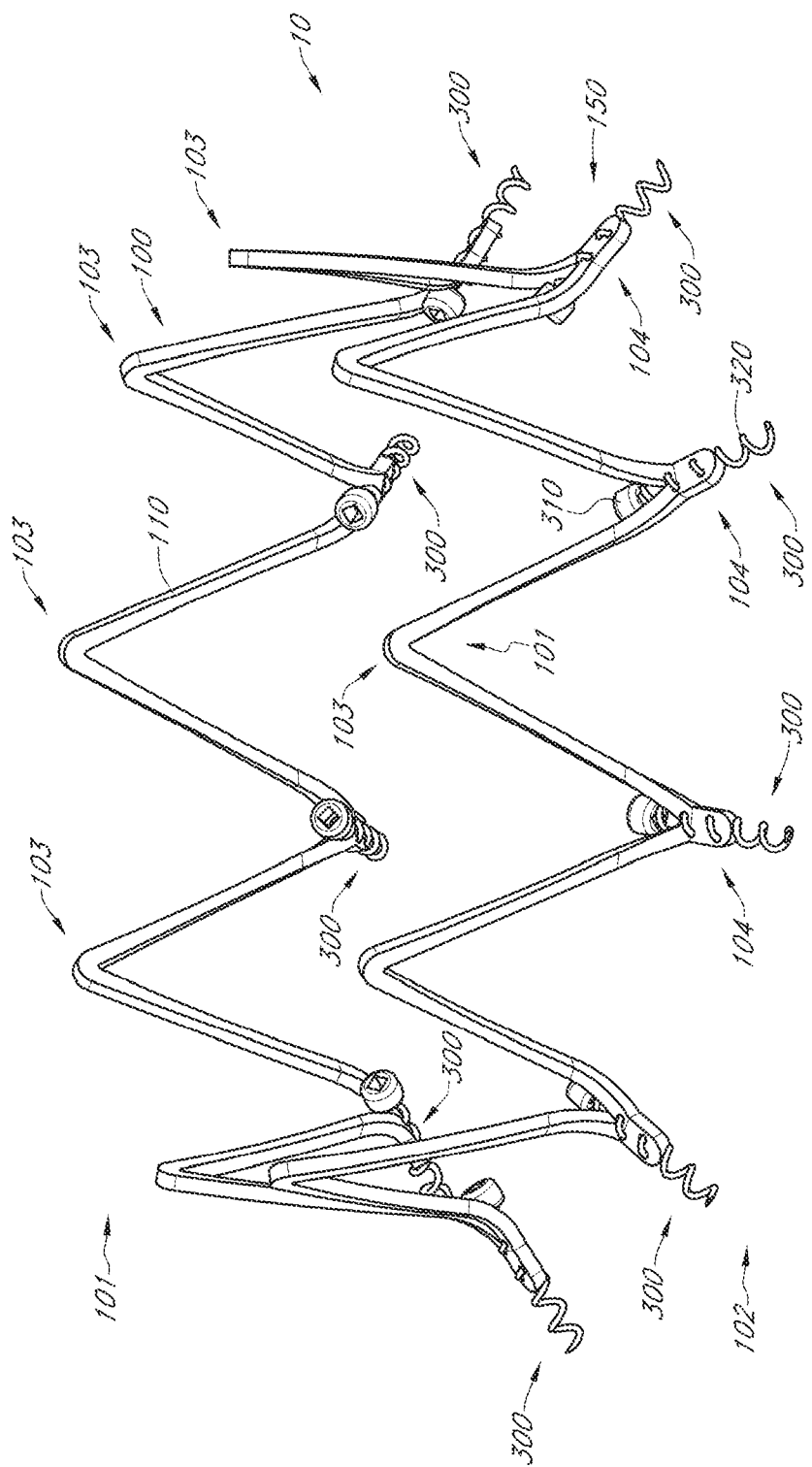
FIG. 3A is a perspective view of an embodiment of a heart valve device having embodiments of a frame with an angled skirt on a distal end and with distally and outwardly extending anchors located on a distal end of the frame.
Figure 3B:
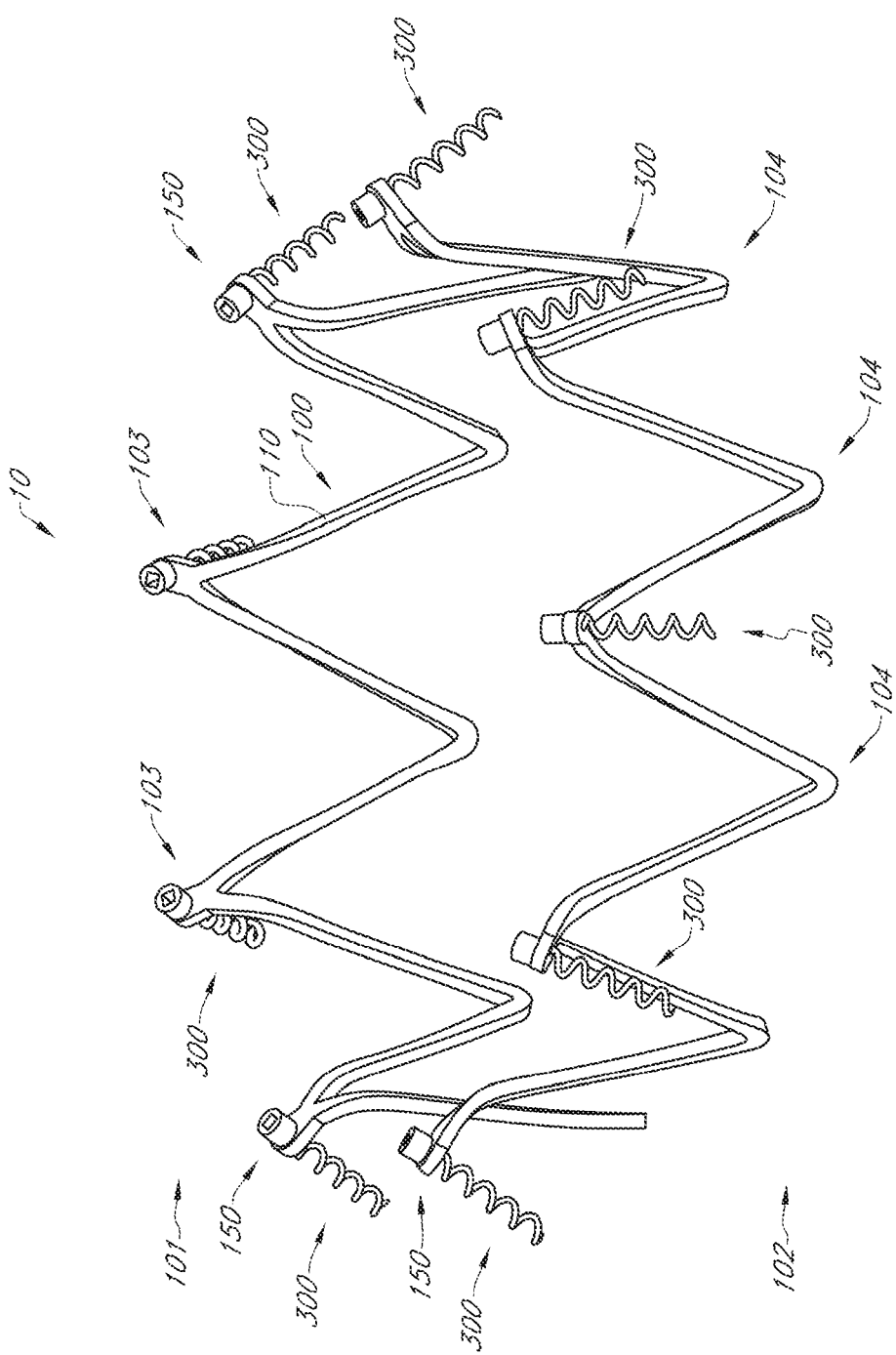
FIG. 3B is a perspective view of an embodiment of a heart valve device having embodiments of a frame with an angled skirt on a proximal end and with distally and outwardly extending anchors located on a proximal end of the frame.

FIG. 3A is a perspective view of an embodiment of the heart valve replacement device 10 having embodiments of the frame 100 with an angled distal end 102. The device 10 of FIG. 3A may have the same or similar features and/or functionalities as the device 10 described with respect to FIG. 2, and vice versa. As shown in FIG. 3A, the device 10 may include distally and outwardly extending anchors 300 located on a distal end of the frame. That is, the anchors 300 are oriented angularly with respect to an axis defined by the frame 100 and/or with respect to a plane defined by the generally tubular portion of the frame 100.

Figure 12:
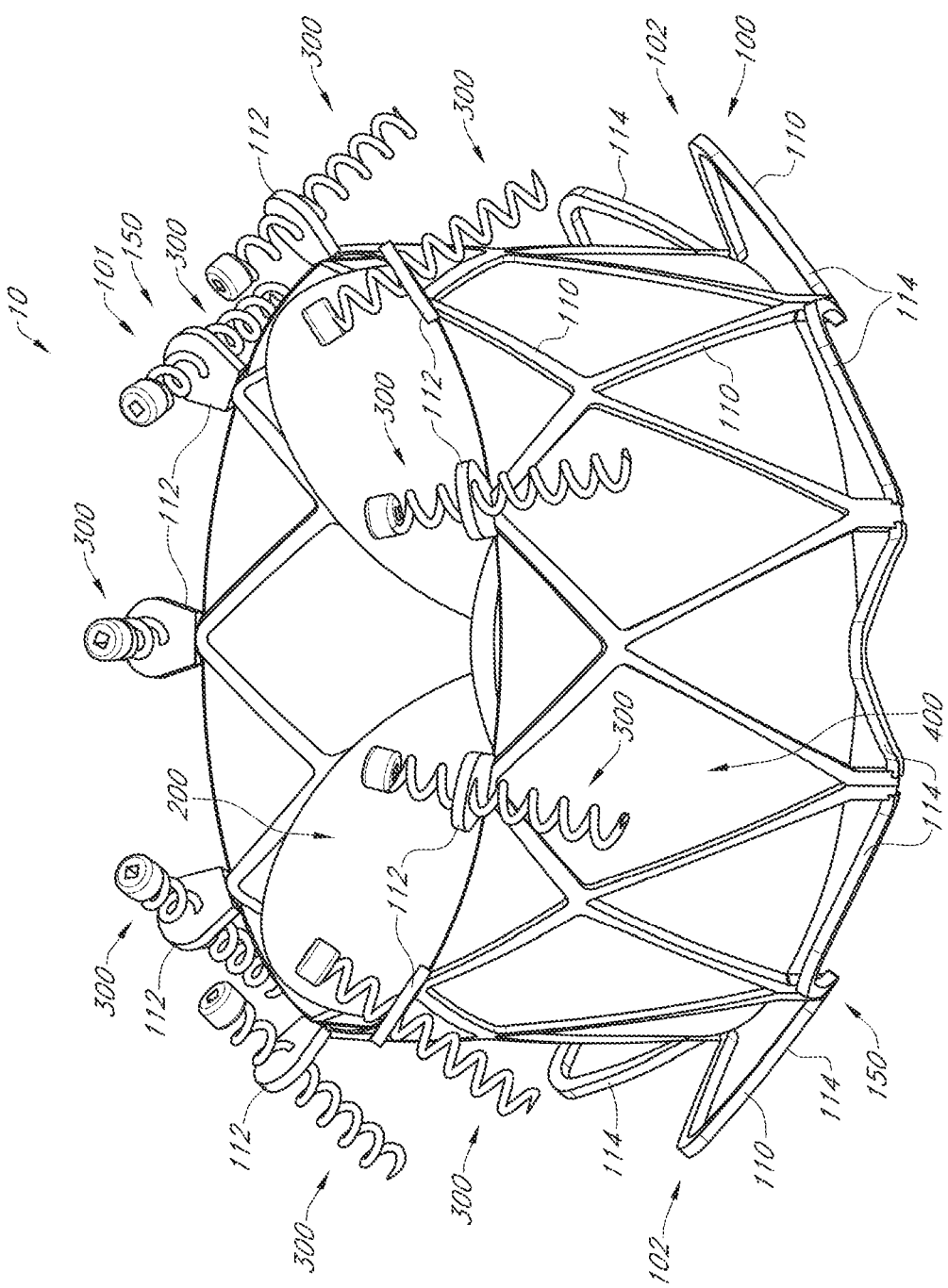
FIG. 12 is a perspective view of an embodiment of a heart valve device having an expandable frame with angled portions and a seal embodied as a barrier.

The frame 100 may have anti-backout features, such as the skirt 150. Such features may include the angled or flared distal end 102 of the frame 100 to trap the frame 100 within the valve 200 annulus from the left ventricle LV. This feature could be a bent portion of the lower laser cut pattern in the frame 100 and actuated at deployment or during the deployment phase, for example as shown in FIG. 12. This lower portion of the frame 100 could be angled in an upward direction toward the left atrium resisting movement during the closure of the valve 200. The blood pressure would act on the closed valve 200, for example during systole, providing a force in the direction of the left atrium. The flared lower frame 100 portion and/or the anchors 300 would resist this force from dislodging the frame 100 from its intended location.

FIG. 3B is a perspective view of an embodiment of the heart valve device 10 having embodiments of the frame 100 with an angled skirt 150 on the proximal end 101 with distally and outwardly extending anchors 300 located on the proximal end 101 of the frame. The device 10 of FIG. 3B may have the same or similar features and/or functionalities as other device 10 described herein, such as the devices 10 described with respect to FIGS. 2 and 3A, and vice versa. However, as mentioned, in FIG. 3B the proximal end 101 is flared to form the skirt 150. Further, the anchors 300 each extend through an opening at a vertex of the frame 100 at the proximal end 101. Such an arrangement may allow for implantation of the device 10 from within the left ventricle LV, as further described herein, for example, with respect to FIG. 18.

Figure 4B:
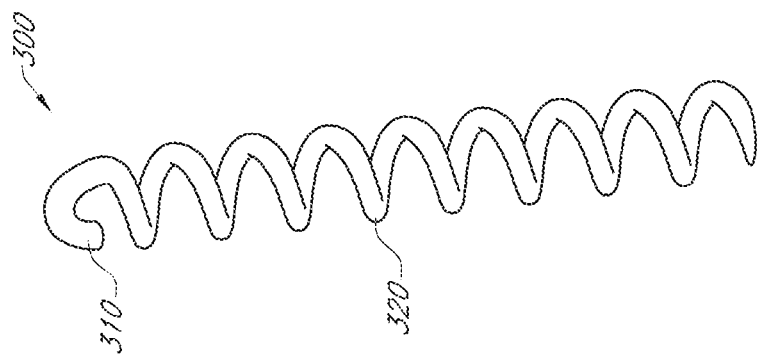
FIGS. 4A and 4B are perspective views of different embodiments of anchors that may be used with the various heart valve devices described herein.
Figure 4A:
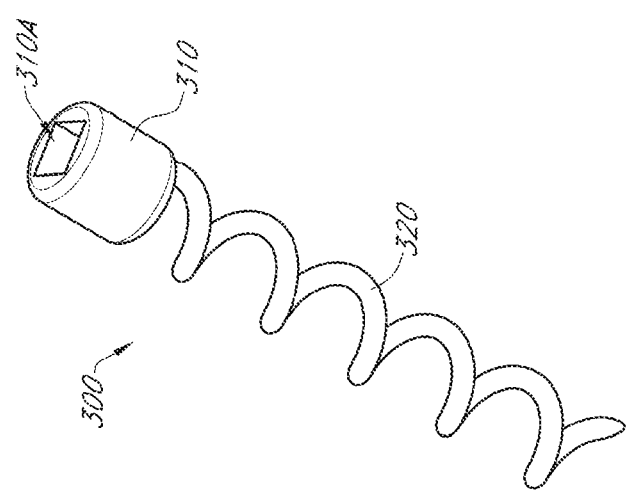

FIGS. 4A and 4B are perspective views of different embodiments of anchors 300 that may be used with the various heart valve devices 10 described herein. The anchors 300 may be rotated thus pulling the device 10 into intimate contact to the surrounding tissue securing it from movement. As shown in FIG. 4A, the anchor 300 may include the head 310 having a recess 310A defined therein. A complementary shaped tool, such as a square- or hex-head tool, may be received in the recess 310A for transmission of rotational forces from the tool to the anchor 300. As shown in FIG. 4B, the head 310 may be a generally flat or otherwise uncoiled portion of the anchor body 320 that may be grabbed or otherwise secured by a corresponding tool for similar rotation of the anchor 300.

FIG. 5 is a perspective view of an embodiment of the heart valve device 10 having a frame with the flared skirt 150, angled anchors 300, an implant mitral valve 200 and an interior annular seal 400 embodied as a barrier. The device 10 has the valve 200 attached into the frame 100, with integral anchors 300 at the proximal end 101 of the device 10 and the annular seal 400 to prevent leakage about the device 10. The valve 200 includes valve leaflets 210A, 210B and 210C. The valve leaflets 210A, 210B and 210C are attached along with the annular seal 400 to prohibit leakage about the device 10. The seal 400 may include the seal body 410. The body 410 may be a thin walled structure generally forming a sidewall of the seal 400. The seal 400 is shown attached to an interior side of the frame 100. The seal 400 is shown in dashed lines for clarity. In some embodiments, the seal 400 may be attached to an exterior side of the frame 100. In some embodiments, there may be an interior seal 400 and an exterior seal 400. The exterior seal 400 may have other configurations and embodiments, such as shown and described with respect to the woven barrier seal 400 of FIG. 11 or the inflated perivalvular seal 500 of FIGS. 12 and 13A-13C.

The device 10 may include an expandable, implantable frame 100 with tissue leaflets, such as leaflets 210A, 210B and 210C, coupled with, for example attached directly to, the frame 100. There may only be two leaflets. The device 10 may include a plurality of connectors, for connecting the valve 200 to the frame body 110. The mitral valve 200 may be shaped and defined by expanding the septal lateral dimension with a tool, for example to provide predictable space to place the device 10. This shaping may be defined with the frame 100 and allow intimate contact for placement of the anchors 300 in the surrounding tissue. A tool like a Kogan Endocervical Speculum may be used to spread the tissue in an open chest placement but the spreading device may need to be concurrent with the device 10 delivery and therefore be delivered via catheter using a similar means.

In some embodiments, the valve 200 may be tissue. Construction of the tissue valve 200 may include cross-linked pericardial bovine or porcine tissue to fixate the material. Examples of chemical fixative agents which may be utilized to cross-link collagenous biological tissues may include, for example, aldehydes (e.g., formaldehyde, glutaraldehyde, dialdehyde starch, para formaldehyde, glyceroaldehyde, glyoxal acetaldehyde, acrolein), diisocyanates (e.g., hexamethylene diisocyanate), carbodiimides, photooxidation, and certain polyepoxy compounds (e.g., Denacol-810, -512, or related compounds). For chemical fixatives, glutaraldehyde may be used. Glutaraldehyde may be used as the fixative for commercially available bioprosthetic products, such as porcine bioprosthetic heart valve (i.e., the Carpentier-Edwards® stented porcine bioprosthesis; Baxter Healthcare Corporation; Edwards CVS Division, Irvine, Calif. 92714-5686), bovine pericardial heart valve prostheses (e.g., Carpentier-Edwards® Pericardial Bioprosthesis, Baxter Healthcare Corporation, Edwards CVS Division; Irvine, Calif. 92714-5686) and stentless porcine aortic prostheses (e.g., Edwards® PRIMA Stentless Aortic Bioprosthesis, Baxter Edwards AG, Spierstrasse 5, GH6048, Horn, Switzerland).

In order to incorporate a tissue valve 200 with a stent or other type of frame 100, a number of different techniques and methods have been used, such as clamping, tying, gluing, or stitching, for example. However, many of the techniques used for this purpose generally produce a stented valve 200 that has concentrated stresses at the points where the leaflets are attached to the stent frame 100. That is, because the stents are relatively rigid as compared to the flexible material from which the leaflets of the tissue valve 200 are made, the repetitive flexing motion of the leaflets can create stress concentrations at the points where the tissue valve 200 is attached to the stent. These stress concentrations can eventually lead to tearing of the tissue, valve 200 leakage, and/or failure of the heart valve 200. The attachment points can also be sites for abrasion of the tissue that can lead to tearing of the tissue. Thus, the features described herein provide methods and devices for a durable attachment between a tissue valve 200 and frame 100 to distribute the stresses away from the attachment and seam areas and provide for nonabrasive contact surfaces for bioprosthetic heart valve leaflets.

Polymer leaflets could also be used to construct valve 200 leaflets 210A, 210B, 210C with polymers such as polyester, Teflon, urethane and could also be reinforced with strands of stronger materials to strengthen and improve fatigue resistance. Decell tissue anti-calcium treatment could also be added.

Figure 6A:
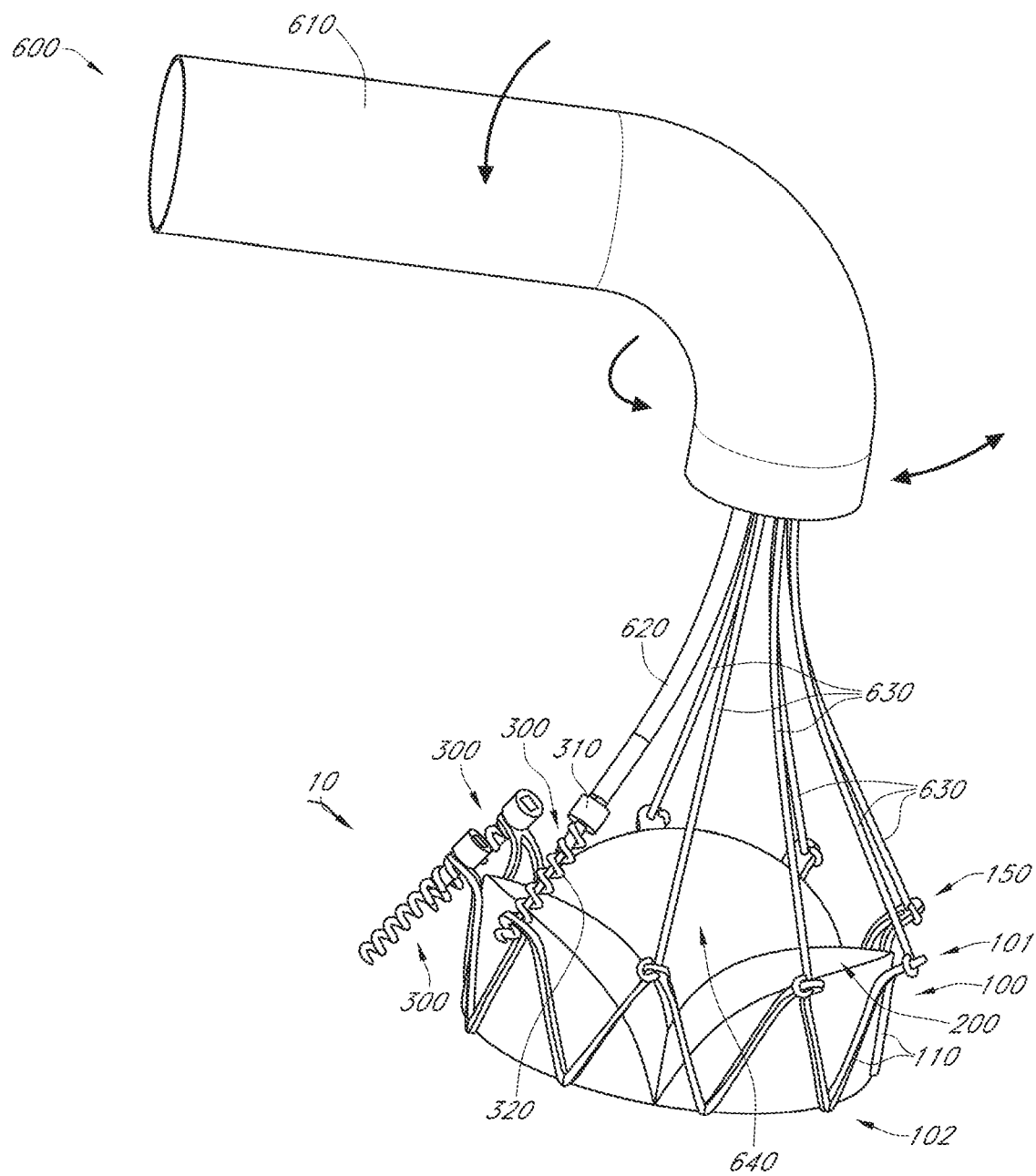
FIG. 6A is a partial perspective view of an embodiment of a delivery system for delivering and deploying the various heart valve devices described herein using a balloon.
Figure 6B:
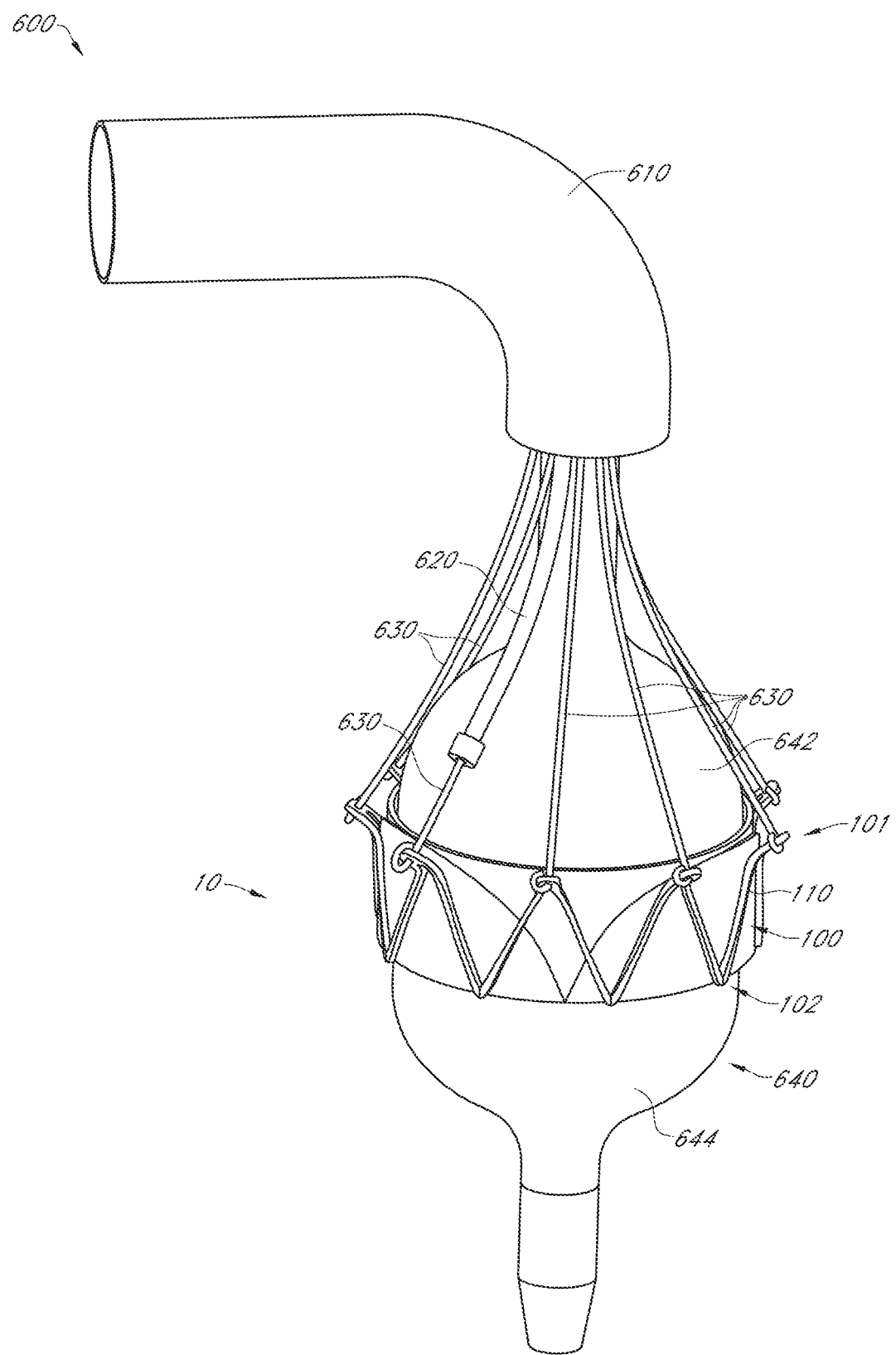
FIG. 6B is a partial perspective view of the system of FIG. 6A with the balloon expanded.

FIG. 6A is a partial perspective view of an embodiment of a delivery system 600 for delivering and deploying the various heart valve devices 10 described herein using a balloon 640. FIG. 6B is a partial perspective view of the system of FIG. 6A with the balloon 640 expanded. The device 10 may be attached to a steerable delivery system 600 and a central balloon 640 to expand the device 10 radially larger for proper size and positioning. The system 600 may include a delivery tool 610, which may include a catheter. For example, the system 600 may include a delivery catheter with a centrally mounted balloon 640 for frame 100 expansion and frame 100 connections to hold the device 10 in position during delivery and securement at or around the annulus. The balloon 540 may be expanded to include a first portion 642 located near the tool 610 and a second portion 644 located on the opposite side of the device 10. The system 600 may include one or more guides 620 for guidance of one or more delivery wires 630. The wires 630 may attach to the frame 100, for example at apexes of struts of the frame 100, such as the struts 110A, 110B, 110C. The wires 630 may attach to the proximal end 101 of the frame 100. The proximal end 101 may form the skirt 150, such as a flared end of the frame 100. The guide 620 may include and/or guide a driver for rotating or otherwise moving the anchors 300. The driver may couple with the head 310 of the anchors 300 to drive them into the tissue.

FIGS. 7A and 7B are partial perspective views of an embodiment of the heart valve device 10 showing an embodiment of an interface between the frame 100 and anchor 300. The body 110 of the frame 100 may include openings 130 where the coiled anchor body 310 is passed through to thread the anchor 300. The frame 100 may be formed from separate portions, such as struts, as discussed. Thus, the coiled anchor 300 may extend through openings 130 in adjacent frame 100 portions to join the two frame 100 portions together. In some embodiments, the frame 100 may be integral, as mentioned.

One or more of the anchors 300 may include one or more stoppers 330. Each anchor 300 could be assembled into the frame 100 and the stopper 330 at the distal end could be installed to resist the anchor 300 from becoming separated from the frame 100. The proximal portion would limit movement due to the drive head. The stoppers 330 may be located at the proximal and/or distal ends of the anchors 300. The stoppers 330 may limit rotational movement by means of a raised portion or changing the cross sectional shape of the helix.

Figure 7C:
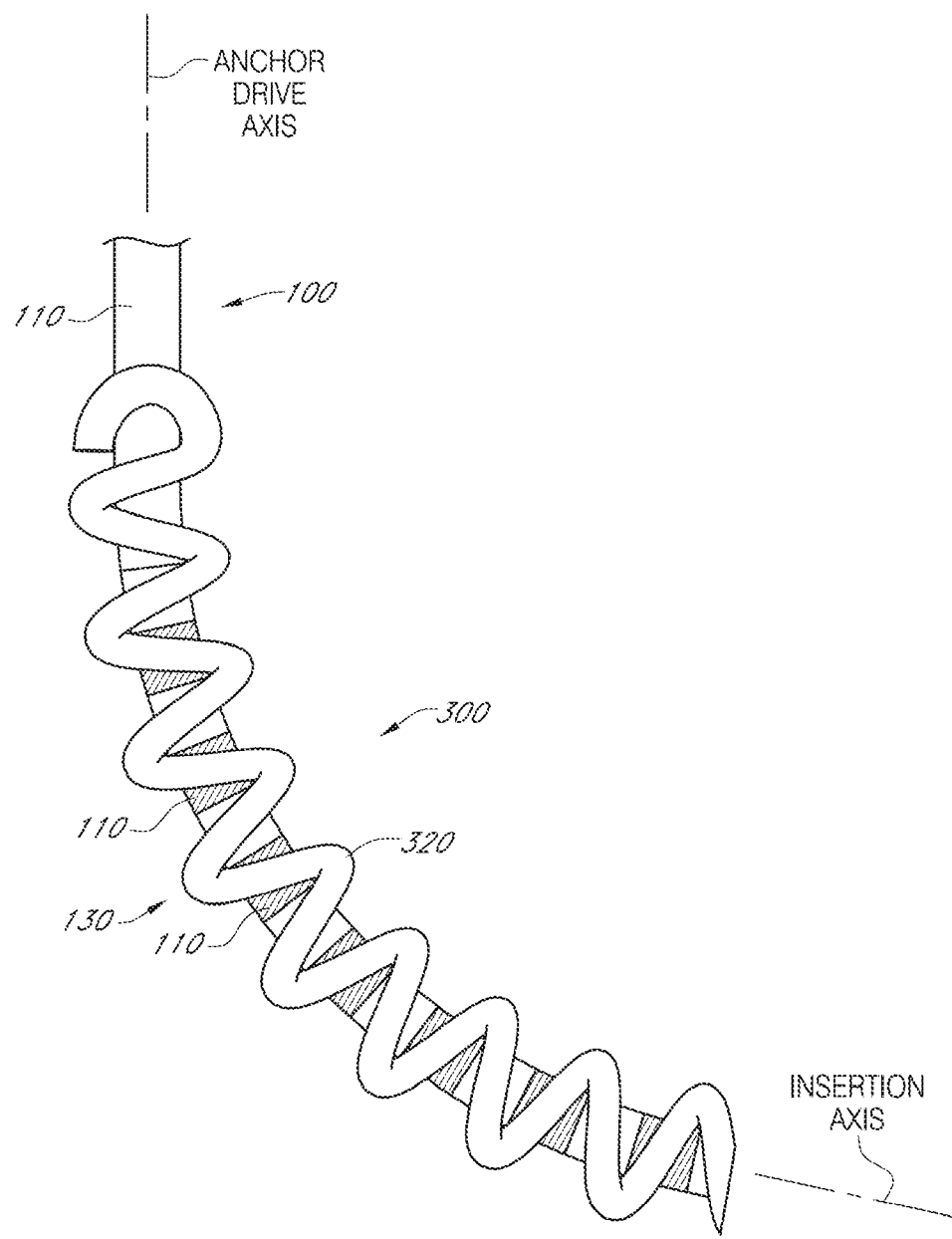
FIG. 7C is a partial cross-section view of a heart valve device showing an embodiment of a curved interface between a frame and anchor.

FIG. 7C is a partial cross-section view of the heart valve device 10 showing an embodiment of a curved interface interface between the frame 100 and anchor 300. This interface may be used with the various devices 10 described herein, for example with the skirt 150 of the device 10 discussed with respect to FIG. 3A. As shown in FIG. 7C, the frame 100 portion with openings 130 is shown in cross-section for clarity. As shown, a curved or angled coil body 320 of the anchor 300 follows a curved path. This may allow, for example, to direct the rotational drive axis in a different direction or plane than the insertion axis. The rotational or delivery drive axis refers to the direction of the tool used to drive the anchor 300. The insertion axis refers to the direction in which the anchor 300 is inserted into tissue. This may be helpful, for example, to drive in the same axis as the delivery tool yet force the anchors along a different, secondary axis or direction. Thus, to ease delivery of the anchors 300, a portion of the frame 100, such as the skirt 150, to hold the coiled anchors 300 may be curved or angled to change the driving direction with respect to the tissue insertion direction. The anchor 300 may thus be a flexible member directed through the series of openings 130 in the frame 100. Alternatively, a tubular member could redirect or angle the coiled anchor 300 in various directions. The rotational/delivery axis and the insertion axis could vary from about five to about ninety degrees from the axis of the annulus of the native mitral valve and/or device 10. In some embodiments, the rotational/delivery axis and the insertion axis could vary about forty degrees from the axis of the annulus of the native mitral valve and/or device 10.

FIGS. 8A-8F are various views of embodiments of the heart valve device 10 with the valve 200, for example the valve leaflets, configured, for example sized and/or shaped, for re-direction of blood flow exiting the device 10. The native mitral valve directs the flow of blood toward the posterior wall of the left ventricle LV aiding in the conservation of the momentum of the blood, aiding the efficiency of the heart. Conventional surgical valves used in the mitral annulus do not include this efficiency, as the blood flow is directed into the middle of the left ventricle LV. Therefore, in some embodiments, the device 10 described herein directs the blood flow through the implanted device 200 in a way that reproduces the blood flow path of the native mitral valve.

Figure 8A:
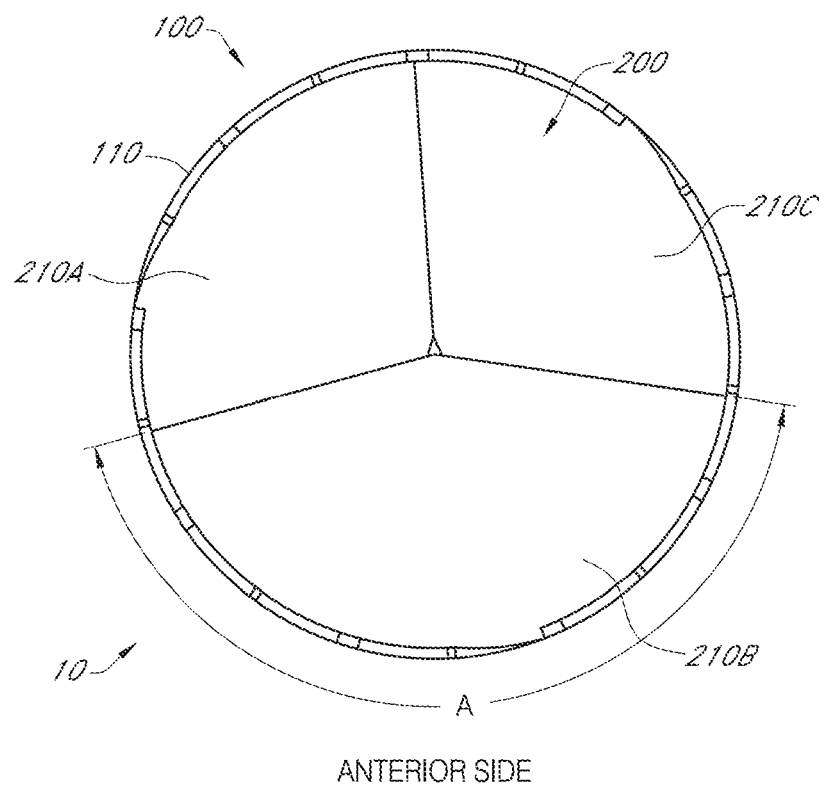
Figure 8C:
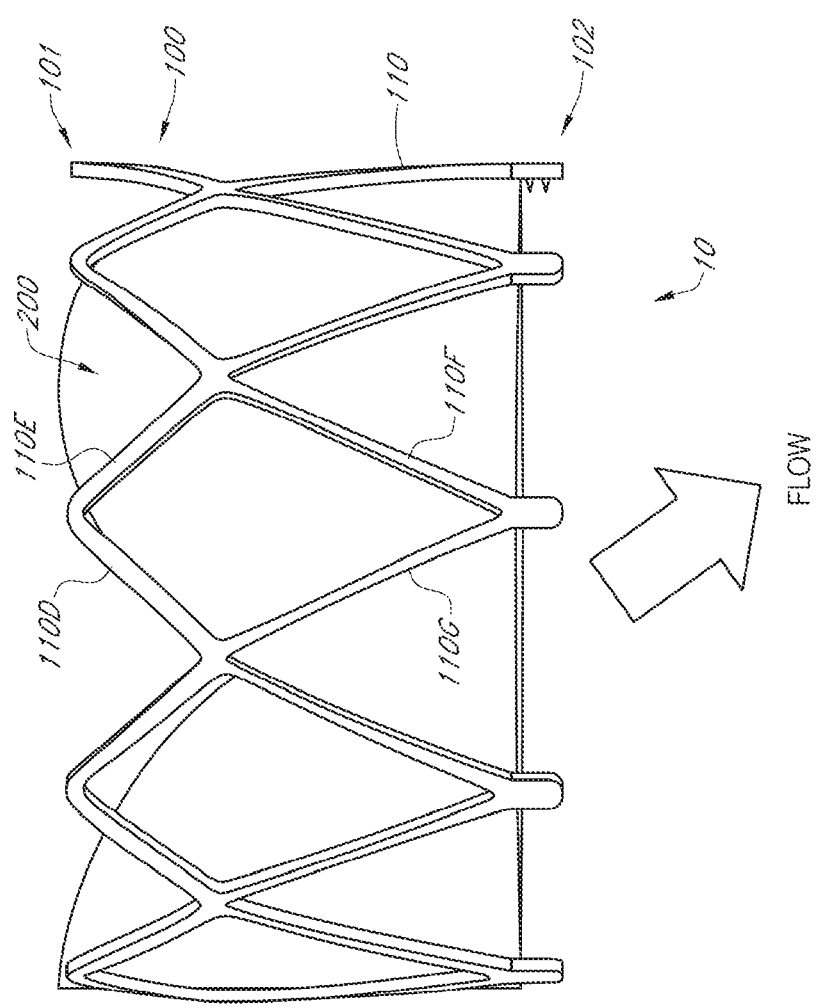
Figure 8E:
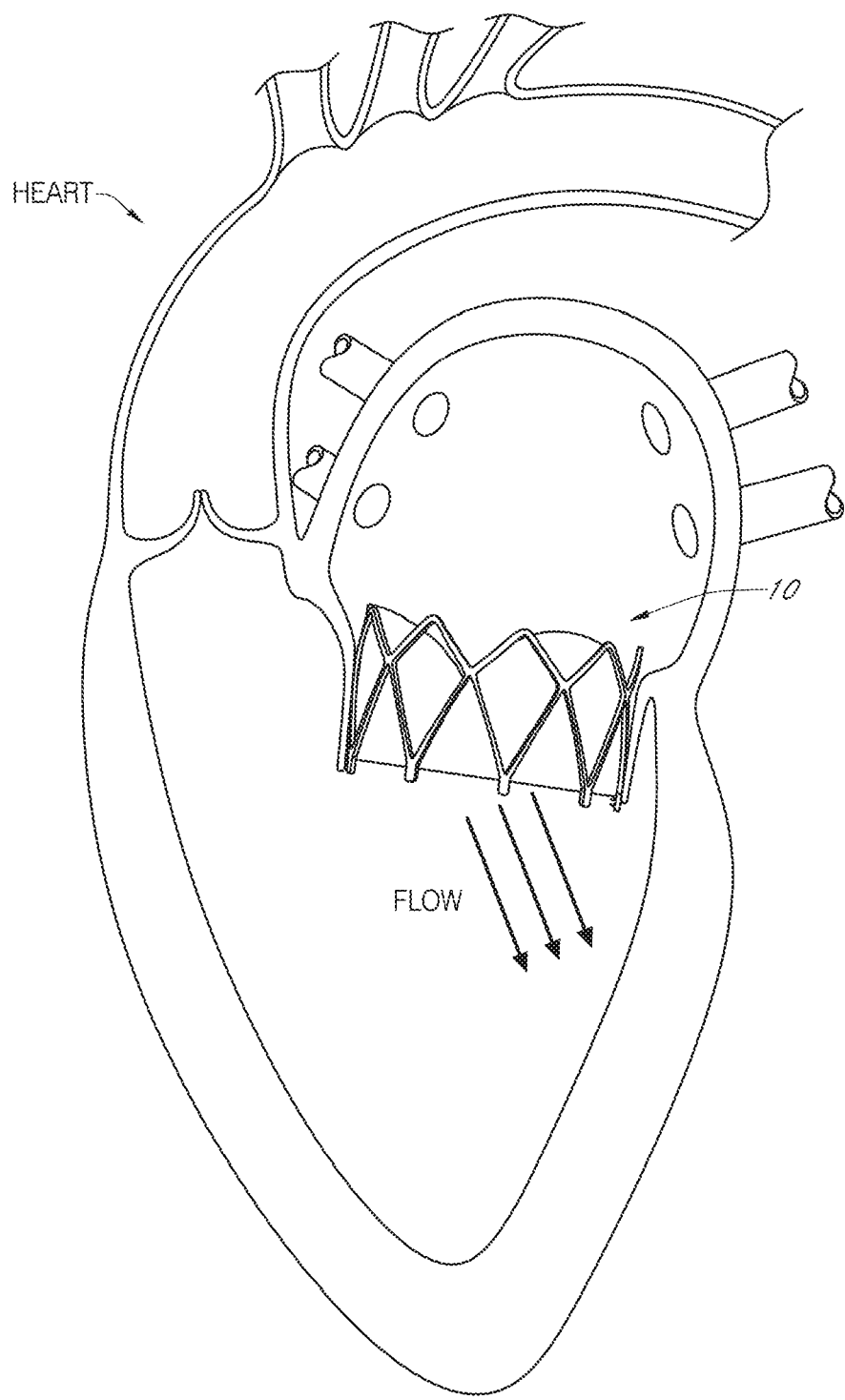
FIGS. 8E-8F are partial cross-section views of a heart mitral valve with the embodiments of a heart valve device implanted therein for re-direction of blood flow entering the left ventricle.
Figure 8F:
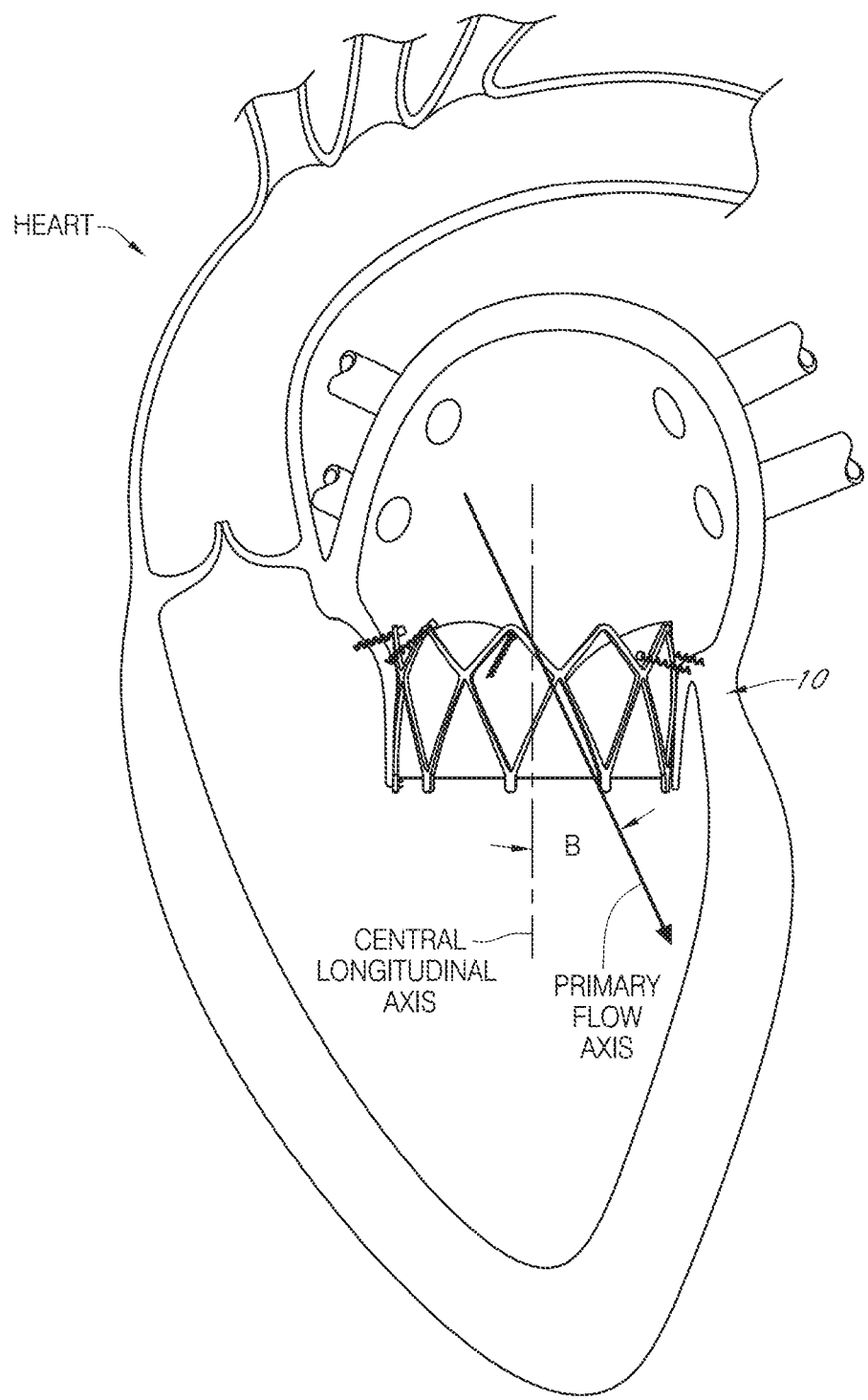

FIG. 8A is a top view of an embodiment of the device 10. In FIG. 8B, the image on the right is a top view of an embodiment of the device 10 and the image on the left is a side view of that device 10. FIGS. 8C and 8D are side views of the devices 10 of FIGS. 8A and 8B showing embodiments of re-directed flow exiting the devices 10. FIGS. 8E-8F are partial cross-section views of a heart mitral valve with the embodiments of the devices 10 implanted therein for re-direction of blood flow entering the left ventricle LV.

As shown in FIGS. 8A-8B, the valve 200 may include the three leaflets 210A, 210B, 210C. In some embodiments, there may only be two of the leaflets. The device 10 may include the valve 200 with the leaflets configured, for example sized and/or positioned, to direct the blood flow to the posterior of the heart. To re-direct the blood flow, the leaflets 210A, 210B, and/or 210C may thus be different sizes. As shown, the leaflet 210B may be larger than the leaflets 210A and 210B. The leaflet 210B may be located on the anterior side of the mitral valve MV when implanted. The larger leaflet will not open as much as the other two smaller leaflets, directing the flow toward the smaller leaflets located posteriorly. The same can be done with two larger leaflets and only one smaller leaflet as well by orienting the commissure of the two larger leaflets to the anterior of the native mitral valve. Alternatively or in addition, the blood flow may be re-directed by attaching a portion of the leaflets 210A, 210B, 210C at the shared commissures. The commissure attachment may prevent the leaflets from fully opening, thus directing the outgoing flow. These or other configurations of the valve leaflets, such as the valve leaflets 210A, 210B and/or 210C, may re-direct blood flow exiting the device 10.

The leaflets of the valve 200 may be attached with various methods to achieve the various configurations and functions described herein. Attachment of adjacent leaflets of the valve 200 may be accomplished by conventional stitching using suture such as in an open surgical procedure, or by suture loops or application of clips or other tissue anchors in a percutaneous or trans apical procedure. The attachment zone is preferably adjacent the commisure and extends no more than about 25% and generally no more than about 15% or 10% of the length of the coaptive edges of the leaflets of the valve 200. The opposing leaflets remain unconnected to each other within a central coaptation zone, allowing the opposing leaflets to remain functioning as a single valve 200. An attachment zone may be provided at a single end or at both opposing ends of the leaflets.

In some embodiments, re-direction of the blood flow may be accomplished with the device 10 by orienting the device 10 when implanted such that blood is directed by the leaflets, such as the leaflets 210A, 210B, 210C, in a particular direction. In some embodiments, the valve 200 may have a particular arrangement of leaflets, such as leaflets 210A, 210B and/or 210C, as discussed, as well as a particular orientation when implanted. For example, the valve 200 may have the arrangement of leaflets 210A, 210B, 201C as shown in FIGS. 8A-8B and the device 10 may have an orientation when implanted that may be generally along an axis defined by the native mitral valve. In some embodiments, the device 10 may have an orientation when implanted that may be generally off this axis. Thus, a method of directing the flow toward the posterior wall is to angle the attachment plane of the device 10, for example with a cylindrical device 10. The flow can be appropriately directed by adding features to the structure supporting the device 10, such as the frame 100, that modify the attachment plane of the implanted device 100.

As shown in FIGS. 8D and 8F, the expanded frame 100 may define a central longitudinal axis about which the frame 100 is concentrically disposed. For example, the unconstrained expanded configuration of the frame 100 may be cylindrical, frustoconical, or other shapes, and defining the central longitudinal axis. The device 10 may re-direct flow, as mentioned. The flow direction may be generally as shown in FIGS. 8C and 8E. Further, the direction of flow, whether re-directed or not, may be along a primary flow axis, as shown in FIGS. 8D and 8F. In some implementations of the device 10, it may be desirable to establish the primary flow axis inclined posteriorly at an angle "B" with respect to the central longitudinal axis defined by the frame 10. The primary flow axis is the general direction along which the flow travels into the left ventricle LV after exiting and/or while travelling through the device 10. The angle "B" between the central longitudinal axis and the primary flow axis may be at least about 5 degrees, and in some implementations at least about 10 degrees, but generally less than about 45 degrees, and in some implementations less than about 20 degrees. Examples embodiments of this angle are shown as angle "B" in FIGS. 8D and 8F.

Deflection of the primary flow axis from the central longitudinal axis may be accomplished in a three leaflet valve, for example the valve 200 including the leaflets 210A, 210B, 210C, by increasing the size of the anterior leaflet, such as the anterior leaflet 210B. Example embodiments of such a device 10 are shown in FIGS. 8A and 8B. Enlarging the anterior leaflet, such as the anterior leaflet 210B, will displace the primary flow axis in the posterior direction. The size of the anterior leaflet, such as the anterior leaflet 210B, may be increased such that the anterior leaflet 210B occupies an angle "A" of the circumference of the valve 200, where the valve, whether circular or otherwise, has a total circumference of 360 degrees. This is shown, for example, in FIGS. 8A and 8B (in FIG. 8B, the image on the right). In some embodiments, the size of the anterior leaflet 210B may be increased such that the anterior leaflet occupies an angle "A" of at least about 125 degrees of the circumference of the valve 200. In some embodiments, the anterior leaflet 210B occupies at least about 135 degrees, or 145 degrees, or 160 degrees, or more, of the circumference of the valve 200.

FIG. 9 is a partial side view of an embodiment of the heart valve device 10 showing an interface between the frame 100 and an anchor 300 including a coil 320 surrounding a central spike 340. The distal spike 340 may be central to the axis of the coil 320 of the anchor 300 which rotates about the spike 340 to increase the moment, strength and fatigue resistance of the anchor 300. The spike 240 may be coupled with the frame 100, such as the distal apex 104, discussed in further detail herein, for example with respect to FIGS. 2 and 3A.

Figure 10:
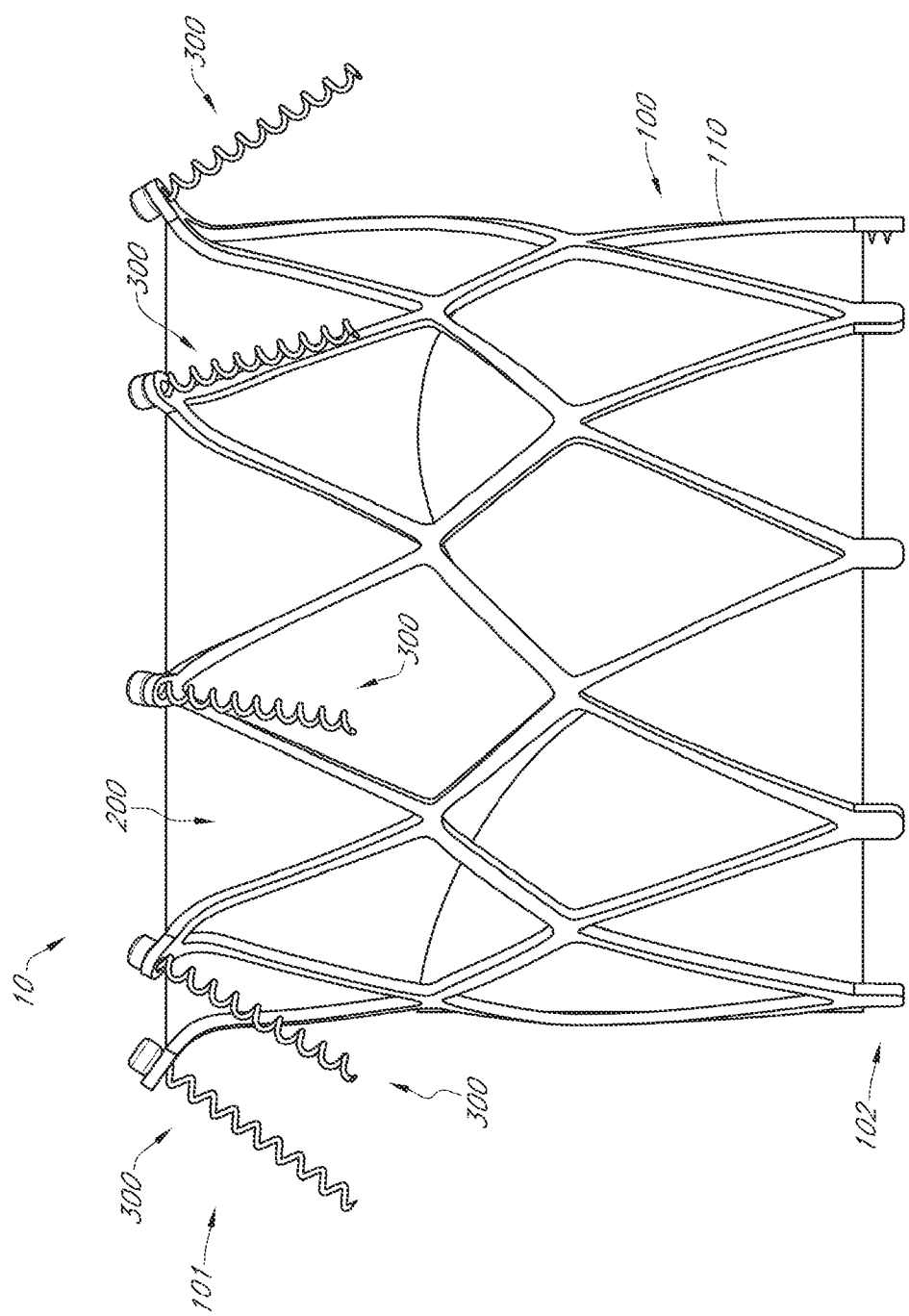
FIG. 10 is a side view of an embodiment of a heart valve device having an extended frame for extension into the left ventricle and exclusion of the native mitral valve when the device is implanted within the mitral valve annulus.

FIG. 10 is a side view of an embodiment of the heart valve device 10 having an extended frame 100. The taller frame 100 extends the device 10 lower into the left ventricle LV. The device 10 with extended frame 100 may extend into the left ventricle LV and exclude the native mitral valve when the device 10 is implanted within the mitral valve annulus MVA. The proximal end 101 of the frame 100 may be attached to the valve annulus and the distal end 102 may exclude the native valve.

Figure 11:
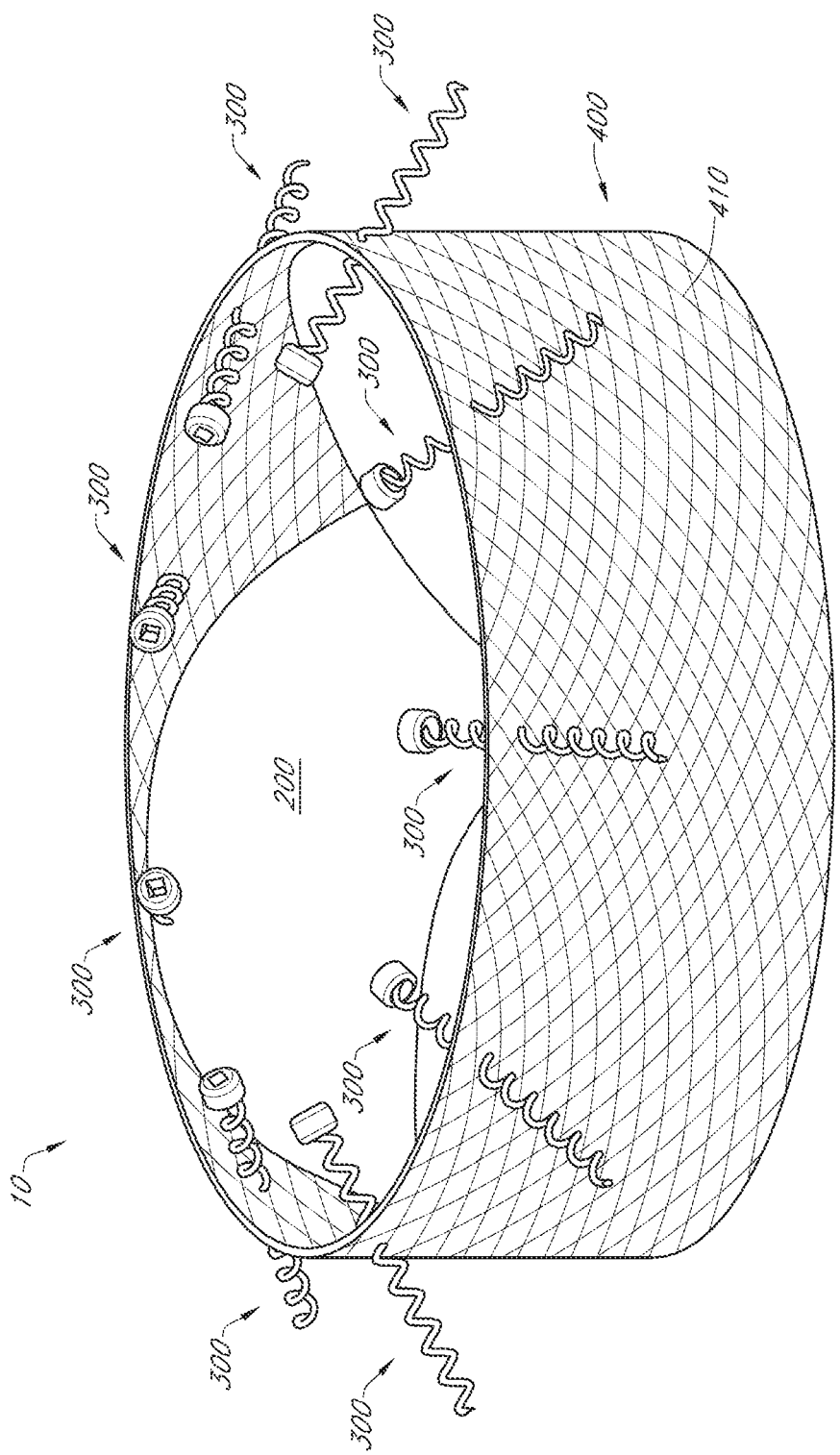
FIG. 11 is a perspective view of an embodiment of a heart valve device having a seal embodied as a woven barrier.

FIG. 11 is a perspective view of an embodiment of the heart valve device 10 having a woven seal 400. The woven seal 400 includes a woven seal body 410 formed of woven material surrounding the device 10 to prevent leakage around the periphery. The woven material may be constructed of a polymer fabric or a metallic wire to provide more structural integrity. Both means would be of an expandable nature to allow for varying patient anatomy. The woven seal 400 may substitute for the frame 100. That is, the woven seal 400 may take the place of the frame 100, providing both structural and sealing capabilities to the device 10. The anchors 300 may be couple with the woven seal 400 as shown. The woven seal 400 may have the same or similar features and/or functionalities as the frame 100, such as a flared end or skirt 150, an exterior seal 500, etc.

FIG. 12 is a perspective view of an embodiment of the heart valve device 10 having an expandable frame 100. The device 10 has an expandable frame 10 and anchors 300 located on the proximal end 101. An additional feature may be at the distal end 102 of the frame 100 to point a portion inward and proximal locking the frame 100 to the native valve annulus. The frame 100 may include one or more of the skirts 150. As shown, a first skirt 150 may be located at the proximal end 101 and include one or more frame tabs 112 with openings therethrough to receive the anchors 300. A second skirt 150 may be located at the distal end 102 and include one or more angled frame portions 114. The portions 114 may be located at the distal end 102 of the frame 100 and extend outward and proximally. The portions 114 may expand upon delivery of the device 10 to secure the device 10 within the mitral valve annulus.

Depending upon the desired performance of the valve 200, one or both of two different types of seals may desirably be carried by the valve. As shown in FIG. 12, the device 10 may have the seal 400. As has been described herein, valve replacements in accordance with the present device 10 may include a tubular support frame 100. Depending upon whether the final implanted position of the frame 100 is primarily extending into the left atrium, or instead extends in the ventricular direction such as to exclude the native leaflets, the anchors 300 may be carried by the proximal end 101 (for example, atrial) or the distal end 102 (for example, ventricular) of the frame 100. As a consequence, the annulus of the prosthetic valve 200 may be axially displaced along the flow path with respect to the native annulus. To prevent blood flow in the annular space between the annulus of the prosthetic valve 200 and the native annulus, the frame 100 is preferably provided with an annular seal 400, such as a thin sleeve or membrane, which prevents blood flow through the wall of the frame in between the prosthetic annulus and the native annulus.

It may also be desirable to include structure to inhibit perivalvular leaks, for example where blood escapes around the valve 200 and/or device 10. A perivalvular leak may occur in between the device 10 and the native annulus, due to potential mismatch in the geometry of the native valve orifice and the outside diameter of the device 10. For the seal 400, relating to potential leaks through the wall of the frame 100, an impervious membrane may be carried on the inside of the frame 100 (as shown in FIG. 12), on the outside of the frame 100, or both. For the seal 500, relating to inhibiting perivalvular leaks, the barrier or membrane will preferably be carried on the outside surface of the frame 100 as will be apparent to those of skill in the art. Thus a seal 400 or 500 on the outside of the frame 100 may be configured to provide both functions, having an axially extending component to cover at least a portion of the length of the frame 100 including the base of the leaflets, and a radially outwardly extending or extendible component to fill spaces between the frame 100 and the adjacent anatomy.

Figure 13A:
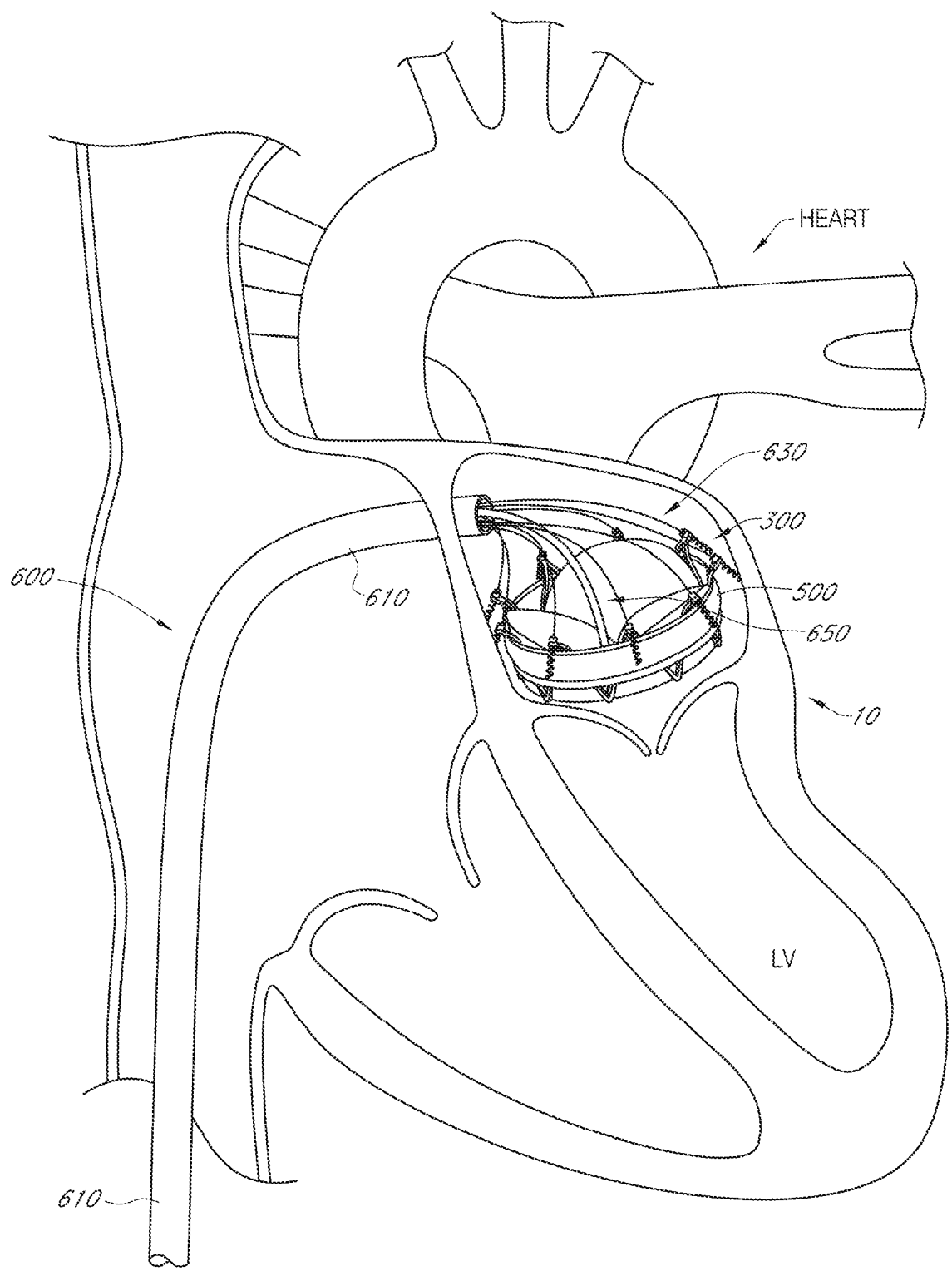
FIGS. 13A-13C are partial cross-section views of a human heart showing an embodiment of a delivery system for delivering a heart valve device having a seal embodied as a ring or cuff, such as a toroid.
Figure 13B:
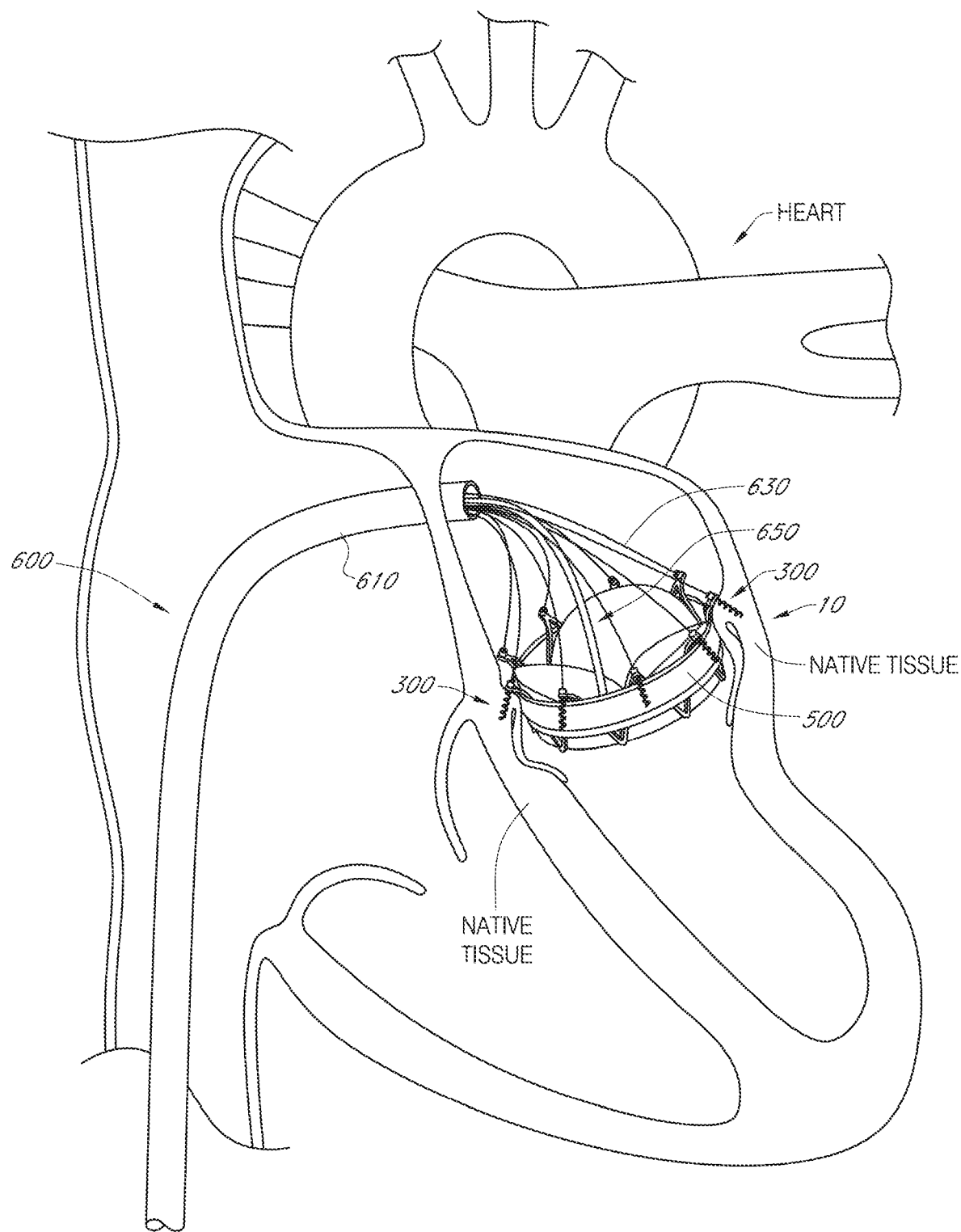
Figure 13C:
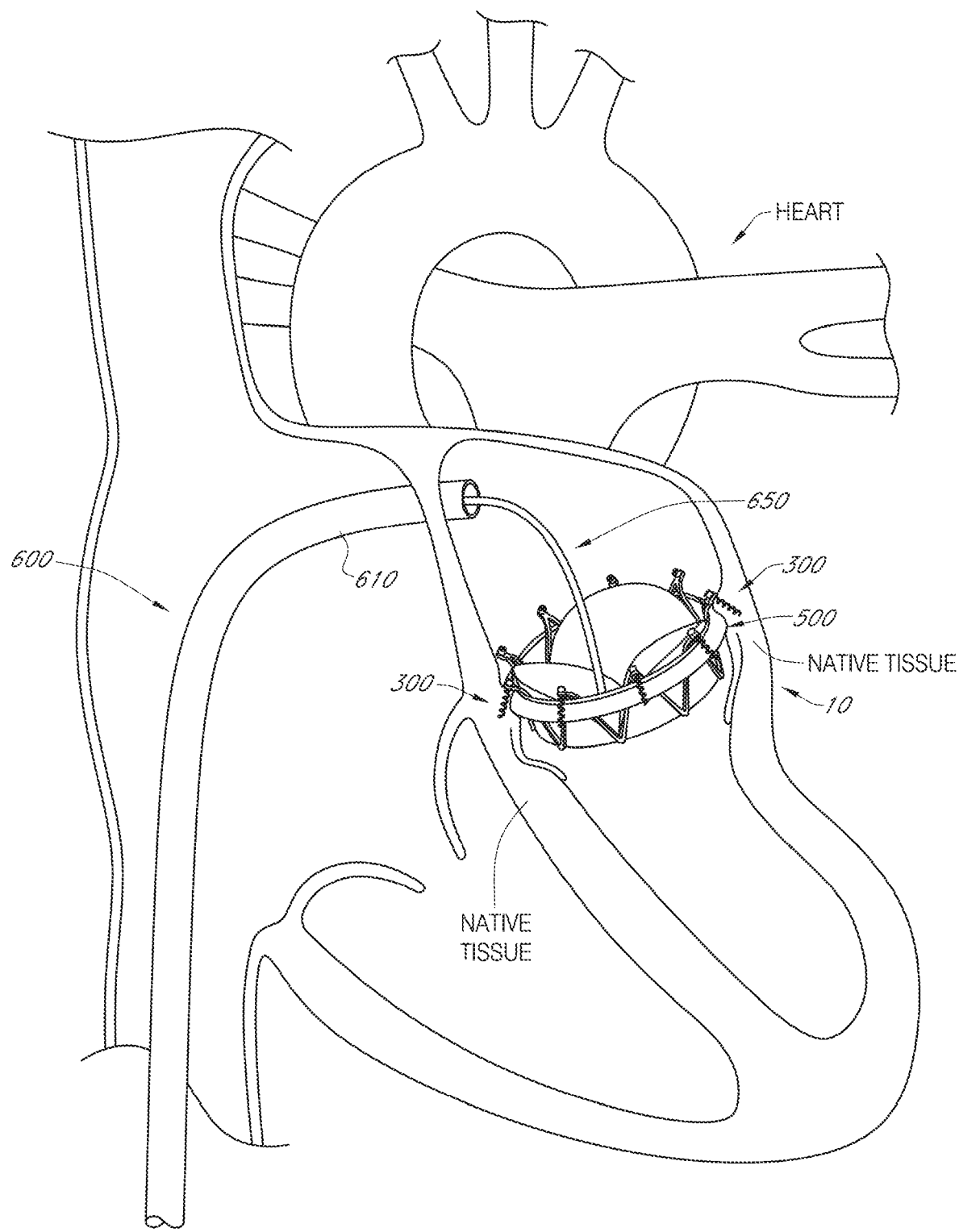

An embodiment of a radially outwardly extending component to fill spaces between the frame 100 and the adjacent anatomy is the annular seal 500 shown in FIGS. 13A-13C. The seal 500, such as a sealing ring, may be located outside the frame 100, for example along a midsection of the frame 100, to limit leakage about the frame 100 as discussed. In addition or alternatively, the seal 500 may be located inside the frame 100. The seal 500 may be active where an expansion means, such as an inflation mechanism, may increase the physical size of the seal 500. Thus, the seal 500 may have a smaller, contracted configuration during delivery and a larger, expanded configuration when implanted. Alternatively, the seal 500 may be passive. For example, the seal 500 may self-expand upon expansion of the device 10 within the heart. The seal 500 may include the radially outwardly extending ring component as shown, but it may also include an axially extending component to act as a barrier, as discussed above.

FIGS. 13A-13C are partial cross-section views of a human heart showing an embodiment of a delivery system 600 for delivering the heart valve device 10. As shown, the device 10 may include the seal 500. FIG. 13A illustrates the device 10 being delivered veniously from the groin via transeptal puncture to access the left ventricle LV. FIG. 13B illustrates the system 600 and device 10 with the anchors 300 inserted into the valve annulus. FIG. 13C illustrates the system 600 and the device 10 with the anchors 300 inserted and the rotational anchors 300 disconnected from the delivery catheter 640 with the sealing cuff inflated. Attached to the device 10 in FIGS. 13A and 13B are rotational connections 630 to drive the coil anchors 300 and an inflation tube 650 to dimensionally change the seal 500, to limit or halt perivalvular leak through hydraulic pressure.

The seal 500 may be a sealing ring or cuff. The seal 500 may have the general shape of a toroid or the like. To prevent leakage around the frame 100, the seal 500 may be added between the proximal portion that resides in the left atrium (above the mitral valve) and the left ventricle LV. The seal 500 could be of a passive nature and constructed of woven fabric or velour. An alternative means could utilize a more active seal 500 that is inflated or expanded to meet the surrounding tissue. Construction of the active seal 500 could utilize a fluid solution to hydraulically expand and fill with a saline or polymer solution to harden to a predetermined durometer. The seal 500 could be constructed from a polymer balloon material such as nylon, Pebax or the like, and filled from the handle of the delivery catheter 610. In some embodiments, the seal 500 comprises an annular skirt, such as a flange or the like, which may be similar to the skirt 150 described with respect to the frame 100. The skirt of the seal 500 may be attached at one end to the device 10 and inclining radially outwardly in either the proximal or distal direction. The skirt of the seal 500 may be carried by a support structure, such as a plurality of struts. Preferably, the skirt of the seal 500 inclines radially outwardly in the distal direction, so that ventricular pressure tends to enhance the sealing function between the skirt of the seal 500 and the adjacent anatomy.

In some embodiments, the seal 500 comprises an annular tube carried on a radially outwardly facing surface of the device 10, such as a surface of the frame 100. The tube of the seal 500 may be provided with a fill port, having a valve therein. A fill tube may extend from the deployment catheter, for example the tool 610, to the fill port of the seal 500, for placing the tube of the seal 500 into fluid communication with a source of inflation media, by way of an inflation lumen extending throughout the length of the catheter. The annular tube of the seal 500 may be at least partially filled following placement, e.g. implantation, of the device 500 but prior to releasing the device 10 from the deployment catheter. The presence of perivalvular leaks may be investigated by injection of contrast media and observation of the atrium under fluoroscopy. The tube of the seal 500 may be further inflated, or other responsive action may be taken such as repositioning the device 10, depending upon the observed functionality. Once functionality of the device 10 and level (if any) of perivalvular leakage is deemed satisfactory, the fill tube may be decoupled from the fill port of the tube of the seal 500 and the valve of the fil port closed to retain inflation media therein, and the device 10 released from the deployment catheter.

FIGS. 14A-14B are partial side views of an embodiment of the heart valve device 10 showing the frame 100 with a closure system 140 including a threaded portion 142 and corresponding moveable restraint 144, such as a collar, at the proximal end 101. There may be at least four moveable restraints 144. The moveable restraint 144 may have an aperture for receiving therein a pair of adjacent struts of the frame 100. FIG. 14A illustrates an initial unlocked position of a pair of struts 110A, 110B of the body 110 from the frame 100. FIG. 14B illustrates the final locked position of the struts 110A, 110B. The restraint 144 may be slidable axially along a pair of struts. Advancing the moveable restraint 144, such as the collar, in an axial direction reduces the angle between the pair of struts thereby reshaping the frame 100. As further shown, the pair of struts 110A, 110B may have a cable 160 connecting the apexes of the struts 110A, 110B at the distal end 102, where a tension force applied to the cable 160 would draw the two apexes and anchors 300 together along with the associated tissue to which the anchors 300 are imbedded. The cable 160 may be connected to openings 116A, 116B in the struts 110A, 110B. Additionally, the moveable restraint 144, such as a collar with an aperture therethorugh, an internally-threaded collar, nut, etc. could lock the position and/or angle of the struts 110A, 110B and relieve the tension on the cable 160. The closure system 140 could be a notched feature to hold as a thread for a nut or a notch to hold the moveable restraint 144 in its desired position resisting opposing motion up the struts 110A, 110B. In some embodiments, the frame 100 may be configured to be reshaped such that a width, for example a diameter, at the proximal end 101 is different from a width, for example a diameter, at the distal end 101.

The cable 160 or other tension element connecting adjacent struts may be releasably grasped by a retractor element such as a pull wire extending through the deployment catheter and having a distal hook, or by a suture loop wrapping around the cable 160. Proximal retraction of the retractor element displaces the cable 160 proximally as illustrated in FIG. 14B. A proximal retraction element and cable 160 may be provided between each adjacent pair of struts, or every second or third pair of struts, depending upon the desired performance. Alternatively, cable 160 may comprise a lasso construction in which it surrounds the entire frame 100, or is connected to alternating pairs of adjacent struts. One or both ends of the cable 160 forming the lasso loop may extend proximally through the deployment catheter, so that proximal retraction of the at least one end of cable 160 causes a circumferential reduction in the frame 100. In an alternate construction, cable 160 surrounds at least a portion of the frame 100 but is constructed such that cable 160 is an integral portion of the frame 100, and remains attached to the frame 100 post deployment. Circumferential reduction of the frame 100 is accomplished by proximal retraction of a retraction element which is releasably coupled to the cable 160, such as has been discussed above in connection with FIG. 14B.

Figure 15:
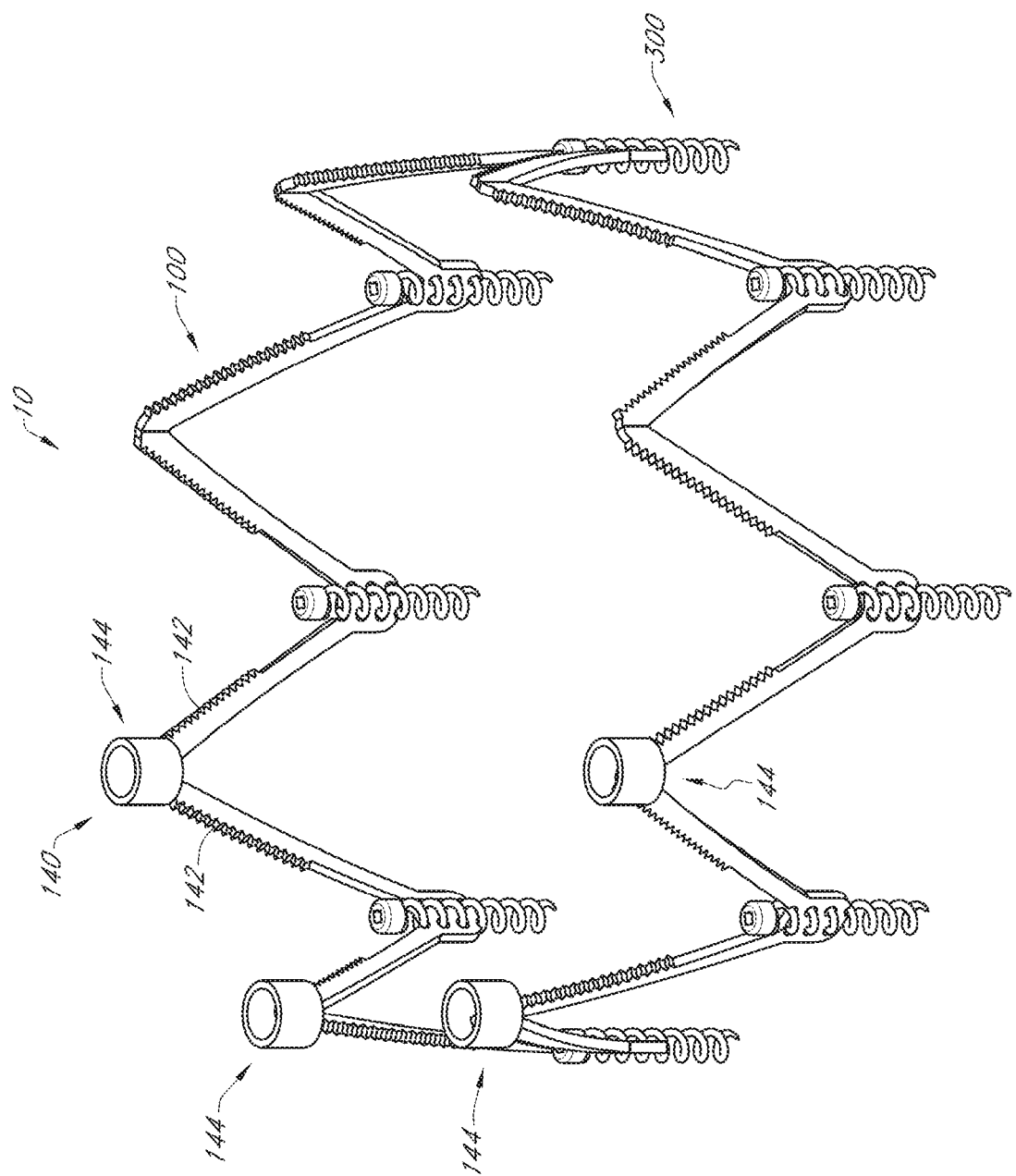
FIG. 15 is a perspective view of an embodiment of a heart valve device showing a frame with a closure system including threaded portions and selective placement of corresponding moveable restraint embodied as a collars.

FIG. 15 is a perspective view of an embodiment of the heart valve device 10 showing the frame 100 with several closure systems 140, including threaded portions 142 and selective placement of corresponding collars 144. Some or all of the anchors 300 and collars 144 could be activated depending upon the patient's need. Not all of the frame 100 vertices may include the collars 144.

Figure 16:
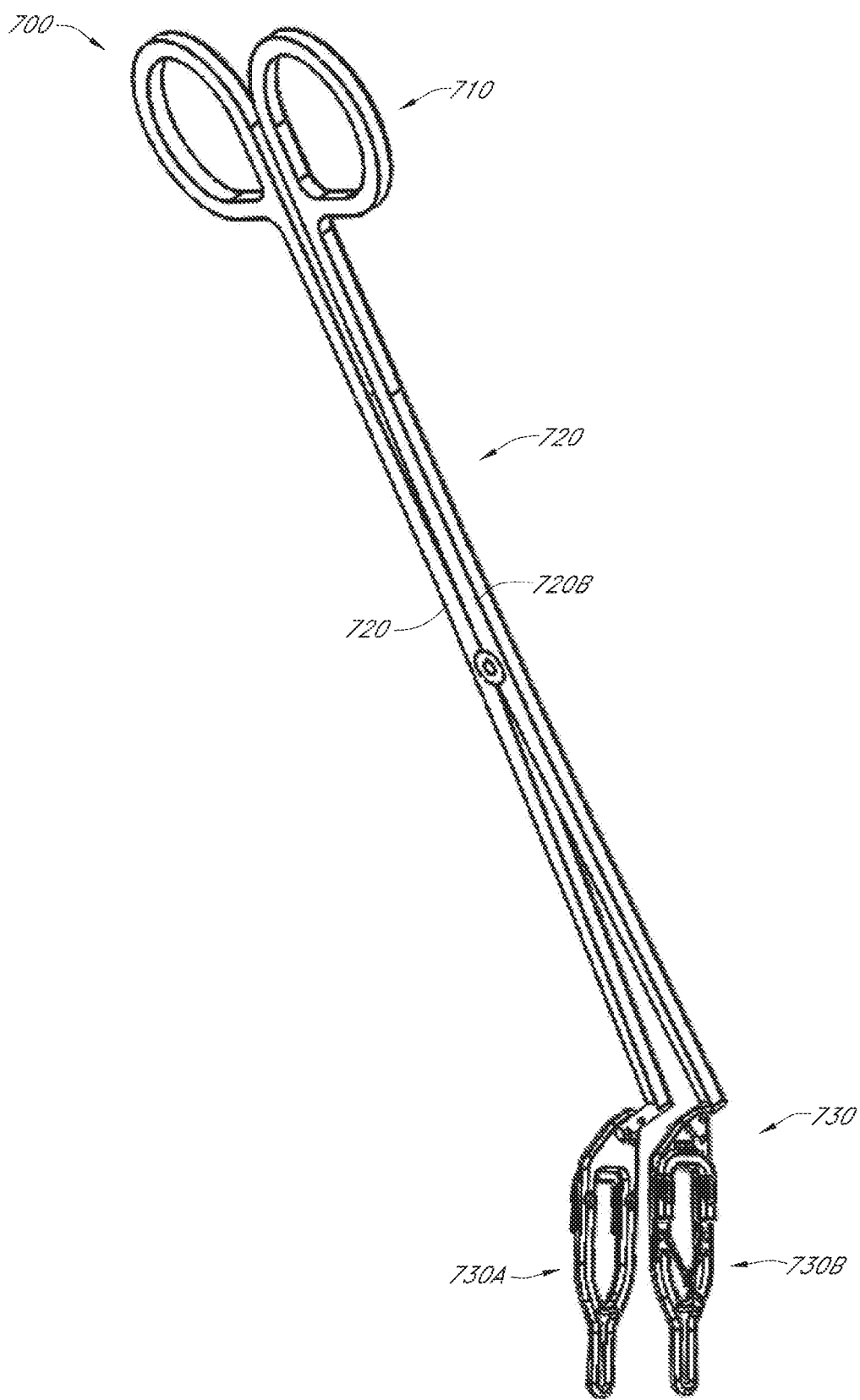
FIG. 16 is a perspective view of a tool for holding the various heart valve devices described herein for surgical placement or catheter delivery of the devices.
Figure 17:
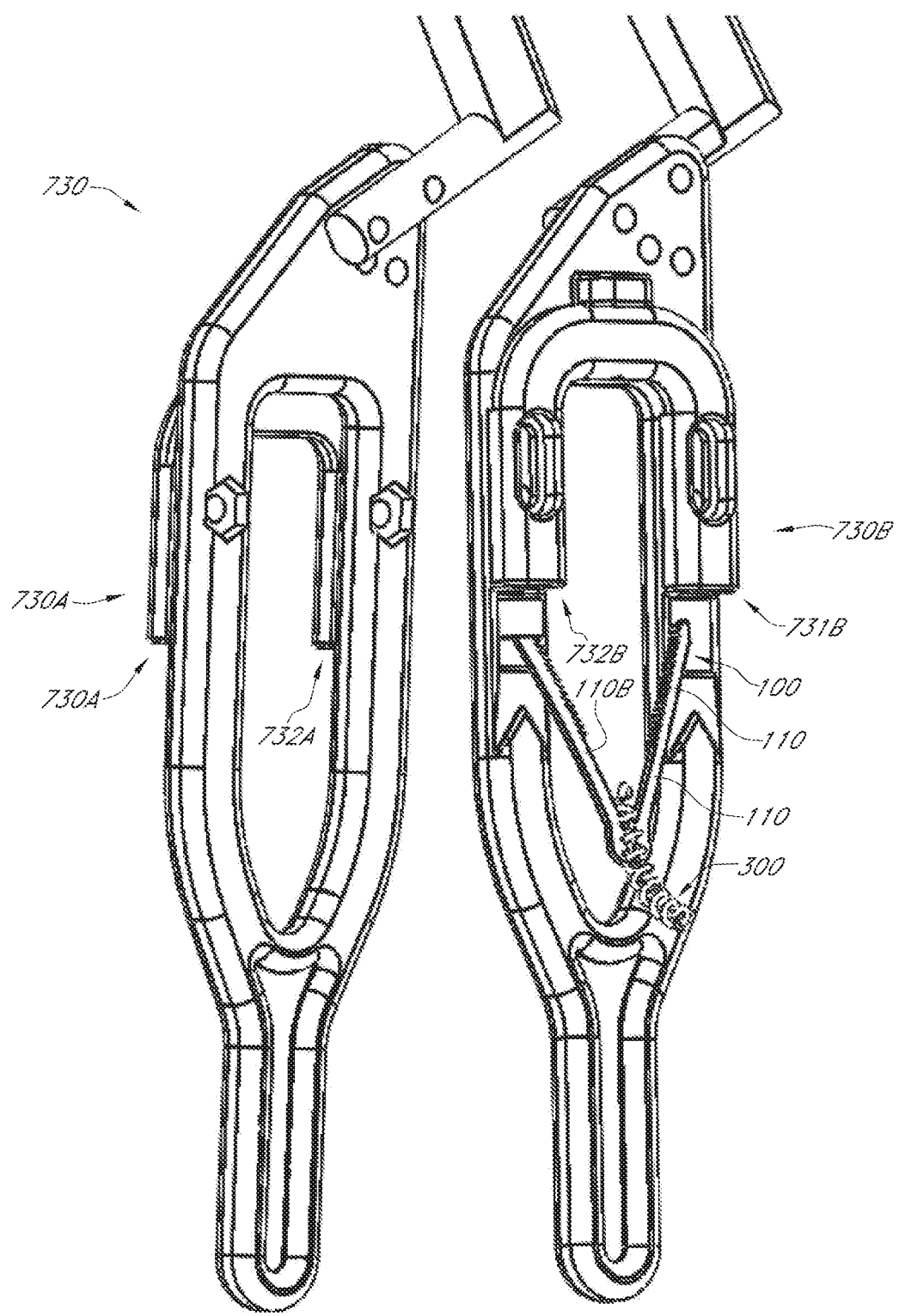
FIG. 17 is a perspective view of an embodiment of a tool head that may be used with the tool of FIG. 16.

FIGS. 16-17 are perspective views of a tool 700 for holding the various heart valve devices 10 described herein for surgical placement or catheter delivery of the devices 10. The tool 700 may include a handle 710, body portions 720A, 720B, and corresponding tool heads 730A, 730B. The tool 700 may be used for surgical placement of the frame 100, holding the tool 700 open and/or closed depending upon the position and/or angle of the handle 710 and/or body portions 720A, 720B. A similar tool could be constructed for a catheter delivery via transapical or transfemoral. As shown in FIG. 17, the tool heads 730A, 730B may include receiving portions 731A, 731B, 732A, 732B. For example, the receiving portion 731B may receive and hold therein the strut 110A of the frame body 110, and the receiving portion 732B may receive and hold therein the strut 110B.

Figure 18:
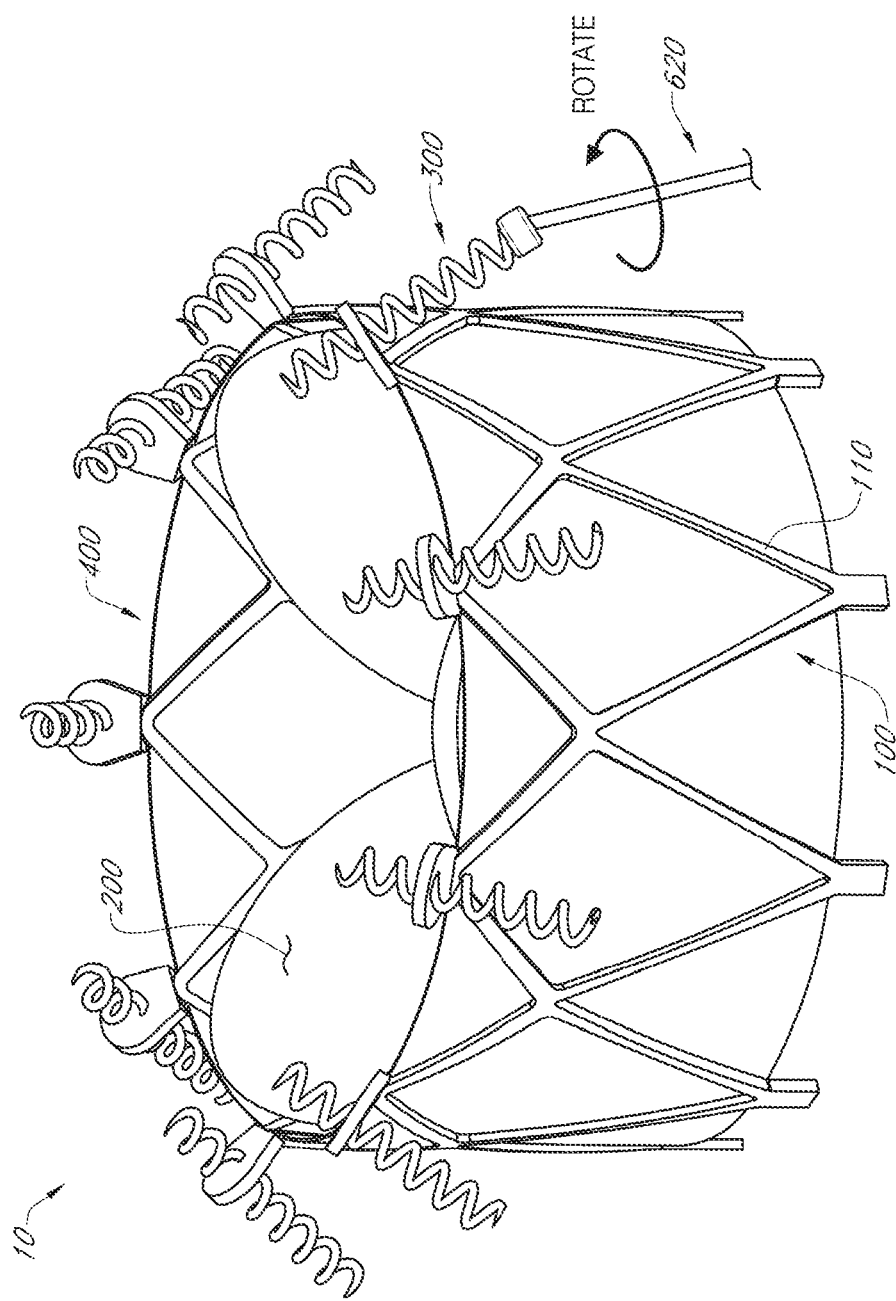
FIG. 18 is a perspective view of an embodiment of a heart valve device with an interior annular seal embodied as a barrier and angled anchors for delivery and anchoring of the device from within the left ventricle, showing a delivery system driver coupled with one of the anchors.

FIG. 18 is a perspective view of an embodiment of the heart valve device 10 with angled anchors 300 for delivery and anchoring from the left ventricle LV. The device 10 may be delivered and anchored from the left ventricle LV where the anchors 300 may be driven in from below the device 10 in the left ventricle LV. For example, the driver 620 may rotate the anchors 300 from the left ventricle LV. The device 10 may include the seal 400 as shown, such as an interior annular barrier, as discussed in further detail herein.

Defining the frame 100 diameter to match the patient's anatomy can be accomplished by pre-defining a shaped set size using a shaped memory material such as Nitinol or ballooning the malleable frame 100 material to a defined diameter. Other means would be to close the frame 100 dimensions by collapsing the frame 100 using a synching wire wrapped around the diameter and reducing the length of the wire causing a force to change the frame 100 shape and dimensions. Additional means would include a force to change the shape of the struts 110A, 110B on the sinusoidal frame 100 including a bending or collaring force about the struts 110A, 110B moving the base of the frame 100 closer together and gathering the associated surrounding tissue. Additional means would include cutting threads into the frame struts 110A, 110B to mate with the moveable restraint 144, such as a nut, advanced or rotated over the struts 110A, 110B moving the struts closer to one another resulting in a gathering force of the surrounding tissue. Another means would include the cable 160, thread or other connection between the lower segment of the struts where a tensioning force would move the two struts 110A, 110B closer to one another. This force could be a tension in any direction including proximal or distal force to push or pull the cable 160 causing a gathering of the surrounding struts and associated tissue. The connection between the struts could be driven by a threaded means or push/pull mechanism outside the body and through the catheter to the device 10.

Once the struts 110A, 110B are pulled closer to one another, the apex of the struts 110A, 110B can be locked or secured in place with the moveable restraint 144, such as a collar or nut, placed over the struts 110A, 110B, as described herein. Locking of the struts 110A, 110B can be achieved with the closure system 140 to prevent the moveable restraint 144 from moving proximally or loosening relative to the struts 110A, 110B, allowing the struts 110A, 110B to move away from one another. A small tab may engage a ratchet surface holding the moveable restraint 144 from moving proximally but allowing the moveable restraint 144 to be farther advanced if necessary. Alternatively, the moveable restraint 144 could be a nut threaded over the apex holding the proximity of the two struts 110A, 110B close to one another.

The device 10 may be shaped using these and other methods to achieve a variety of different shapes and sizes. The moveable restraints 144 may be coupled with the frame 100 and configured to restrain the frame 100 at a desired width, diameter, orientation, shape, etc. Other embodiments of moveable restraints may be implemented, such as loops to cinch the frame 100, as discussed below. Some of these shapes, sizes, configurations, etc. are described with respect to FIGS. 19A-25B.

Figure 19A:
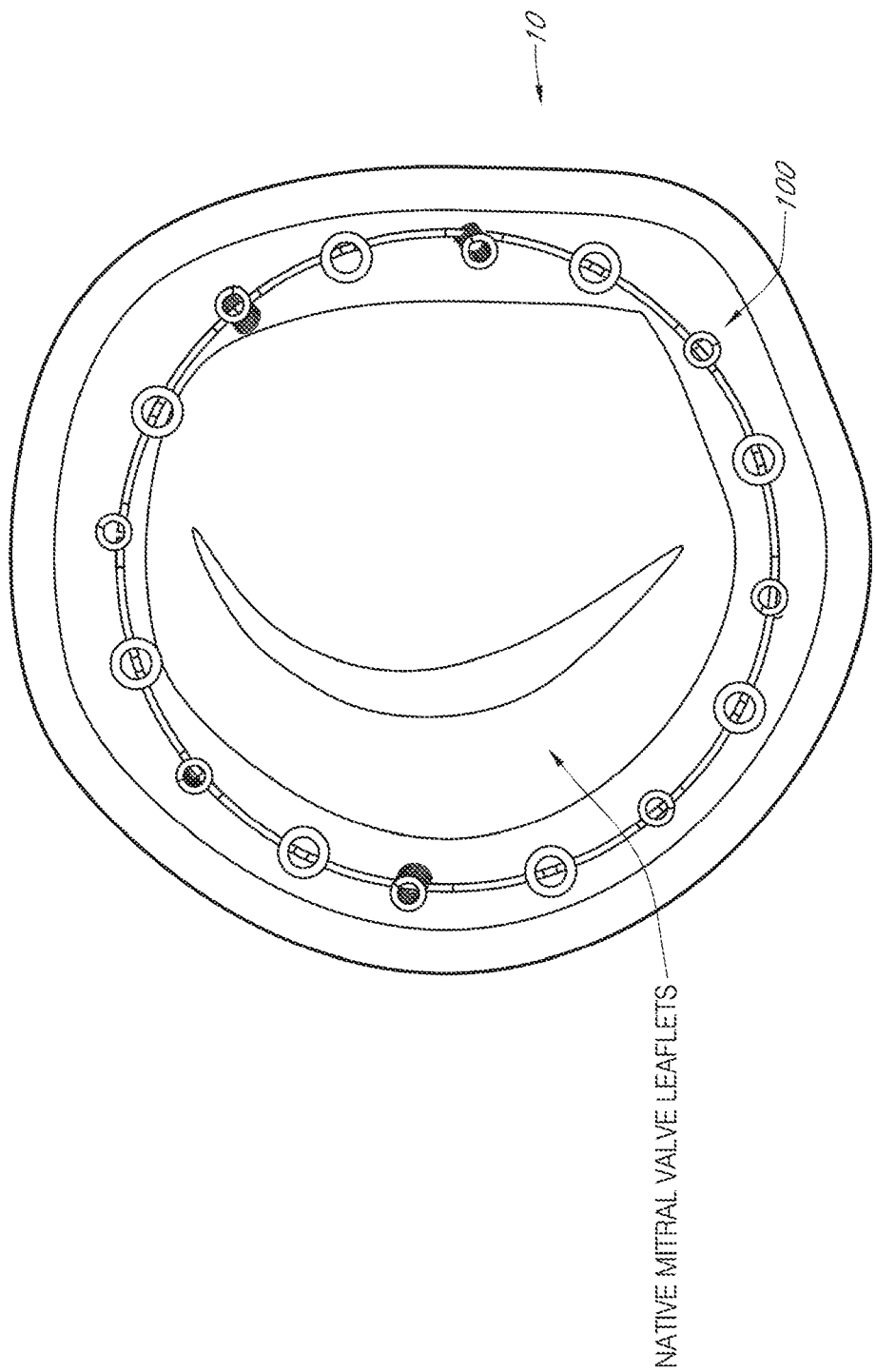
FIGS. 19A-19B are top and perspective views respectively of an embodiment of a heart valve device having a frame embodied as a rounded ring.
Figure 19B:
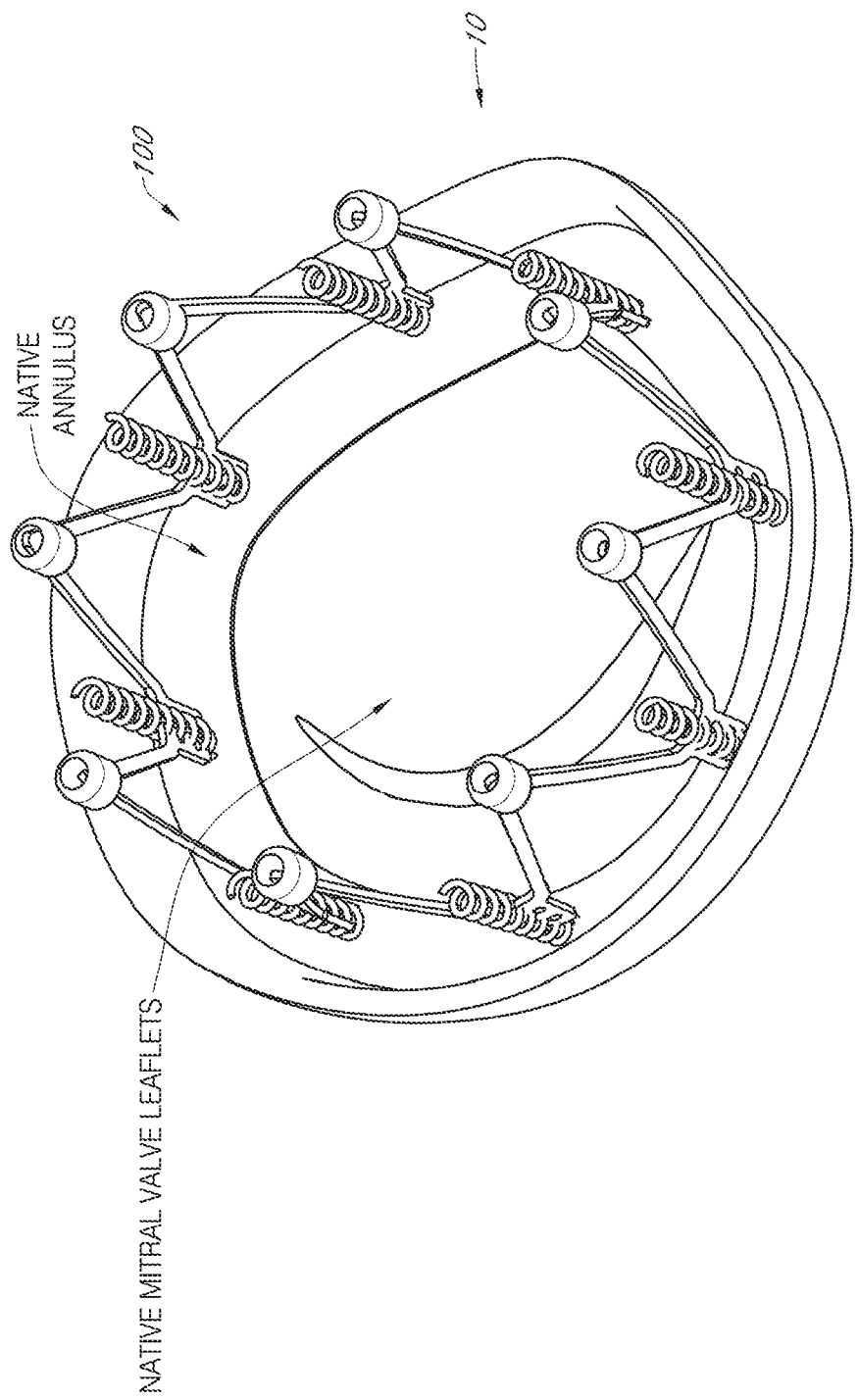

FIGS. 19A-19B are top and perspective views respectively of an embodiment of the heart valve device 10 having the frame 100 embodied as a rounded ring. The device 10 may include a frame 100 having a body 110 with a ring shape. The body 110 may be rounded, for example circular. The device 10, in its round shape, can be placed in or around the annulus, anchored and cinched to reduce the native annulus diameter, after which the device 10 maintains its original round shape.

Figure 19C:
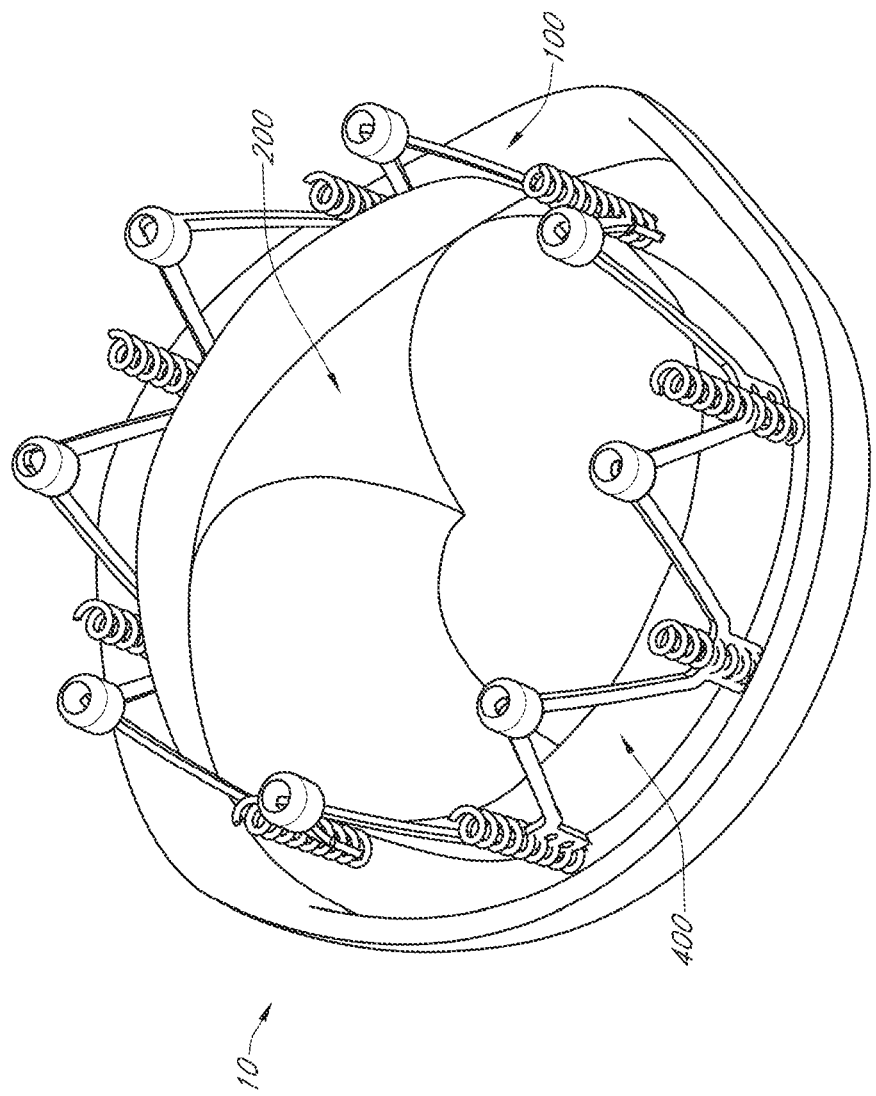
FIG. 19C is a perspective view of the device of FIGS. 19A-19B with a valve.

FIG. 19C is a perspective view of the device 10 of FIGS. 19A-19B with a valve 200. The device 10 may include a frame 100 embodied as a ring-shaped body 110 coupled with, or configured to couple with, the valve 200. The frame 100 may have the valve 200 built into it or secondarily attached. The device 10 can be placed in the annulus, anchored, and cinched to reduce the native annulus diameter. The device 10 will maintain its round shape with the valve 200.

Figure 20A:
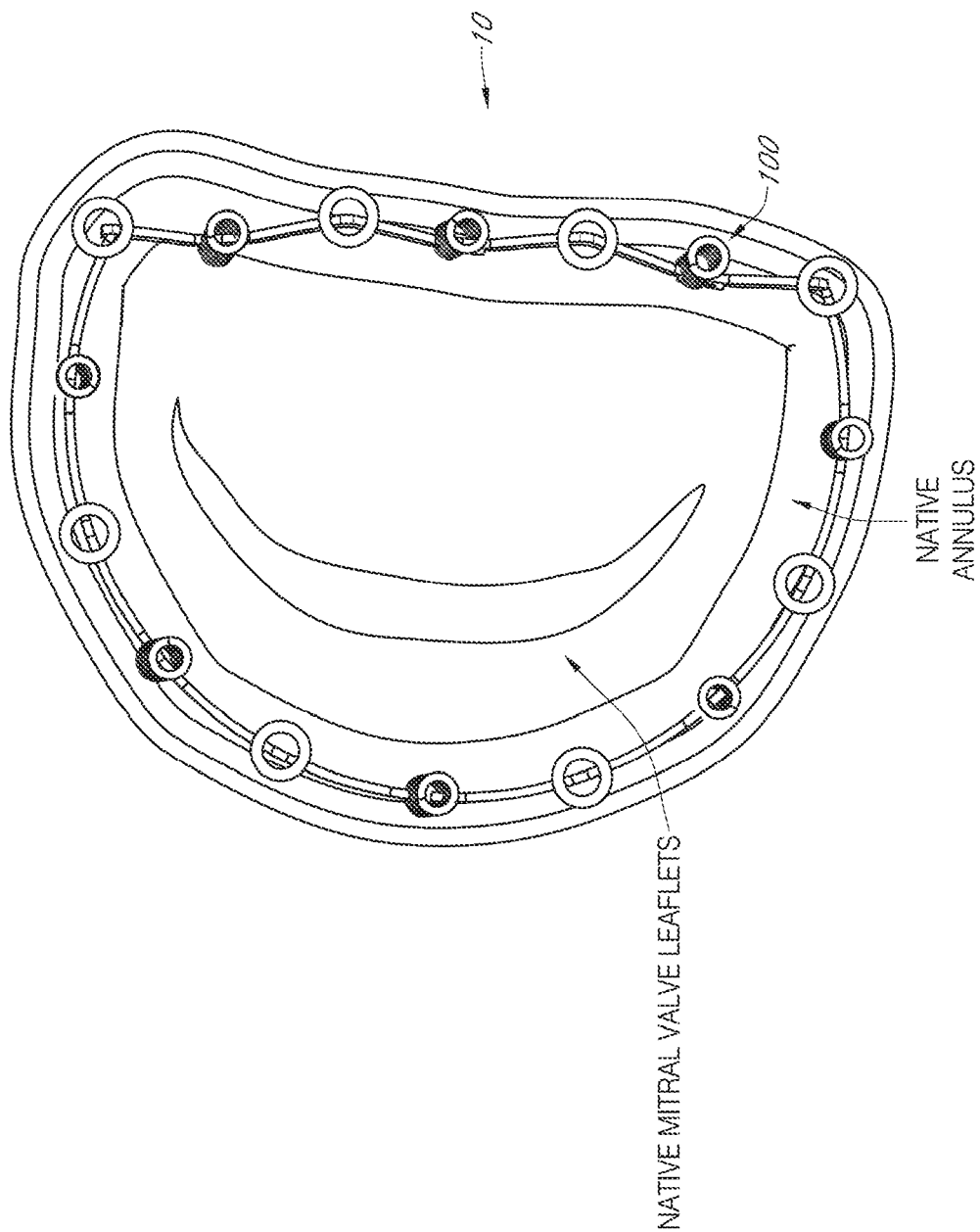
FIGS. 20A-20B are top and perspective views respectively of an embodiment of a heart valve device having a frame embodied as a "D"-shaped ring.
Figure 20B:
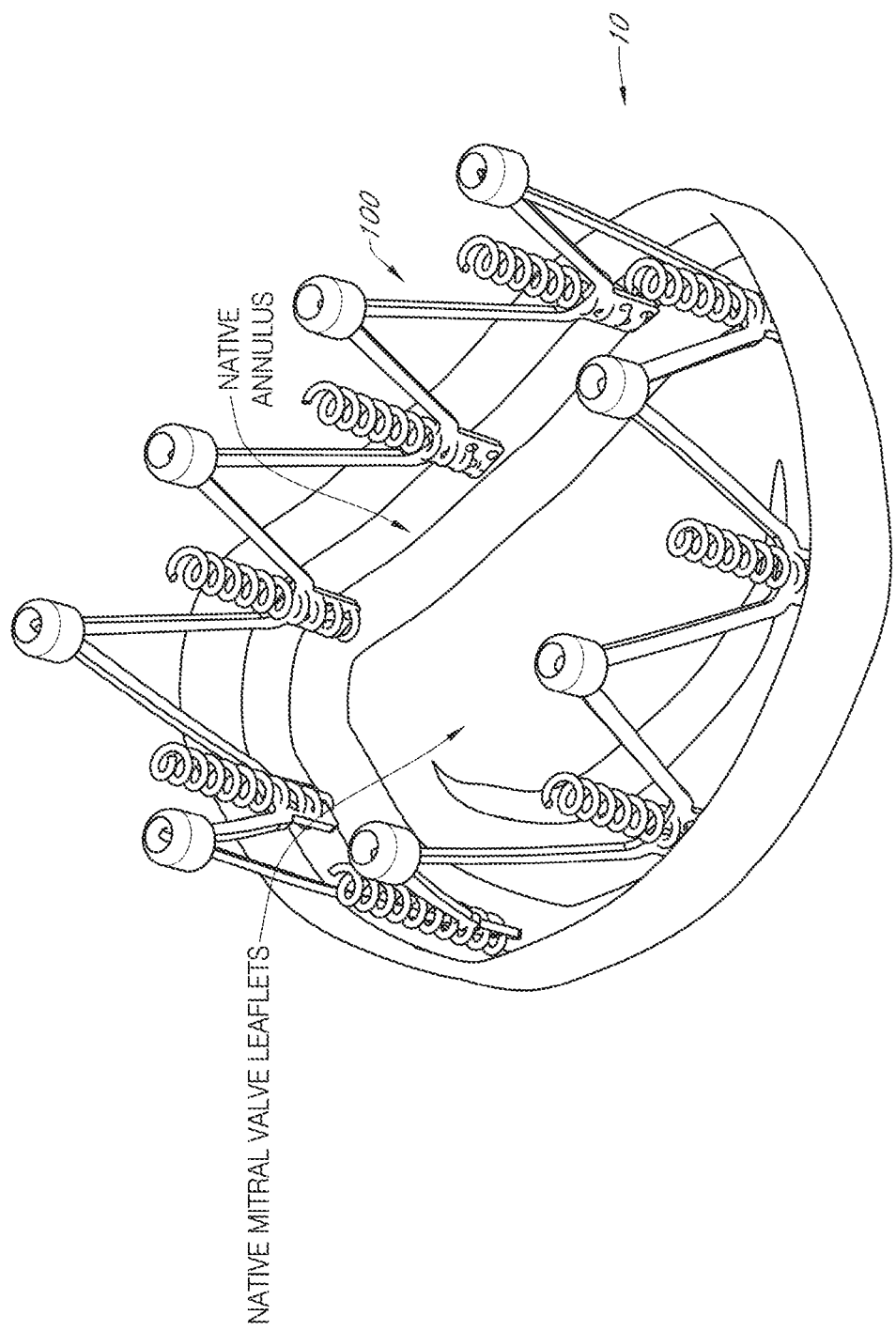

FIGS. 20A-20B are top and perspective views respectively of an embodiment of the heart valve device 10 having a frame embodied as a "D"-shaped ring. The device 10 may include a frame 100 having a body 110 with a "D" shape. The device 10 can be configured, for example shape set, to have the shape of a "D". The device 10 in its "D" shape, can be placed in the naturally "D" shaped annulus, anchored, and cinched to reduce the native annulus width(s). The straight part of the "D" on the device may better match the natural shape and contour of the annulus along the posterior wall.

Figure 20C:
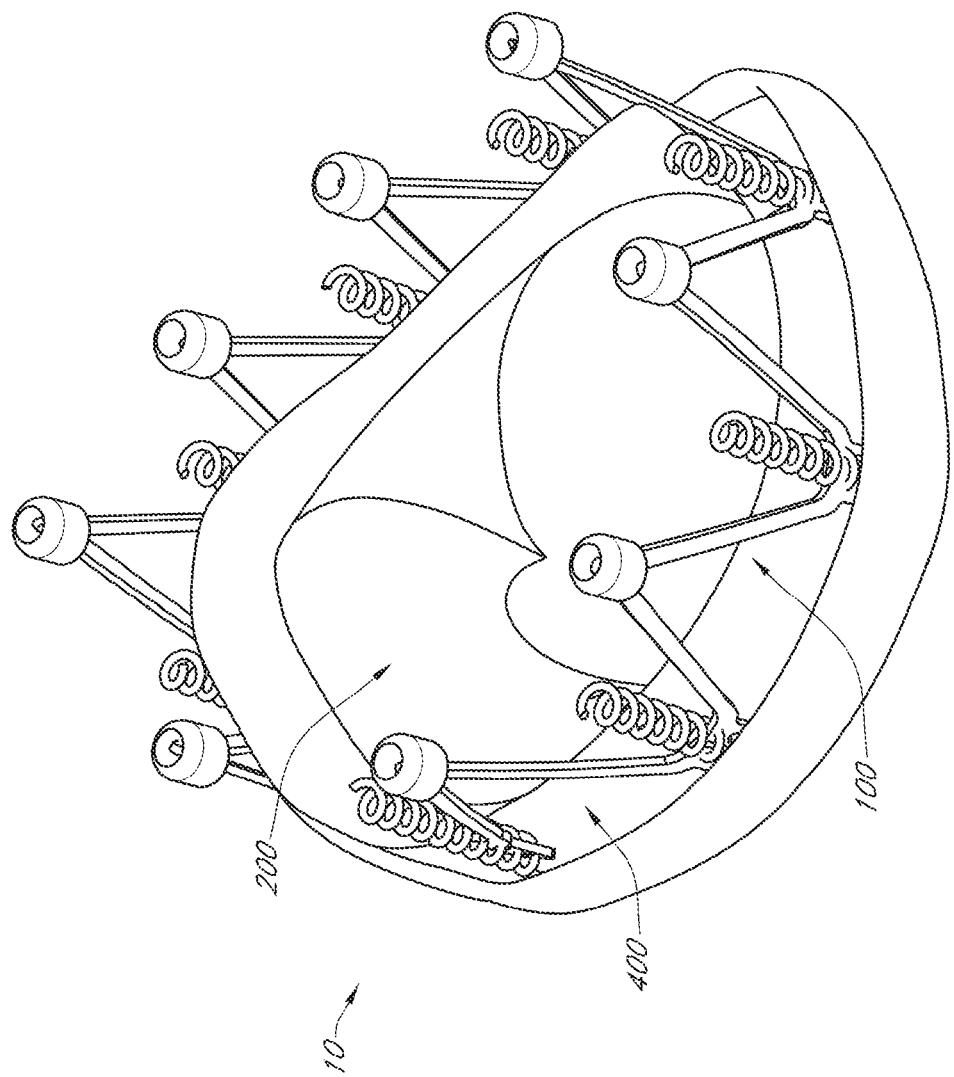
FIG. 20C is a perspective view of the device of FIGS. 20A-20B with a valve.

FIG. 20C is a perspective view of the device 10 of FIGS. 20A-20B with a valve 200. The device 10 may include a frame 100 having a D-shaped body 110 coupled with, or configured to couple with, the valve 200. The frame 100 may have the valve 200 built into it or secondarily attached. The device 10 can be placed in the annulus, anchored, and cinched to reduce the native annulus diameter. The device 10 will maintain its D shape with the valve 200.

Figure 21A:
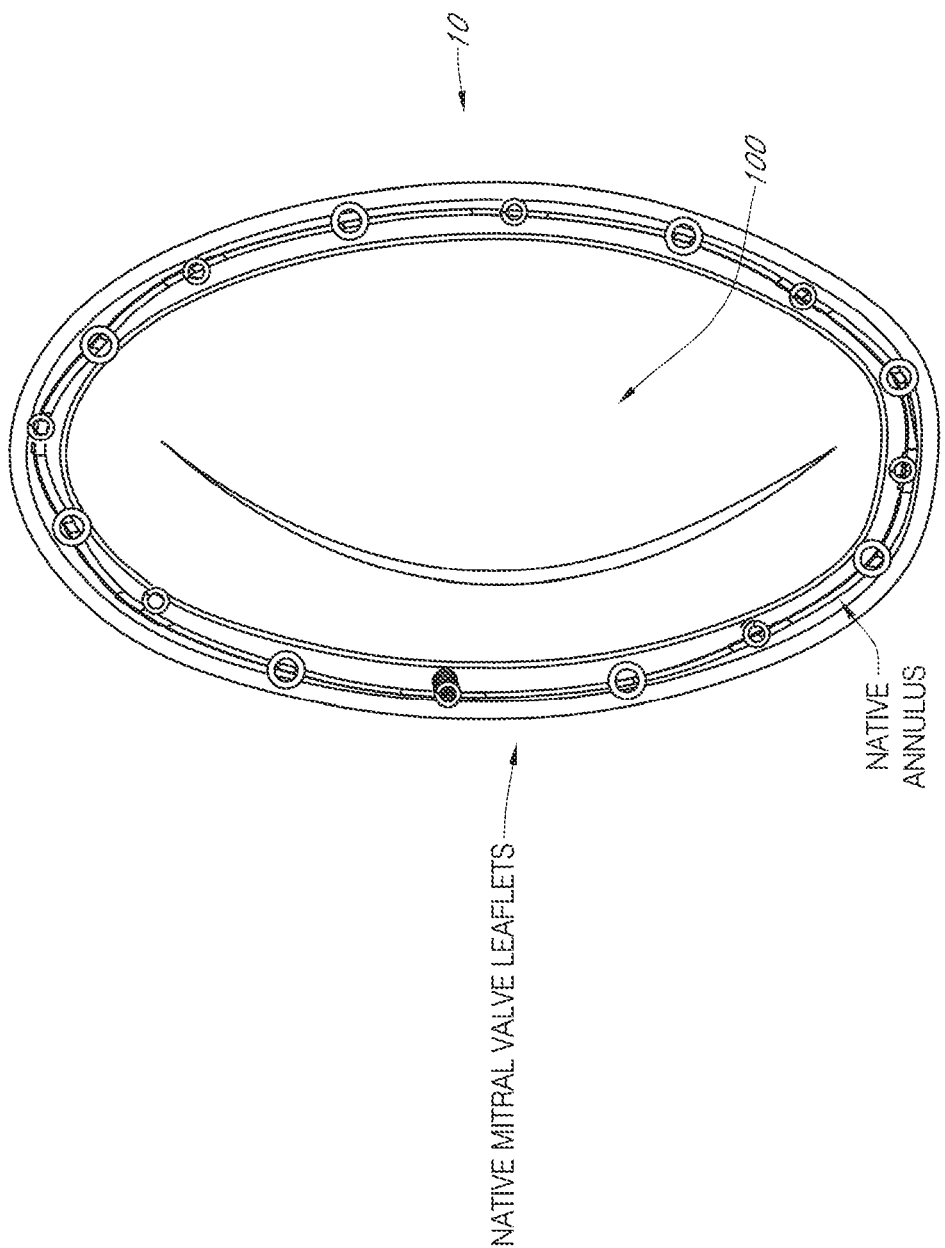
FIGS. 21A-21B are top and perspective views respectively of an embodiment of a heart valve device having a frame embodied as an oblong ring.
Figure 21B:
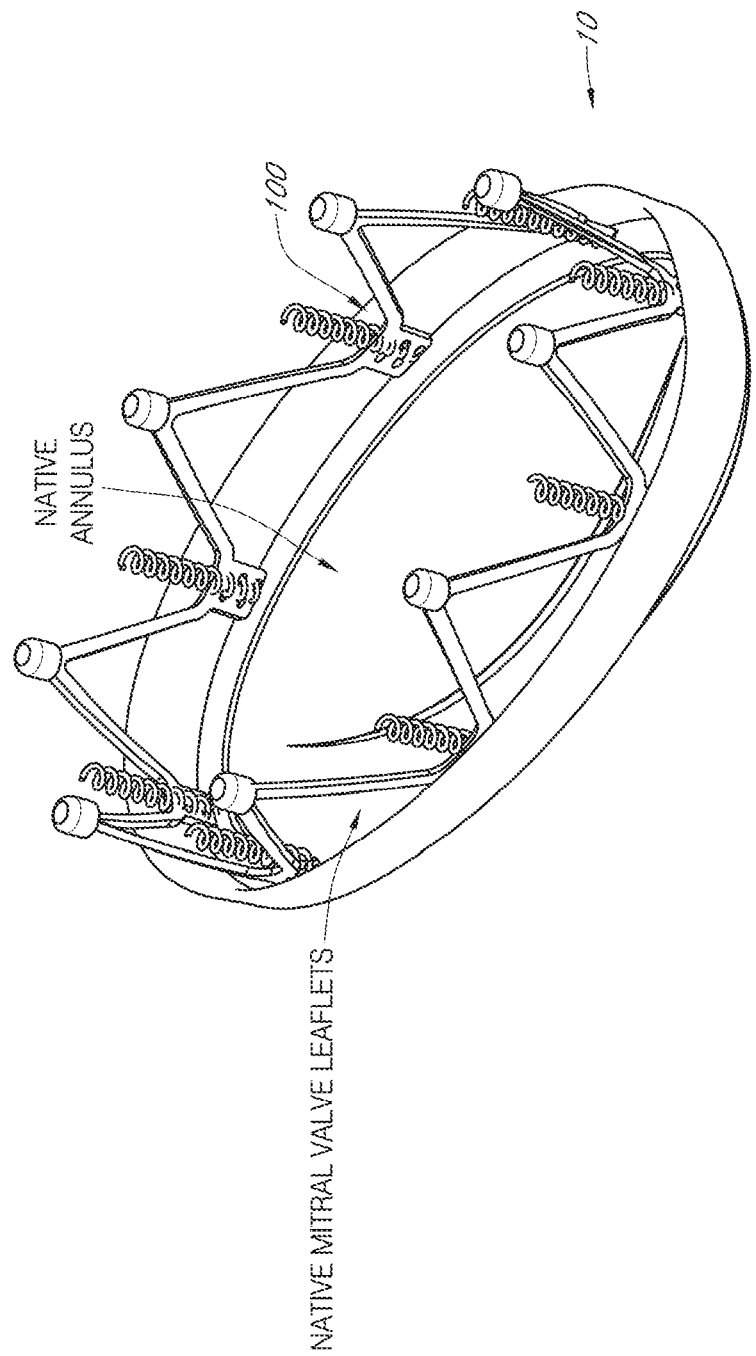

FIGS. 21A-21B are top and perspective views respectively of an embodiment of a heart valve device 10 having a frame 100 embodied as an oblong ring. The device 10 may include a frame 100 having a body 110 with an oval-like shape. The body 110 may be rounded in the general shape of an oval, ellipse, or the like. The device 10, in its oval-like shape, can be placed in or around the annulus, anchored and cinched to reduce the native annulus diameter, after which the device 10 maintains its original oval-like shape. The device 10 can be controlled thru cinching to maintain its oval shape or controlled to constrict to a more circular configuration. Maintaining an oval shape may minimize the amount of cinching required if the apex of the long axis is aligned with the commisures. By stretching the annulus in this direction the anterior-posterior (AP) distance is naturally decreased, which may help reduce any regurgitation. Such cinching, with this and other embodiments, may be done with the moveable restraint 144, which may be a collar and/or a loop. The restraint 144 may include the loop coupled with and/or carried by the frame 100 and surrounding the central lumen of the frame 100. The restraint 144 may be configured to reversibly adjust the size/shape of the frame 100 radially within a working range.

Figure 21C:
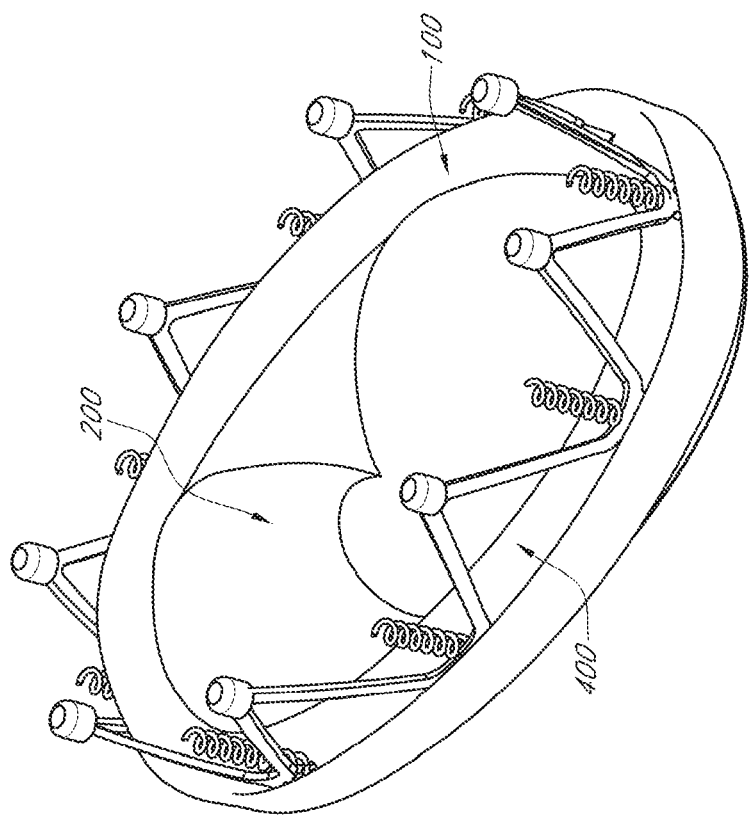
FIG. 21C is a perspective view of the device of FIGS. 21A-21B with a valve.

FIG. 21C is a perspective view of the device of FIGS. 21A-21B with a valve. The device 10 may include a frame 100 having an oval-shaped body 110 coupled with, or configured to couple with, the valve 200. The frame 100 may have the valve 200 built into it or secondarily attached. The device 10 can be placed in the annulus, anchored, and cinched to reduce the native annulus diameter. The device 10 can maintain an oval shape or other rounded shape based on the amount of cinching.

Figure 22A:
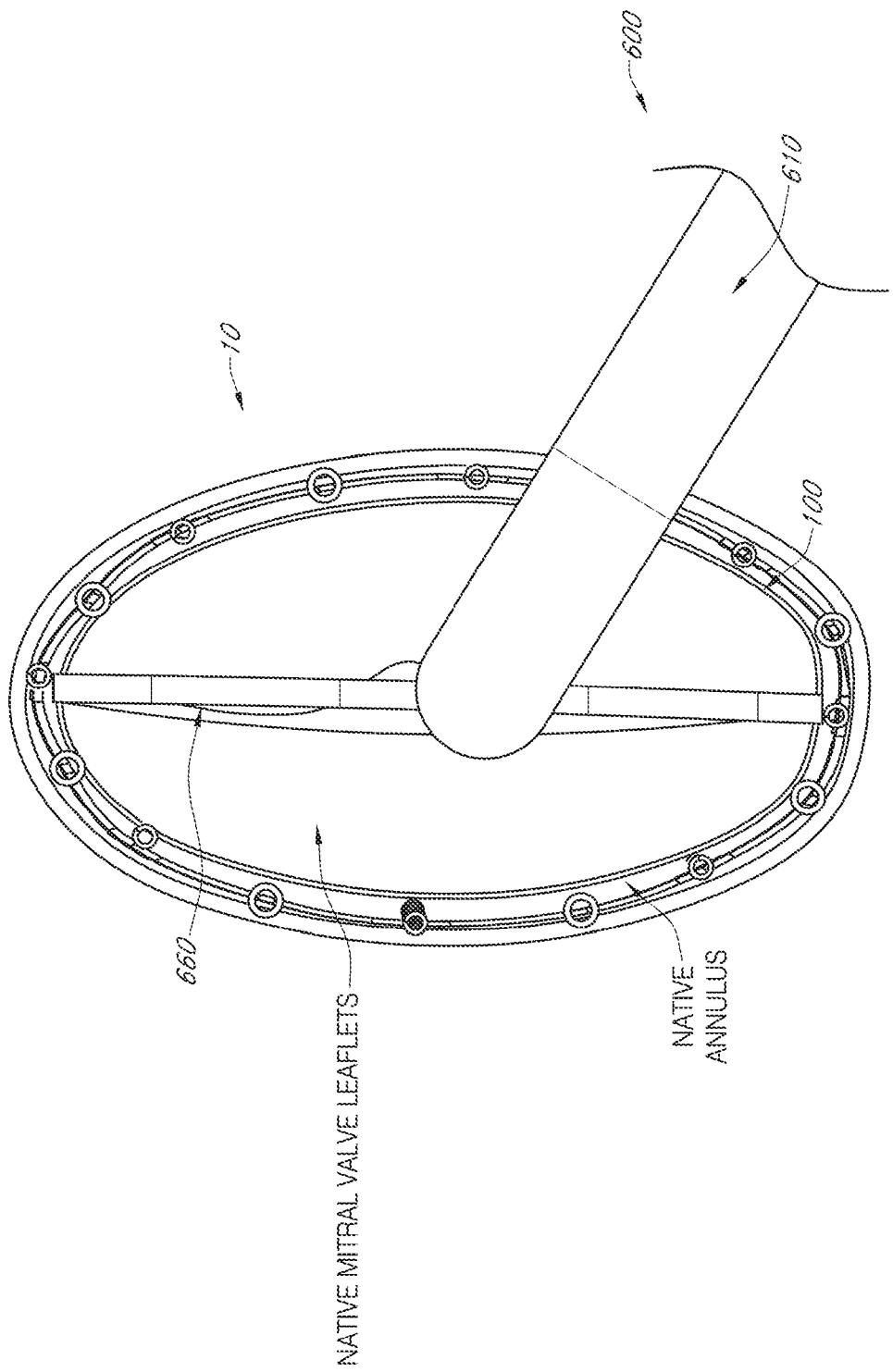
FIGS. 22A-22B are partial top and perspective views respectively of an embodiment of a delivery and shaping system for delivering and shaping, for example ovalizing, the various heart valve devices described herein.
Figure 22B:
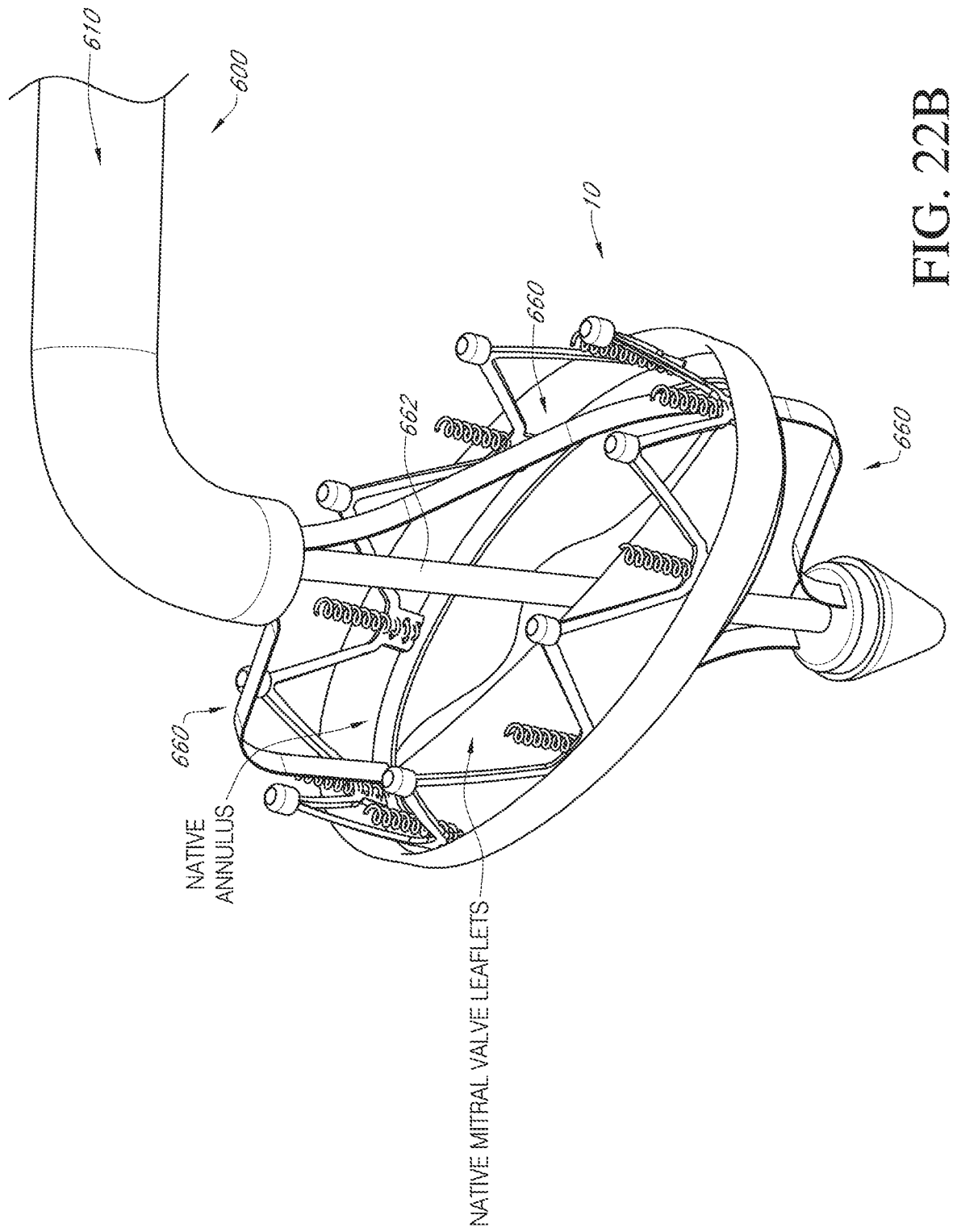

FIGS. 22A-22B are partial top and perspective views respectively of an embodiment of a delivery and shaping system for delivering and shaping, for example ovalizing, the various heart valve devices described herein. The device 10 may include an ovalizing feature and a frame configured to be shaped like an oval. One method for ovalizing a round ring and the annulus is to use a catheter based device to simultaneously stretch them both along the same axis as the commisures. The device may be made of a looped, flat ribbon that has a pre-set bend to it. When the ribbon exits the catheter, the distal end of the loop is pulled in a proximal direction while the proximal end of the ribbon remains stationary. This will force the ribbon into a wide loop and push the device annulus outward at the commisures to create the desired oval shape. The oval ring with a valve 200 either built into it or attached, can be placed in the annulus, anchored, and cinched to reduce the native annulus diameter. The device can maintain either it oval shape, or a rounded shape, based on the amount of cinching. This can be accomplished with a new functional valve 200.

Figure 22C:
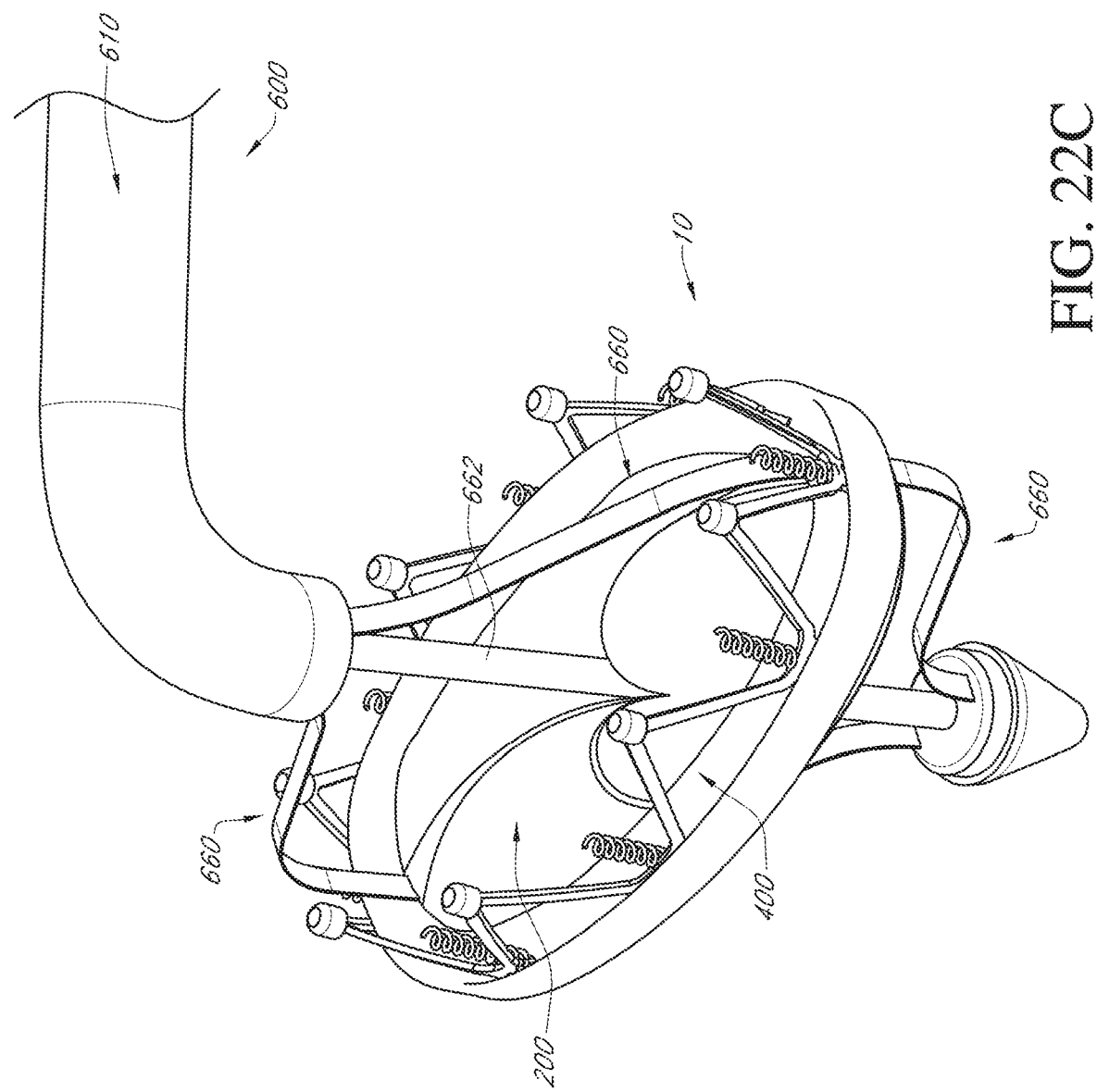
FIG. 22C is a perspective view of the system and device of FIGS. 22A-22B with a valve coupled with the device.

FIG. 22C is a perspective view of the system and device of FIGS. 22A-22B with a valve coupled with the device. The oval ring with an artificial valve 200 either built into it or attached, can be placed in the annulus, anchored, and cinched to reduce the native annulus diameter. The device can maintain either it oval shape, or a rounded shape, based on the amount of cinching. This can be accomplished with a new functional valve 200.

The device 10 may include an ovalizing feature and a frame 100 configured to be shaped like an oval, where the frame 100 is coupled with, or configured to couple with, the valve 200. The frame 100 may have the valve 200 and/or ovalizing feature built into it or secondarily attached. The device 10 can be placed in the annulus, anchored, and cinched to reduce the native annulus diameter. The device 10 can maintain an oval shape or other rounded shape based on the amount of cinching.

Some methods for ovalizing the annulus are described below. Each may be utilized with a delivery catheter.

Figure 23:
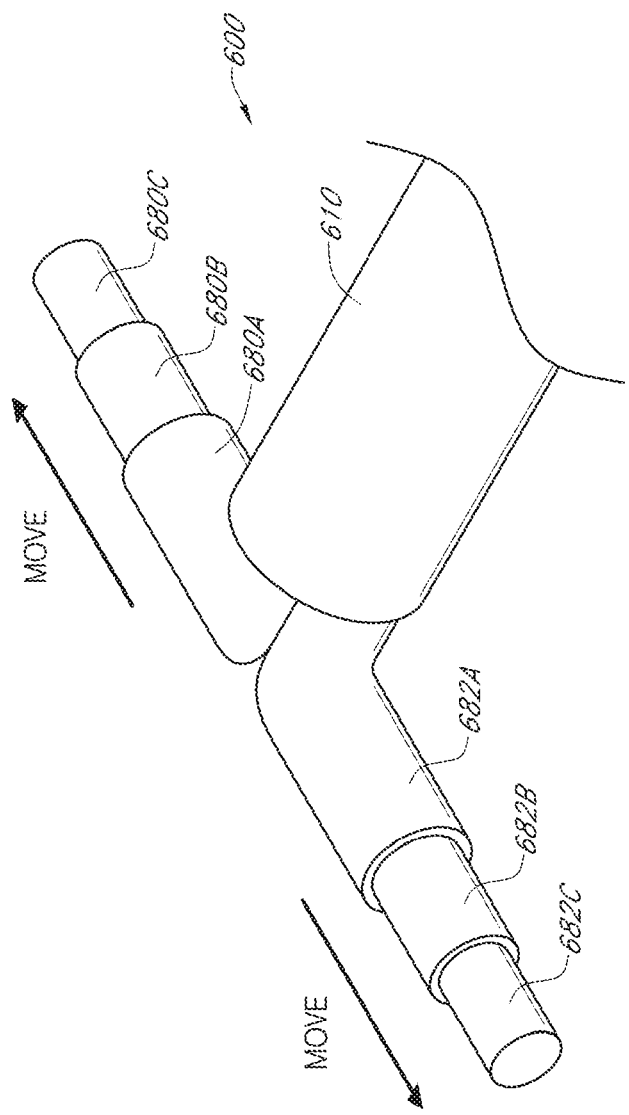
FIG. 23 is a partial perspective view of an embodiment of a piston-based delivery and shaping system for delivering and shaping, for example ovalizing, the various heart valve devices described herein.

FIG. 23 is a partial perspective view of an embodiment of a piston-based delivery and shaping system for delivering and shaping, for example ovalizing, the various heart valve devices described herein. A pair of opposing shafts with telescoping member can be used to distend the annulus in opposite directions to create an oval.

Figure 24B:
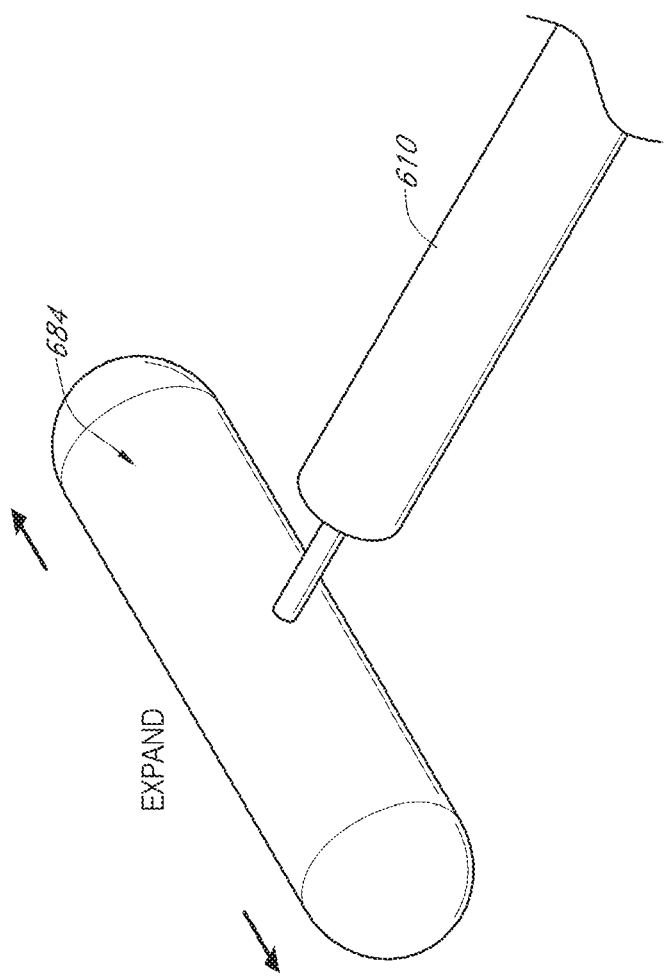

FIGS. 24A-24B are partial perspective views of an embodiment of a balloon-based delivery and shaping system for delivering and shaping, for example ovalizing, the various heart valve devices described herein. A liquid filled balloon with anvil ends and a central shaft connecting them can be used to form an oval annulus. The balloon could also be shaped like a long cylinder with round ends and having the fill port entering in the middle of the long. This type of balloon may also create enough hydraulic force to expand the annulus.

Figure 25A:
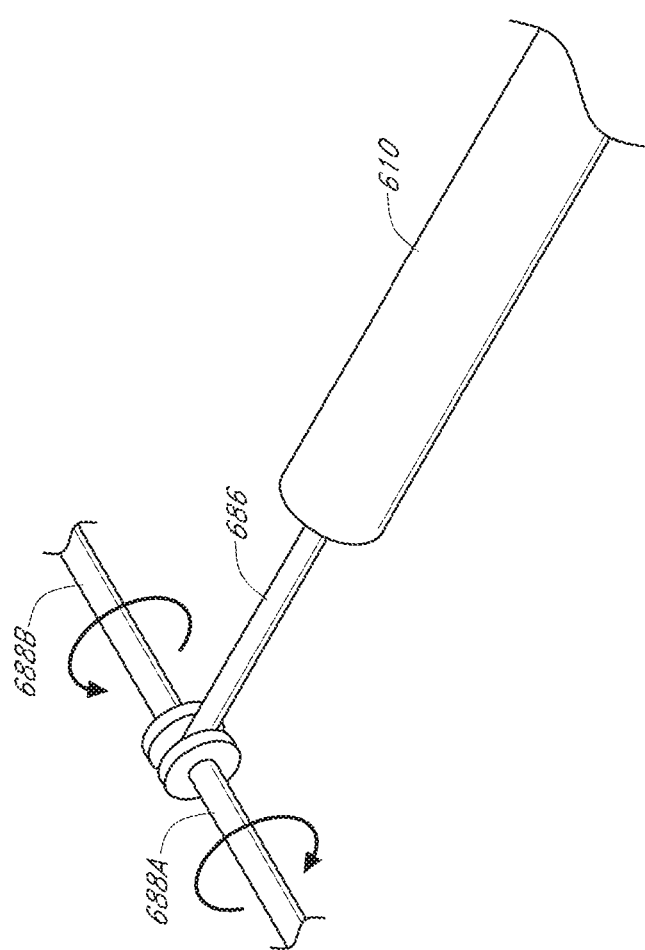
FIGS. 25A-25B are partial perspective views of an embodiment of a rotating shaft-based delivery and shaping system for delivering and shaping, for example ovalizing, the various heart valve devices described herein.
Figure 25B:
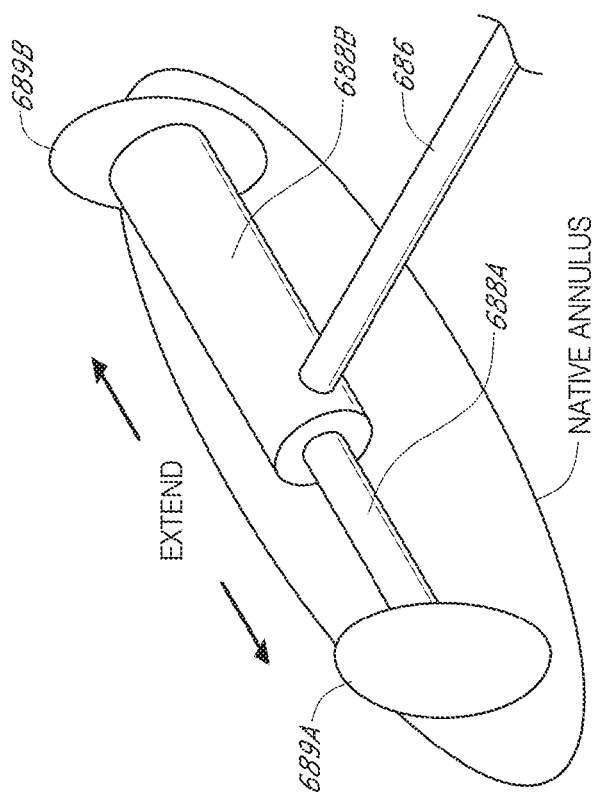

FIGS. 25A-25B are partial perspective views of an embodiment of a rotating shaft-based delivery and shaping system for delivering and shaping, for example ovalizing, the various heart valve devices described herein. A device that exits the delivery catheter may maintain an proximal external connection that can apply torque to two opposing shafts. As the shafts turn in opposite directions, they are extended outward and push against the annulus to create an oval.

While there has been illustrated and described what are presently considered to be example embodiments, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular embodiments disclosed, but that such claimed subject matter may also include all embodiments falling within the scope of the appended claims, and equivalents thereof.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment may be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the inventions are susceptible to various modifications, and alternative forms, specific examples thereof have been shown in the drawings and are herein described in detail. It should be understood, however, that the inventions are not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", "up to about," and "substantially" as used herein include the recited numbers, and also represent an amount or characteristic close to the stated amount or characteristic that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount or characteristic. Features of embodiments disclosed herein preceded by a term such as "approximately", "about", and "substantially" as used herein represent the feature with some variability that still performs a desired function or achieves a desired result for that feature.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced embodiment recitation is intended, such an intent will be explicitly recited in the embodiment, and in the absence of such recitation no such intent is present. For example, as an aid to understanding, the disclosure may contain usage of the introductory phrases "at least one" and "one or more" to introduce embodiment recitations. However, the use of such phrases should not be construed to imply that the introduction of an embodiment recitation by the indefinite articles "a" or "an" limits any particular embodiment containing such introduced embodiment recitation to embodiments containing only one such recitation, even when the same embodiment includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce embodiment recitations. In addition, even if a specific number of an introduced embodiment recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, embodiments, or drawings, should be understood to contemplate the possibilities of including one of the terms, either of the terms, or both terms. For example, the phrase "A or B" will be understood to include the possibilities of "A" or "B" or "A and B."

Although the present subject matter has been described herein in terms of certain embodiments, and certain exemplary methods, it is to be understood that the scope of the subject matter is not to be limited thereby. Instead, the Applicant intends that variations on the methods and materials disclosed herein which are apparent to those of skill in the art will fall within the scope of the disclosed subject matter.

What is claimed is:

1. An implantable heart valve device comprising:
a frame having a proximal end and a distal end and comprising at least a first pair of adjacent struts, the frame including an anti-backout feature configured to resist movement of the frame within a valve annulus;
a plurality of distally facing anchors carried by and extending distally away from the distal end of the frame in a distal direction and having distally extending ends configured to at least partially embed into tissue surrounding a native valve;
a valve disposed within the frame; and
a moveable restraint coupled with the frame and configured to restrain the frame at a desired configuration.

2. The implantable heart valve device of claim 1, wherein the frame comprises a proximal end and a distal end, and the anti-backout feature is disposed on the distal end of the frame, the proximal end of the frame, or both.

3. The implantable heart valve device of claim 2, wherein the anti-backout feature comprises a skirt formed from one of the proximal end or the distal end of the frame.

4. The implantable heart valve device of claim 3, wherein the frame is disposed about a central axis, and the skirt is angled relative to the central axis of the frame.

5. The implantable heart valve device of claim 4, wherein the skirt is formed from the distal end of the frame and angled upwards towards the proximal end of the frame.

6. The implantable heart valve device of claim 4, wherein the skirt is formed from the proximal end of the frame and angled towards the distal end of the frame.

7. The implantable heart valve device of claim 4, wherein the skirt supports the distally facing anchors and angularly displaces the distally facing anchors relative to the central axis of the frame.

8. The implantable heart valve device of claim 7, wherein the skirt is configured to provide different angular displacements from the central axis for at least two of the distally facing anchors.

9. The implantable heart valve device of claim 3, wherein the frame is comprised of a plurality of struts joined in pairs to form a plurality of vertices, and wherein the skirt is formed from the plurality of vertices.

10. The implantable heart valve device of claim 1, wherein the plurality of distally facing anchors are rotatably carried by the frame.

11. The implantable heart valve device of claim 1, wherein the frame is disposed about a central axis, and the anti-backout feature is formed from a material that expands during deployment of the frame to change an angular displacement between the anti-backout feature and the central axis of the frame.

12. An implant device comprising:
a frame having a proximal end and a distal end, the frame comprised of a plurality of adjacent struts joined to provide proximal apices and distal apices, the frame including an anti-backout feature configured to resist movement of the frame within a valve annulus;
a plurality of anchors coupled to the anti-backout feature of the frame and having distal ends extending distally away from the distal end of the frame in a distal direction and configured to engage tissue; and
at least one moveable restraint coupled to at least one proximal apex of the frame and configured to restrain the frame to a contracted configuration.

13. The implant device of claim 12, wherein the anti-backout feature is formed on the distal end of the frame, the proximal end of the frame, or both.

14. The implant device of claim 12, wherein the anti-backout feature comprises a skirt formed from one of the proximal apices or the distal apices of the frame.

15. The implant device of claim 14, wherein the frame is disposed about a central axis, and the skirt is angled relative to the central axis of the frame.

16. The implant device of claim 15, wherein the skirt is formed from the distal end of the frame and angled upwards towards the proximal end of the frame.

17. The implant device of claim 15, wherein the skirt supports the distally facing anchors and angularly displaces the distally facing anchors relative to the central axis of the frame.

18. The implant device of claim 17, wherein the skirt is angularly displaced to different extents around a circumference of the frame to provide different angular displacements for the distally facing anchors.

19. The implant device of claim 12, wherein the frame is disposed about a central axis, and the anti-backout feature is formed from a material that expands during deployment of the frame to change an angular displacement between the anti-backout feature and the central axis of the frame.

20. A method comprising:
deploying a distal end of a delivery catheter to a native valve, the distal end of the delivery catheter carrying an implant comprising:
a frame comprising a proximal end and a distal end, the frame comprised of a plurality of adjacent struts joined to provide proximal and distal apices, the frame including an anti-backout feature configured to resist movement of the frame within a valve annulus;
a plurality of distally facing anchors extending distally away from the distal end of the frame in a distal direction, at least some of the distally facing anchors carried by the anti-backout feature of the frame and having distally extending ends configured to engage tissue;
a valve, disposed within the frame; and
at least one moveable restraint coupled to at least one proximal apex of the frame and configured to restrain the frame to a contracted configuration;
positioning the implant within the native valve, causing the anti-backout feature to expand within the native valve to secure the implant within a native valve annulus; and
driving the plurality of distally facing anchors into the native valve annulus to retain the valve within the native valve annulus.

* * * * *